US012319715B2

(12) United States Patent
Samulski et al.

(10) Patent No.: US 12,319,715 B2
(45) Date of Patent: *Jun. 3, 2025

(54) MODIFIED CAPSID PROTEINS FOR ENHANCED DELIVERY OF PARVOVIRUS VECTORS

(71) Applicant: The University of North Carolina at Chapel Hill, Chapel Hill, NC (US)

(72) Inventors: Richard Jude Samulski, Chapel Hill, NC (US); Jayme Warischalk, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/407,716

(22) Filed: Aug. 20, 2021

(65) Prior Publication Data

US 2021/0403510 A1    Dec. 30, 2021

Related U.S. Application Data

(62) Division of application No. 16/061,952, filed as application No. PCT/US2016/066466 on Dec. 14, 2016, now Pat. No. 11,124,546.

(60) Provisional application No. 62/266,941, filed on Dec. 14, 2015.

(51) Int. Cl.
*C07K 14/015*    (2006.01)
*A61K 35/76*    (2015.01)
*C12N 15/86*    (2006.01)

(52) U.S. Cl.
CPC ............ *C07K 14/015* (2013.01); *A61K 35/76* (2013.01); *C12N 15/86* (2013.01); *C12N 2750/14143* (2013.01); *C12N 2750/14145* (2013.01)

(58) Field of Classification Search
CPC .......... A61P 21/00; C12N 2750/14021; C12N 2750/14022; C12N 2750/14043; C12N 2750/14121; C12N 2750/14122
See application file for complete search history.

(56) References Cited

U.S. PATENT DOCUMENTS

| 7,892,809 B2 | 2/2011 | Bowles et al. |
| 2007/0196338 A1 | 8/2007 | Samulski et al. |
| 2009/0191597 A1 | 7/2009 | Samulski et al. |
| 2012/0009268 A1* | 1/2012 | Asokan ............... A61P 9/00 435/456 |
| 2016/0289275 A1* | 10/2016 | Chiorini ............. A61K 48/0075 |
| 2019/0048041 A1* | 2/2019 | Asokan ................ A61P 25/00 |

FOREIGN PATENT DOCUMENTS

| JP | 2008523813 A | 7/2008 | |
| JP | 2008538286 A | 10/2008 | |
| JP | 2009535339 A | 10/2009 | |
| JP | 2015532095 A | 11/2015 | |
| WO | 2006066066 A2 | 6/2006 | |
| WO | WO-2007089632 A2 * | 8/2007 | ......... A61K 48/0091 |
| WO | 2008027084 A2 | 3/2008 | |
| WO | WO-2010093784 A2 * | 8/2010 | .......... C07K 14/005 |
| WO | 2014052789 A1 | 4/2014 | |
| WO | 2014193716 A2 | 12/2014 | |

OTHER PUBLICATIONS

"2013 Annual Meeting". ASGCT 16th Annual Meeting. http://www.asgct.org/meetings-educational-programs/asgct-annual-meetings/2013-annual-meeting. Mar. 3, 2013. Accessed via web.archive.org Apr. 28, 2023. (Year: 2013).*
"ASGCT Program", American Society of Gene & Cell Therapy 16th Annual Meeting. Molecular Therapy, vol. 21, i-xv. May 15-18, 2013. Accessed via web.archive.org Apr. 28, 2023. (Year: 2013).*
("Abstracts". ASGCT 16th Annual Meeting, 2013. http://www.asgct.org/meetings-educational-programs/asgct-annual-meetings/2013-annual-meeting/attendee/abstracts. Mar. 4, 2013. Accessed via web.archive.org Apr. 28, 2023. (Year: 2013).*
"Registration: Annual Meeting Registration Open Now". ASGCT. https://annualmeeting.asgct.org/register; Accessed Apr. 28, 2023. (Year: 2023).*
Xie Q, Lerch TF, Meyer NL, Chapman MS. Structure-function analysis of receptor-binding in adeno-associated virus serotype 6 (AAV-6). Virology. Nov. 10, 2011;420(1):10-9. doi: 10.1016/j.virol.2011.08.011. Epub Sep. 13, 2011. PMID: 21917284; PMCID: PMC3185213. (Year: 2011).*
Wu Z, Asokan A, Grieger JC, Govindasamy L, Agbandje-McKenna M, Samulski RJ. Single amino acid changes can influence titer, heparin binding, and tissue tropism in different adeno-associated virus serotypes. J Virol. Nov. 2006;80(22):11393-7. doi: 10.1128/JVI.01288-06. Epub Aug. 30, 2006. (Year: 2006).*
University of North Carolina Graduate School Handbook. https://handbook.unc.edu/phd.html. Feb. 21, 2015, WayBackMachine.
"U.S. Appl. No. 16/061,952; office action mailed Jan. 3, 2020".
"U.S. Appl. No. 16/061,952; office action mailed Oct. 8, 2020".
"Bowie JU, Reidhaar-Olson JF, Lim WA, Sauer RT. Deciphering the message in protein sequences: tolerance to amino acid substitutions. Science. Mar. 16, 1990;247(4948): 1306-10."
"Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714."
"Examination Report corresponding to Australian Application No. 2016371779 issued May 26, 2020".

(Continued)

*Primary Examiner* — Rachel B Gill
(74) *Attorney, Agent, or Firm* — Myers Bigel, P.A.

(57) ABSTRACT

This invention relates to modified parvovirus capsid proteins with enhanced transduction efficiency, viral vectors comprising the same, and methods of using the same for delivery of nucleic acids to a cell or a subject.

10 Claims, 27 Drawing Sheets

Specification includes a Sequence Listing.

(56) References Cited

OTHER PUBLICATIONS

"Extended European Search Report corresponding to European Application No. 16876517.0 dated Jun. 18, 2019".
"Kussie PH, Parhami-Seren B, Wysocki LJ, Margolies MN. A single engineered amino acid substitution changes antibody fine specificity. J Immunol. Jan. 1, 1994; 152(1 ): 146-52."
"Notification Concerning Transmittal of International Preliminary Report on Patentability corresponding to International Application No. PCT/US2016/066466 mailed Jun. 28, 2018".
"Notification of Transmittal of the International Search Report and the Written Opinion of the International Searching Authority, or the Declaration corresponding to International Application No. PCT/US2016/066466 mailed Apr. 27, 2017".
"Office Action corresponding to Brazilian Application No. BR112018011881-8 issued Mar. 23, 2021".
"Office Action corresponding to Chinese Application No. 201680081759.4 issued Jun. 1, 2021".
"Office Action corresponding to Japanese Application No. 2018-549419 mailed Nov. 4, 2020".
"Office Action corresponding to Russian Application No. 2018125937 issued May 14, 2020".
"Warischalk "Uncovering Structural Components of the Adeno-Associated Viral Capsid that can be Modified to Improve Clinical Gene Therapy Outcomes", Electronic Theses and Dissertations, Jun. 23, 2015, Retrieved from the Internet: https://cdr.lib.unc.edu/record/u".
"Winkler K, Kramer A, Kuttner G, Seifert M, Scholz C, Wessner H, Schneider-Mergener J, Hahne W. Changing the antigen binding specificity by single point mutations of an anti-p24 (H IV-1) antibody. J Immunol. Oct. 15, 2000; 165(8):4505-14."
"Zhong L, Li B, Mah CS, Govindasamy L, et. al. Next generation of adena-associated virus 2 vectors: point mutations in tyrosines lead to high-efficiency transduction at lower doses. Proc Natl Acad Sci U SA. Jun. 3, 2008; 1 05(22):7827-32. Epub May 29, 2008."
Arnett, Andrea L. H., et al., "Herparin-binding correlates with increased efficiency of AAV1- and AAV6-mediated transduction of striated muscle, but negatively impacts CNS transduction", Gene Ther. 20(5):497-503 (2013).
Bowles, Dawn E., et al., "Phase 1 Gene Therapy for Duchenne Muscular Dystrophy Using a Translational Optimized AAV Vector", Molecular Therapy 20(2):443-455 (2012).
Li , et al., ""Single Amino Acid Modification of Adeno-Associated Virus Capsid Changes Transduction and Humoral Immune Profiles", Journal of Virology 86(15):7752-7759 (2012)".
Pakula , et al., ""Genetic analysis of protein stability and function", Annual review of genetics 23:289-310 (1989)".
Warischalk, Jayme K., et al., "Adeno-Associated Virus Capsid Motif That Influences Tissue Specific Vector Transduction In Vivo", AAV Vector Development & Application Abstract 6. 16th Annual Meeting ASGCT. May 15-18, 2013.
Wu , et al., ""Single Amino Acid Changes can Influence Titer, Heparin Binding, and Tissue Tropism in Different Adeno-Associated Virus Serotypes", Journal of Virology 80(22):11393-11397 (2006)".
Wu, Pei , et al., "Mutational Analysis of the Adeno-Associated Virus Type 2 (AAV 2) Capsid Gene and Construction of AAV2 Vectors with Altered Tropism", Journal of Virology 74(18):8635-8647 (2000).
Xie, Qing , et al., "Structure-function Analysis of Receptor-binding in Adeno-Associated Virus Serotype 6 (AAV-6)", Virology 420(1):10-19 (2011).
Zhang, Fuming , et al., "Characterizations of Interations between Herapin/Glycosaminoglycan and Adeno-Associated Virus", Biochemistry 52(36): 6275-6285 (2013).
"Office Action corresponding to Indian Application No. 201847025511 issued Mar. 8, 2022".
"Examination Report corresponding to European Application No. 16876517.0 dated Mar. 11, 2022".
"Office Action corresponding to Japanese Application No. 2018-549419 mailed Oct. 7, 2021".
"Office Action corresponding to Chinese Application No. 20168001759.4 issued Jan. 24, 2022".
"Office Action corresponding to Mexican Application No. MX/a/2018/007237 issued Jan. 21, 2022".
"Office Action corresponding to Chinese Application No. 20168001759.4 issued Jul. 4, 2022".
"Examination Report corresponding to Australian Application No. 2021203779 dated Jun. 1, 2022".
"Office Action corresponding to Canadian Application No. 3,008,013 dated Jan. 13, 2023".
"Office Action corresponding to Japanese Application No. 2022-016322 mailed Feb. 9, 2023".
"Office Action corresponding to Japanese Application No. 2018-549419 mailed May 29, 2023".
"Summons to attend oral proceedings corresponding to European Application No. 16876517.0 dated Mar. 18, 2024".
"Office Action corresponding to Japanese Application No. 2022-016322 mailed Sep. 14, 2023".
"Office Action corresponding to New Zealand Application No. 743916 dated Jul. 9, 2024".
"Office Action corresponding to New Zealand Application No. 783341 dated Jul. 9, 2024".
"Office Action corresponding to Canadian Application No. 3,008,013 mailed Sep. 11, 2024".
"Office Action corresponding to New Zealand Application No. 743916 dated Oct. 14, 2024".
"Office Action corresponding to New Zealand Application No. 783341 dated Oct. 14, 2024".
"Office Action corresponding to New Zealand Application No. 783341 dated Feb. 28, 2025".

* cited by examiner

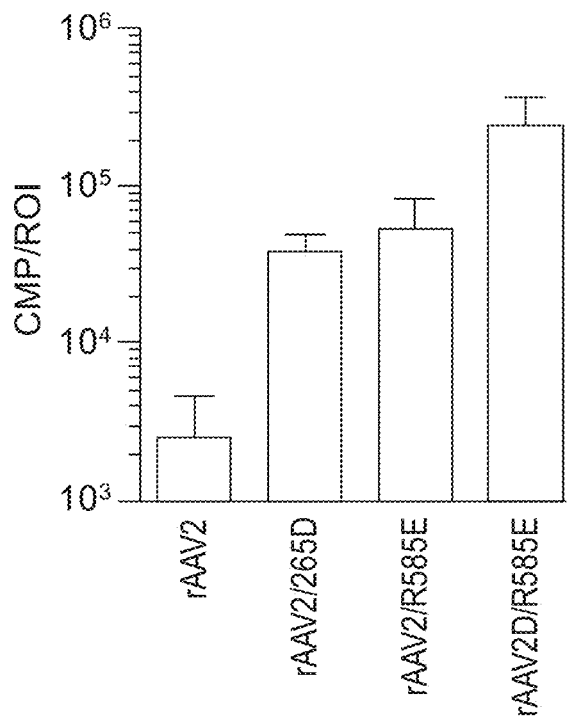
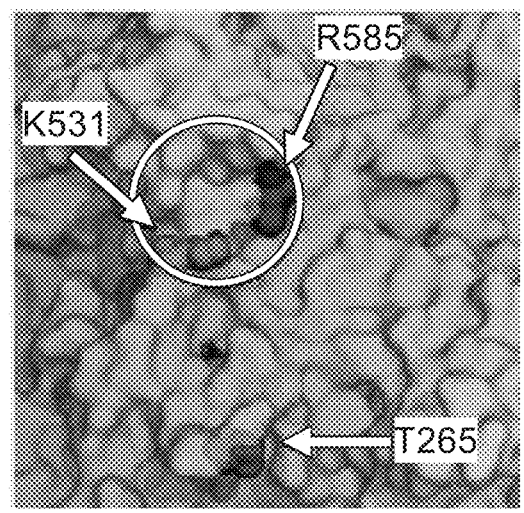
*FIG. 4A*  *FIG. 4B*
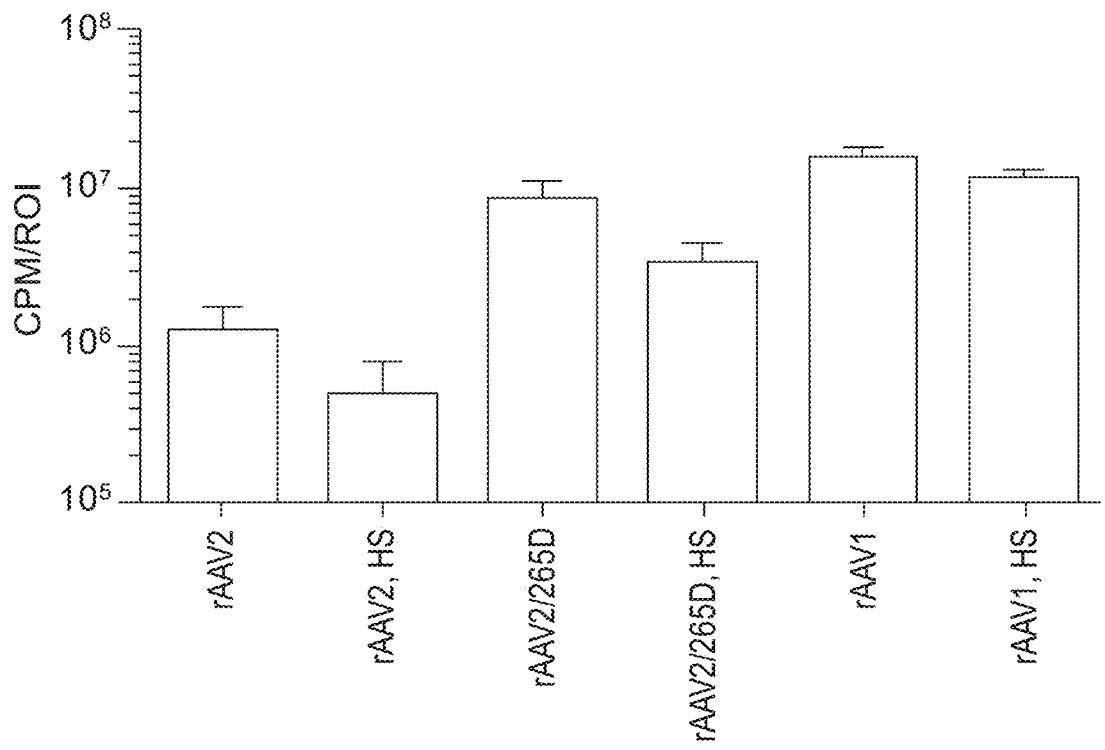
*FIG. 4C*

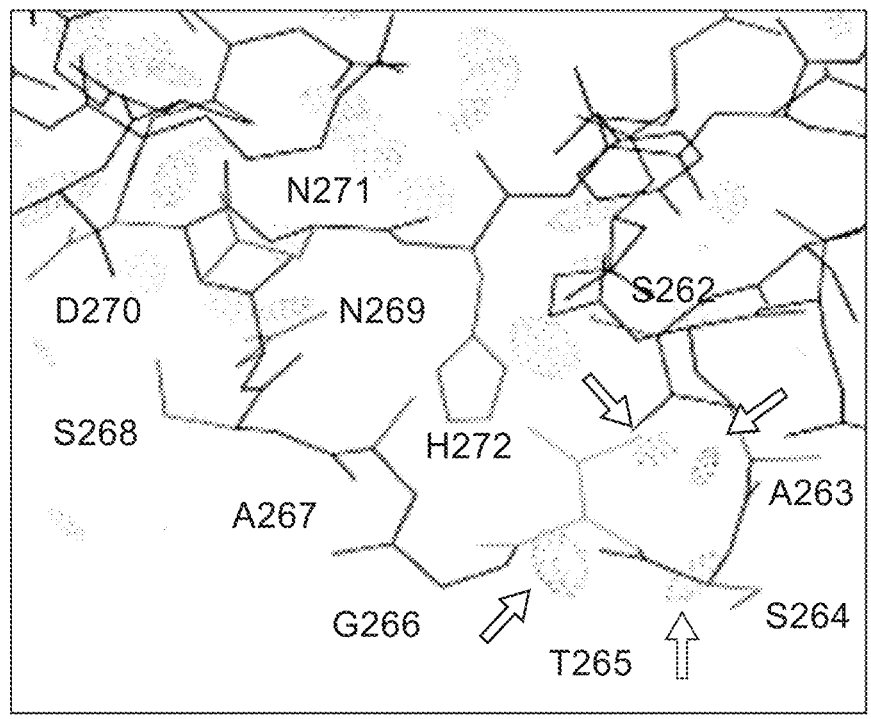
rAAV1
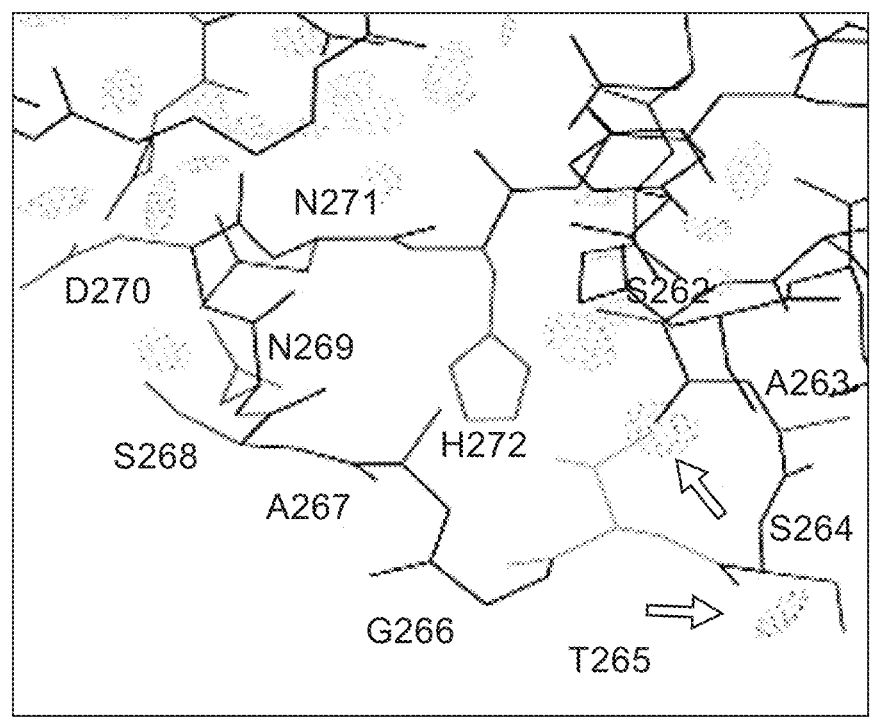
rAAV6
FIG. 8

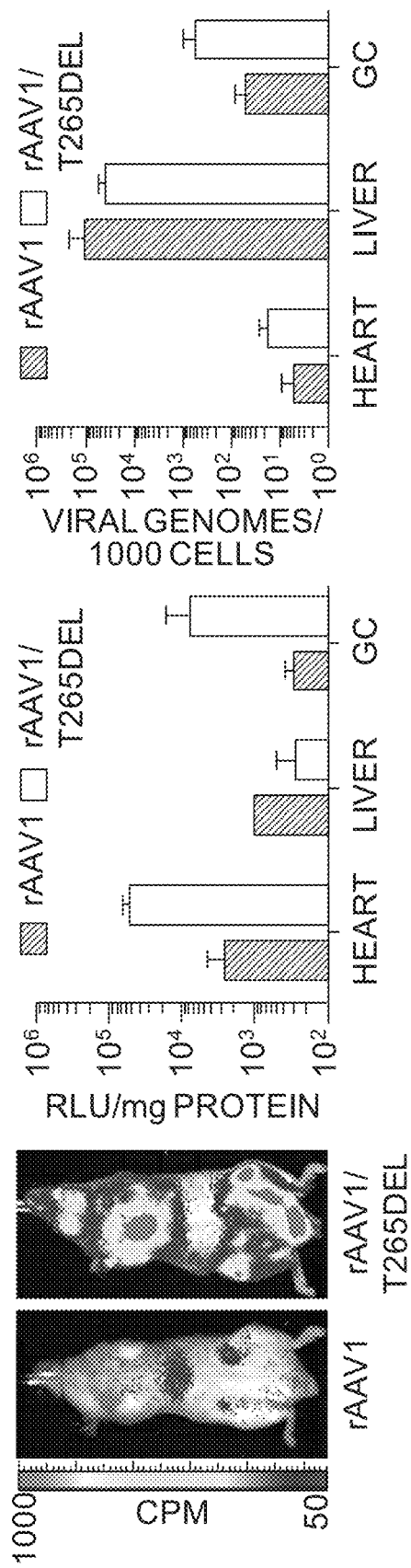

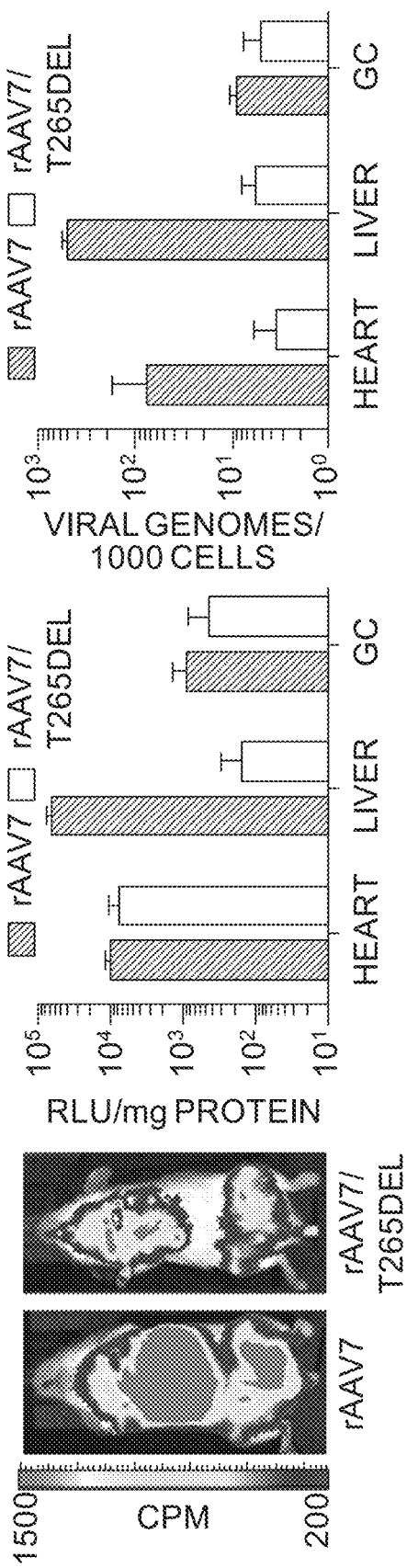

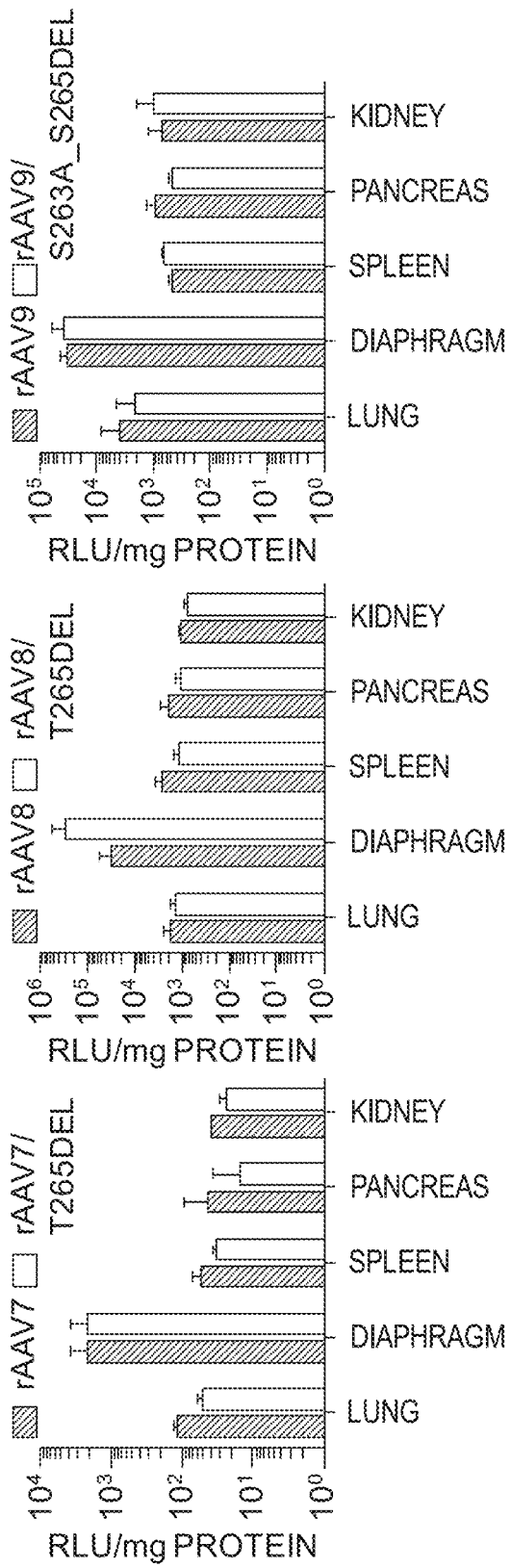
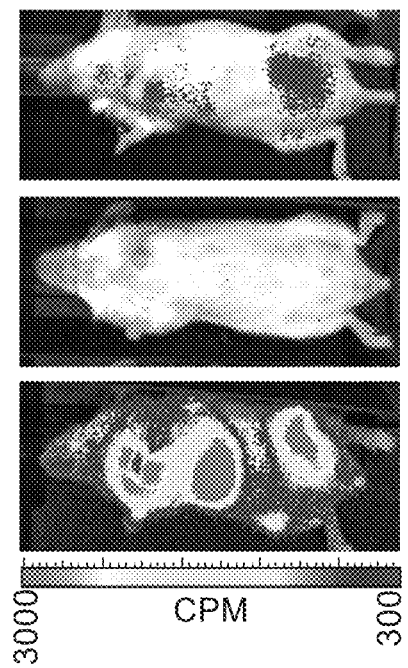
FIG. 17A
FIG. 17B
FIG. 17C
FIG. 17D

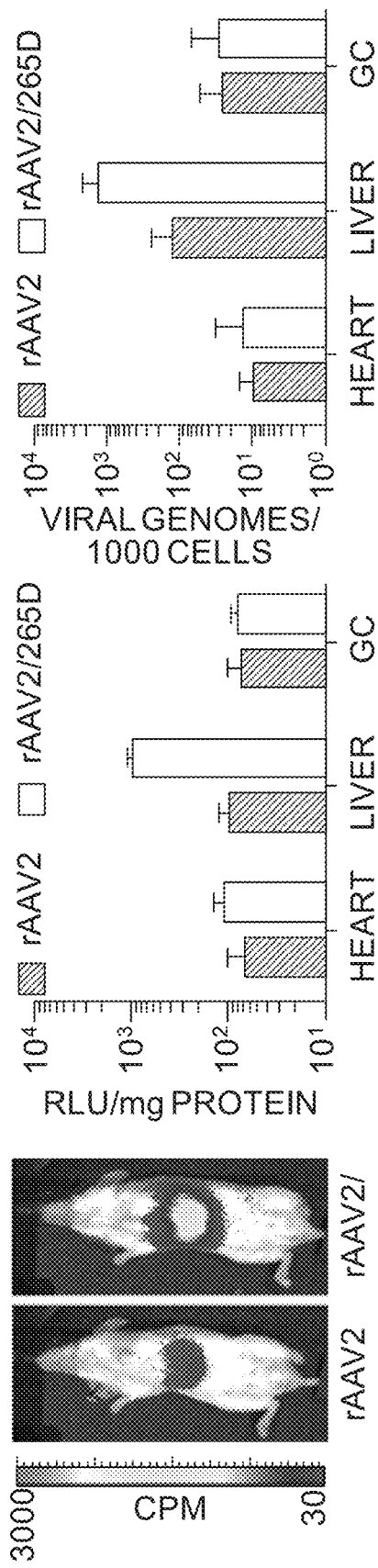
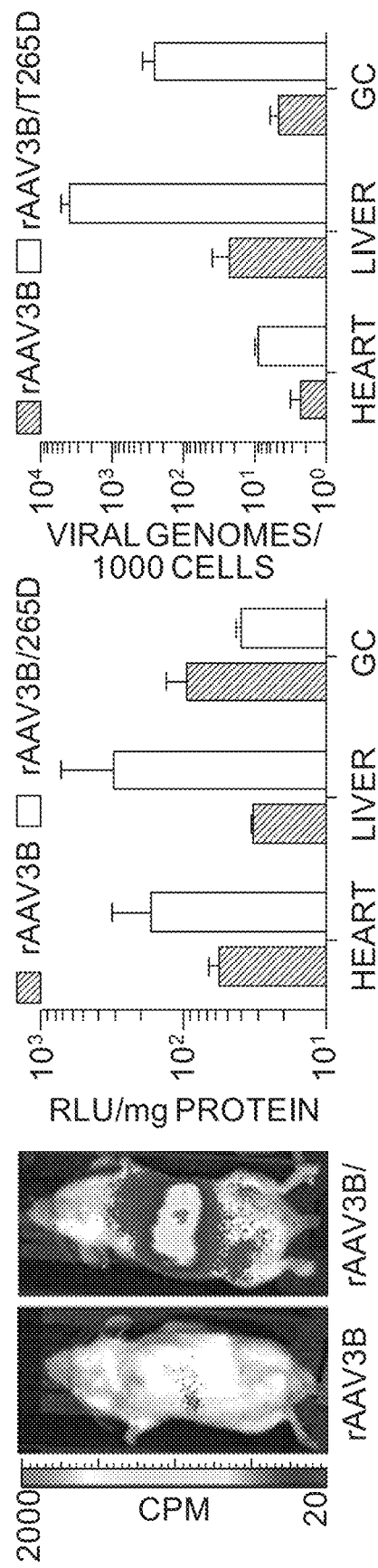
FIG. 18A  FIG. 18B  FIG. 18C
FIG. 18D  FIG. 18E  FIG. 18F

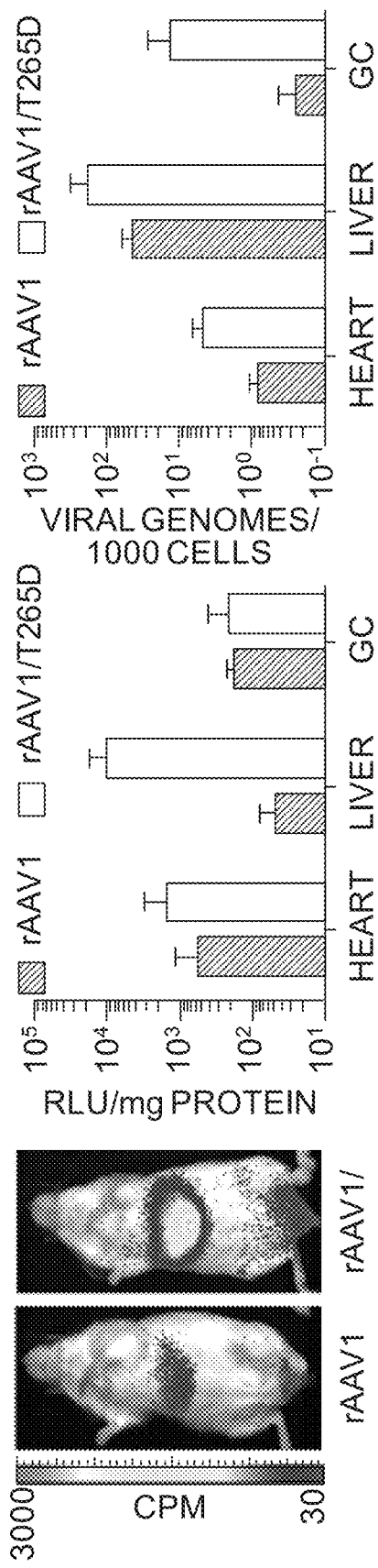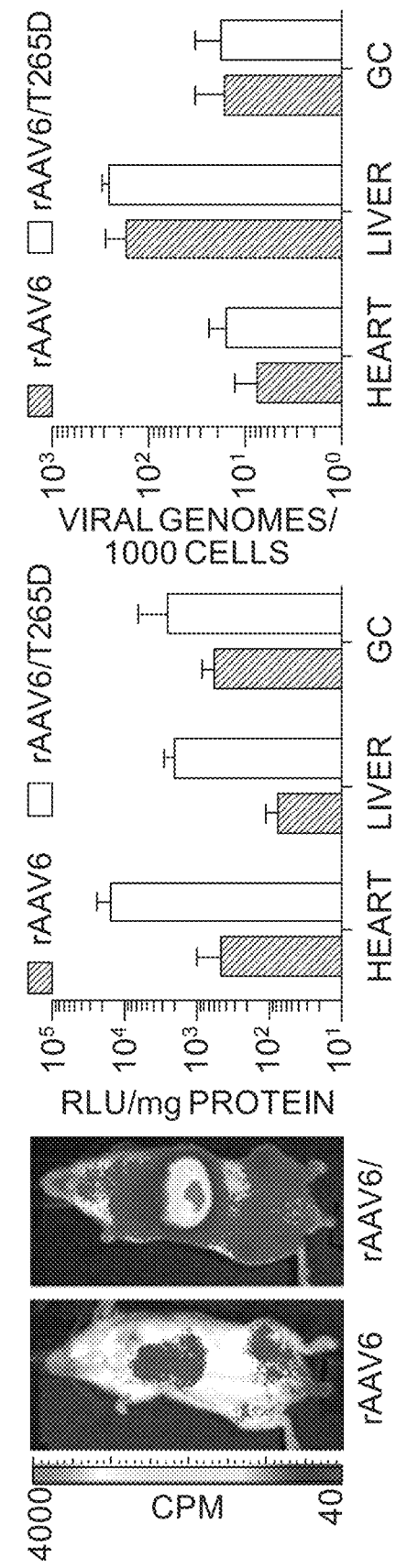

SEQUENCE LISTING

<160> NUMBER OF SEQ ID NOS: 48

<210> SEQ ID NO 1

```
<211> LENGTH: 13
<212> TYPE: PRT
<213> ORGANISM: adeno-associated virus 1

<400> SEQUENCE: 1

Ser Ser Ala Ser Thr Gly Ala Ser Asn Asp Asn His Tyr
1               5                   10

<210> SEQ ID NO 2
<211> LENGTH: 7
<212> TYPE: PRT
<213> ORGANISM: adeno-associated virus 2

<400> SEQUENCE: 2

Ser Ser Gln Ser Gly Ala Ser
1               5

<210> SEQ ID NO 3
<211> LENGTH: 12
<212> TYPE: PRT
<213> ORGANISM: adeno-associated virus 3B

<400> SEQUENCE: 3

Ser Ser Gln Ser Gly Ala Ser Asn Asp Asn His Tyr
1               5                   10

<210> SEQ ID NO 4
<211> LENGTH: 8
<212> TYPE: PRT
<213> ORGANISM: adeno-associated virus 4

<400> SEQUENCE: 4

Glu Ser Leu Gln Ser Asn Thr Tyr
1               5

<210> SEQ ID NO 5
<211> LENGTH: 7
<212> TYPE: PRT
<213> ORGANISM: adeno-associated virus 5

<400> SEQUENCE: 5

Ser Gly Ser Val Asp Gly Ser
1               5

<210> SEQ ID NO 6
<211> LENGTH: 13
<212> TYPE: PRT
<213> ORGANISM: adeno-associated virus 6

<400> SEQUENCE: 6

Ser Ser Ala Ser Thr Gly Ala Ser Asn Asp Asn His Tyr
1               5                   10

<210> SEQ ID NO 7
<211> LENGTH: 8
<212> TYPE: PRT
<213> ORGANISM: adeno-associated virus 8

<400> SEQUENCE: 7

Asn Gly Thr Ser Gly Gly Ala Thr
1               5

<210> SEQ ID NO 8
<211> LENGTH: 9
<212> TYPE: PRT
```

```
<213> ORGANISM: adeno-associated virus 9

<400> SEQUENCE: 8

Ser Asn Ser Thr Ser Gly Gly Ser Ser
1               5

<210> SEQ ID NO 9
<211> LENGTH: 24
<212> TYPE: DNA
<213> ORGANISM: Artificial
<220> FEATURE:
<223> OTHER INFORMATION: Quantitative PCR primer sequence

<400> SEQUENCE: 9
aaaagcactc tgattgacaa atac                                          24

<210> SEQ ID NO 10
<211> LENGTH: 22
<212> TYPE: DNA
<213> ORGANISM: Artificial
<220> FEATURE:
<223> OTHER INFORMATION: Quantitative PCR primer sequence

<400> SEQUENCE: 10
ccttcgcttc aaaaaatgga ac                                            22

<210> SEQ ID NO 11
<211> LENGTH: 19
<212> TYPE: DNA
<213> ORGANISM: Artificial
<220> FEATURE:
<223> OTHER INFORMATION: Quantitative PCR primer sequence

<400> SEQUENCE: 11
aagtcaagga caccgagga                                                19

<210> SEQ ID NO 12
<211> LENGTH: 20
<212> TYPE: DNA
<213> ORGANISM: Artificial
<220> FEATURE:
<223> OTHER INFORMATION: Quantitative PCR primer sequence

<400> SEQUENCE: 12
cccagctgga cagtctctta                                               20

<210> SEQ ID NO 13
<211> LENGTH: 34
<212> TYPE: DNA
<213> ORGANISM: Artificial
<220> FEATURE:
<223> OTHER INFORMATION: Site-directed mutagenesis primer sequence

<400> SEQUENCE: 13
gcaatctcca gtgcttcaga cggggccagc aacg                               34

<210> SEQ ID NO 14
<211> LENGTH: 35
<212> TYPE: DNA
<213> ORGANISM: Artificial
<220> FEATURE:
<223> OTHER INFORMATION: Site-directed mutagenesis primer sequence
<220> FEATURE:
<221> NAME/KEY: misc_feature
<222> LOCATION: (13)..(13)
<223> OTHER INFORMATION: n is a, c, g, or t
```

-continued

<400> SEQUENCE: 14
gcaatctcca gtngcttcag aggggggccag caacg          35

<210> SEQ ID NO 15
<211> LENGTH: 36
<212> TYPE: DNA
<213> ORGANISM: Artificial
<220> FEATURE:
<223> OTHER INFORMATION: Site-directed mutagenesis primer sequence

<400> SEQUENCE: 15
gcaatctcca gtgcttcatt cggggccagc aacgac          36

<210> SEQ ID NO 16
<211> LENGTH: 26
<212> TYPE: DNA
<213> ORGANISM: Artificial
<220> FEATURE:
<223> OTHER INFORMATION: Site-directed mutagenesis primer sequence

<400> SEQUENCE: 16
caagcaaatc agtgcttcaa cggggg          26

<210> SEQ ID NO 17
<211> LENGTH: 23
<212> TYPE: DNA
<213> ORGANISM: Artificial
<220> FEATURE:
<223> OTHER INFORMATION: Site-directed mutagenesis primer sequence

<400> SEQUENCE: 17
gcaaatctcc gcttcaacgg ggg          23

<210> SEQ ID NO 18
<211> LENGTH: 24
<212> TYPE: DNA
<213> ORGANISM: Artificial
<220> FEATURE:
<223> OTHER INFORMATION: Site-directed mutagenesis primer sequence

<400> SEQUENCE: 18
gcaaatctcc agttcaacgg gggc          24

<210> SEQ ID NO 19
<211> LENGTH: 30
<212> TYPE: DNA
<213> ORGANISM: Artificial
<220> FEATURE:
<223> OTHER INFORMATION: Site-directed mutagenesis primer sequence

<400> SEQUENCE: 19
caaatctcca gtgctacggg ggccagaaac          30

<210> SEQ ID NO 20
<211> LENGTH: 26
<212> TYPE: DNA
<213> ORGANISM: Artificial
<220> FEATURE:
<223> OTHER INFORMATION: Site-directed mutagenesis primer sequence

<400> SEQUENCE: 20
ctccagtgct tcagggggcca gcaacg          26

<210> SEQ ID NO 21
<211> LENGTH: 23

```
<212> TYPE: DNA
<213> ORGANISM: Artificial
<220> FEATURE:
<223> OTHER INFORMATION: Site-directed mutagenesis primer sequence

<400> SEQUENCE: 21
ccagtgcttc aacggccgca agc                                               23

<210> SEQ ID NO 22
<211> LENGTH: 25
<212> TYPE: DNA
<213> ORGANISM: Artificial
<220> FEATURE:
<223> OTHER INFORMATION: Site-directed mutagenesis primer sequence

<400> SEQUENCE: 22
gcttcaacgg ggagcaacga caacc                                             25

<210> SEQ ID NO 23
<211> LENGTH: 20
<212> TYPE: DNA
<213> ORGANISM: Artificial
<220> FEATURE:
<223> OTHER INFORMATION: Site-directed mutagenesis primer sequence

<400> SEQUENCE: 23
cgggggccaa cgacaaccac                                                   20

<210> SEQ ID NO 24
<211> LENGTH: 23
<212> TYPE: DNA
<213> ORGANISM: Artificial
<220> FEATURE:
<223> OTHER INFORMATION: Site-directed mutagenesis primer sequence

<400> SEQUENCE: 24
cgggggccag cgacaaccac ttc                                               23

<210> SEQ ID NO 25
<211> LENGTH: 23
<212> TYPE: DNA
<213> ORGANISM: Artificial
<220> FEATURE:
<223> OTHER INFORMATION: Quantitative PCR primer sequence

<400> SEQUENCE: 25
ggacccaagg actacctcaa ggg                                               23

<210> SEQ ID NO 26
<211> LENGTH: 22
<212> TYPE: DNA
<213> ORGANISM: Artificial
<220> FEATURE:
<223> OTHER INFORMATION: Quantitative PCR primer sequence

<400> SEQUENCE: 26
agggcacctc catctcggaa ac                                                22

<210> SEQ ID NO 27
<211> LENGTH: 26
<212> TYPE: DNA
<213> ORGANISM: Artificial
<220> FEATURE:
<223> OTHER INFORMATION: Quantitative PCR primer sequence

<400> SEQUENCE: 27
```

```
ctccagtgct tcaggggcca gcaacg                                         26

<210> SEQ ID NO 28
<211> LENGTH: 36
<212> TYPE: DNA
<213> ORGANISM: Artificial
<220> FEATURE:
<223> OTHER INFORMATION: Quantitative PCR primer sequence

<400> SEQUENCE: 28
catcgaccag tacctgtatt tcctgaacag aactca                              36

<210> SEQ ID NO 29
<211> LENGTH: 28
<212> TYPE: DNA
<213> ORGANISM: Artificial
<220> FEATURE:
<223> OTHER INFORMATION: Quantitative PCR primer sequence

<400> SEQUENCE: 29
caaacaaatt tccagctcag gagcctcg                                       28

<210> SEQ ID NO 30
<211> LENGTH: 28
<212> TYPE: DNA
<213> ORGANISM: Artificial
<220> FEATURE:
<223> OTHER INFORMATION: Quantitative PCR primer sequence

<400> SEQUENCE: 30
caaatttcca gccaaggagc ctcgaacg                                       28

<210> SEQ ID NO 31
<211> LENGTH: 27
<212> TYPE: DNA
<213> ORGANISM: Artificial
<220> FEATURE:
<223> OTHER INFORMATION: Quantitative PCR primer sequence

<400> SEQUENCE: 31
caagcaaatc tccagctcag gagcttc                                        27

<210> SEQ ID NO 32
<211> LENGTH: 29
<212> TYPE: DNA
<213> ORGANISM: Artificial
<220> FEATURE:
<223> OTHER INFORMATION: Quantitative PCR primer sequence

<400> SEQUENCE: 32
ctccagccaa tcagacggag cttcaaacg                                      29

<210> SEQ ID NO 33
<211> LENGTH: 30
<212> TYPE: DNA
<213> ORGANISM: Artificial
<220> FEATURE:
<223> OTHER INFORMATION: Quantitative PCR primer sequence

<400> SEQUENCE: 33
cagctcccac gactgcaact gtcaatgatc                                     30

<210> SEQ ID NO 34
<211> LENGTH: 24
<212> TYPE: DNA
<213> ORGANISM: Artificial
```

```
<220> FEATURE:
<223> OTHER INFORMATION: Quantitative PCR primer sequence

<400> SEQUENCE: 34
gagcctgcag tccacctaca acgg                                          24

<210> SEQ ID NO 35
<211> LENGTH: 23
<212> TYPE: DNA
<213> ORGANISM: Artificial
<220> FEATURE:
<223> OTHER INFORMATION: Quantitative PCR primer sequence

<400> SEQUENCE: 35
ccgtcgacgg aaacgccaac gcc                                           23

<210> SEQ ID NO 36
<211> LENGTH: 23
<212> TYPE: DNA
<213> ORGANISM: Artificial
<220> FEATURE:
<223> OTHER INFORMATION: Quantitative PCR primer sequence

<400> SEQUENCE: 36
gcaaatctcc gcttcaacgg ggg                                           23

<210> SEQ ID NO 37
<211> LENGTH: 27
<212> TYPE: DNA
<213> ORGANISM: Artificial
<220> FEATURE:
<223> OTHER INFORMATION: Quantitative PCR primer sequence

<400> SEQUENCE: 37
caaatctcca gtgaagcagg tagtacc                                       27

<210> SEQ ID NO 38
<211> LENGTH: 21
<212> TYPE: DNA
<213> ORGANISM: Artificial
<220> FEATURE:
<223> OTHER INFORMATION: Quantitative PCR primer sequence

<400> SEQUENCE: 38
ctccaacggg tcgggaggag c                                             21

<210> SEQ ID NO 39
<211> LENGTH: 33
<212> TYPE: DNA
<213> ORGANISM: Artificial
<220> FEATURE:
<223> OTHER INFORMATION: Quantitative PCR primer sequence

<400> SEQUENCE: 39
caaatctcca cgggactc gggaggagcc acc                                  33

<210> SEQ ID NO 40
<211> LENGTH: 27
<212> TYPE: DNA
<213> ORGANISM: Artificial
<220> FEATURE:
<223> OTHER INFORMATION: Quantitative PCR primer sequence

<400> SEQUENCE: 40
tctccaacgg gacaggagga gccaacc                                       27
```

```
<210> SEQ ID NO 41
<211> LENGTH: 27
<212> TYPE: DNA
<213> ORGANISM: Artificial
<220> FEATURE:
<223> OTHER INFORMATION: Quantitative PCR primer sequence

<400> SEQUENCE: 41
caagcaaatc tccagcacat ctggagg                                      27

<210> SEQ ID NO 42
<211> LENGTH: 29
<212> TYPE: DNA
<213> ORGANISM: Artificial
<220> FEATURE:
<223> OTHER INFORMATION: Quantitative PCR primer sequence

<400> SEQUENCE: 42
ctccaacagc acaggaggat cttcaaatg                                    29

<210> SEQ ID NO 43
<211> LENGTH: 41
<212> TYPE: DNA
<213> ORGANISM: Artificial
<220> FEATURE:
<223> OTHER INFORMATION: Quantitative PCR primer sequence

<400> SEQUENCE: 43
caagcaaatc tccaacagcg actctggagg atcttcaaat g                      41

<210> SEQ ID NO 44
<211> LENGTH: 37
<212> TYPE: DNA
<213> ORGANISM: Artificial
<220> FEATURE:
<223> OTHER INFORMATION: Site-directed mutagenesis primer sequence

<400> SEQUENCE: 44
gcaaatctcc aacgccacag gaggatcttc aaatgac                           37

<210> SEQ ID NO 45
<211> LENGTH: 23
<212> TYPE: DNA
<213> ORGANISM: Artificial
<220> FEATURE:
<223> OTHER INFORMATION: Quantitative PCR primer sequence

<400> SEQUENCE: 45
ggacccaagg actacctcaa ggg                                          23

<210> SEQ ID NO 46
<211> LENGTH: 22
<212> TYPE: DNA
<213> ORGANISM: Artificial
<220> FEATURE:
<223> OTHER INFORMATION: Quantitative PCR primer sequence

<400> SEQUENCE: 46
agggcacctc catctcggaa ac                                           22

<210> SEQ ID NO 47
<211> LENGTH: 8
<212> TYPE: PRT
<213> ORGANISM: Artificial
<220> FEATURE:
<223> OTHER INFORMATION: Mutated VR1 capsid amino acid sequence
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 47

Ser Ser Xaa Ser Asp Gly Ala Ser
1               5

<210> SEQ ID NO 48
<211> LENGTH: 8
<212> TYPE: PRT
<213> ORGANISM: Artificial
<220> FEATURE:
<223> OTHER INFORMATION: Mutated VR1 capsid amino acid sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 48

Ser Ser Xaa Ser Asp Gly Ala Ser
1               5
```

MODIFIED CAPSID PROTEINS FOR ENHANCED DELIVERY OF PARVOVIRUS VECTORS

STATEMENT OF PRIORITY

This application is a divisional of and claims priority to U.S. patent application Ser. No. 16/061,952, filed Jun. 13, 2018, which is a 35 U.S.C. § 371 national phase application of PCT/US2016/066466, filed Dec. 14, 2016, which claims the benefit of U.S. Provisional Application Ser. No. 62/266,941, filed Dec. 14, 2015, the entire contents of which are incorporated by reference herein.

STATEMENT OF FEDERAL SUPPORT

This invention was made with government support under Grant Nos. AI080726, DK084033, HL112761, AI072176, AR064369, and GM007050 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470.710DV_ST25.txt, 10,003 bytes in size, generated on Aug. 20, 2021 and filed via EFS-Web, is provided in lieu of a paper copy. This Sequence Listing is hereby incorporated by reference into the specification for its disclosures.

FIELD OF THE INVENTION

This invention relates to modified parvovirus capsid proteins with enhanced transduction efficiency, viral vectors comprising the same, and methods of using the same for delivery of nucleic acids to a cell or a subject.

BACKGROUND OF THE INVENTION

Various serotypes of recombinant adeno-associated virus (rAAV) are currently being utilized in clinical trials (e.g., rAAV1 for lipoprotein lipase deficiency, rAAV2 for Leber Congenital Amaurosis, rAAV8 for hemophilia). Of these, rAAV1 is considered the best for intramuscular (i.m.) delivery, whether treating muscle disorder directly (e.g., muscular dystrophy) or for conditions that can benefit from the secretion of a therapeutic protein into the bloodstream (e.g., α-1 antitrypsin (AAT) deficiency). A major limitation of this approach has been sub therapeutic levels of transgene expression, despite the administration of high doses of rAAV. For example, while results from rAAV-AAT clinical trials demonstrate dose dependent increases in serum levels of AAT following i.m. injection, in high dose cohorts only ~3% of target AAT expression was achieved. As this cohort required 100 i.m. injections of 1.35 mL each, increasing the dose to the degree necessary for disease correction may not be feasible. Similar observations have been documented for the recently approved rAAV1-based pharmaceutical, Glybera. For rAAV gene augmentation therapy to become a practical choice in cases such as these, improving transduction efficiency in muscle tissue is essential.

Efforts towards increasing transgene expression can be divided into endogenous approaches, wherein the rAAV capsid and transgene themselves are modified to enhance transduction, and/or exogenous approaches, wherein supplementary therapeutics are delivered concurrent to rAAV administration. While exogenous approaches such as immune suppression have improved transduction, the process of integrating new discoveries of rAAV biology into clinical trial design has been the most successful tactic. This is best illustrated with the development of numerous naturally occurring AAV serotypes, and their preferential tissue transduction profiles. This enables correct pairing of AAV serotype to target organ (e.g., clinical trials utilizing i.m. delivery of rAAV became demonstrably more successful when rAAV1 was employed, as opposed to the historically utilized rAAV2). Additionally, serotype-comparative biological and structural analyses have facilitated directed evolution and rational engineering of rAAV, leading to the development of next generation translational vectors.

The capsid structure of most common rAAV serotypes has been resolved. Each contains 60 repeating monomers, comprised of a conserved β-barrel core interspersed with large loops that form the topology of the capsid surface. By comparing the structures of rAAV2 and rAAV4, the least homologous serotypes, a total of nine variable regions (VRs; VRI to VRIX) were defined. The amino acid content of the VRs contributes distinct phenotypes to each serotype, such as receptor binding, antigenic reactivity and transduction efficiency. Comparing the VRs of rAAV2 (the prototypical rAAV) with more efficient muscle transducers, such as rAAV1, led to the first engineered rAAV capsid to enter clinical trial, rAAV2.5 consists of an rAAV2 capsid engrafted with five amino acids from rAAV1, isolated for their contribution to rAAV1's efficiency in muscle. Follow-up studies revealed that only a single amino acid change was needed to markedly enhance rAAV2 efficiency in muscle: namely, insertion of various amino acids following position 264, thereby creating a de novo position 265. Continued pre-clinical studies have suggested that the translatability of rAAV2 is limited by the superior efficiency of serotypes such as rAAV1 and rAAV6, as well as the high prevalence of rAAV2 neutralizing antibodies within the population. These "next generation" serotypes have been augmented further for efficient transduction by modulation of surface amino acids on the capsid backbone.

As rAAV1 has become the top choice for musculoskeletal application, being used in 67% of i.m.-based clinical trials overall and 86% in the past 5 years, improving rAAV1 efficiency is timely to clinical translation. The present invention provides modified capsid proteins that have improved characteristics and are suitable for generating vectors with a wide variety of uses, including gene therapy.

SUMMARY OF THE INVENTION

This study dissected rAAV capsid architecture to develop an engineering strategy designed to improve muscle transduction. Contrary to rAAV2 265 insertion mutants, the deletion of position 265 from the rAAV1 capsid provided the highest level of enhancement for both transgene delivery and expression in muscle tissue. Furthermore, through homology modeling and mutational analysis, two regions of the capsid were identified that appear to work together allosterically to control transduction efficiency in rAAV6 and rAAV2. The results provide a mechanism of regional destabilization in the VR1 loop due to the destruction of hydrogen bonding patterns. This discovery allowed for rational mutation of these additional serotypes in order to enhance transduction efficiency by at least an order of magnitude in each case. Furthermore, expression of the clinical AAT transgene in the chimera rAAV serotypes increased expression by up to 12.5-fold over parental rAAV1, supporting the use of these constructs in clinical trials. This study validates a rational design approach using structural modeling and molecular dissection of the rAAV capsid for improved delivery reagents better suited for translational studies.

One aspect of the invention relates to a parvovirus capsid protein comprising a capsid protein amino acid sequence from an AAV serotype or any other parvovirus with an icosahedral capsid structure of T=1, wherein the variable region 1 (VR1) loop comprising amino acid residues 258 to 272 of AAV1 capsid protein or the corresponding amino acid residues from another AAV or parvovirus capsid protein is modified by deletion and/or substitution of one or more amino acid residues to cause regional destabilization within the loop due to the targeted destruction of hydrogen bonding patterns orchestrated by the residues, wherein the capsid protein comprising the modification provides to a virus vector comprising the capsid protein increased transduction efficiency relative to a virus vector comprising a capsid protein that does not contain the modification.

An additional aspect of the invention relates to the capsid protein of the invention, wherein the capsid protein comprises an amino acid sequence from an AAV serotype or other parvovirus that binds to heparin sulfate, wherein one or more amino acid residues that mediate binding of the capsid protein to heparin sulfate are substituted and/or deleted, wherein binding of the capsid protein to heparin sulfate is substantially reduced.

A further aspect of the invention relates to an AAV capsid protein comprising an amino acid sequence from an AAV3a, AAV3b, AAV6, or AAV8 serotype, wherein one or more amino acid residues that mediate binding of the capsid protein to heparin sulfate are substituted and/or deleted, wherein binding of the capsid protein to heparin sulfate is substantially reduced.

An additional aspect of the invention relates to an AAV capsid protein comprising an amino acid sequence from an AAV2, AAV3a, or AAV3b serotype, wherein the capsid protein comprises an insertion of one or more amino acid residues immediately following residue 264 of AAV2 capsid protein or the corresponding residue of AAV3a or AAV 3b capsid protein, and one or more amino acid residues that mediate binding of the capsid protein to heparin sulfate are substituted and/or deleted, wherein binding of the capsid protein to heparin sulfate is substantially reduced; wherein the capsid protein provides to a virus vector comprising the capsid protein increased transduction efficiency relative to a virus vector comprising an unmodified capsid protein.

A further aspect of the invention relates to a polynucleotide encoding the capsid protein of the invention, a parvovirus capsid comprising the capsid protein of the invention, a virus vector comprising the capsid protein of the invention, and a pharmaceutical composition comprising the virus vector of the invention.

Another aspect of the invention relates to a method of delivering a nucleic acid to a cell, the method comprising contacting the cell with the virus vector or the pharmaceutical composition of the invention under conditions sufficient for the nucleic acid to enter the cell.

A further aspect of the invention relates to method of delivering a nucleic acid to a subject, the method comprising administering to the subject the virus vector or the pharmaceutical composition of the invention.

Another aspect of the invention relates to method of delivering a nucleic acid to a subject, the method comprising administering to the subject a cell that has been contacted with the virus vector or the pharmaceutical composition of the invention under conditions sufficient for the nucleic acid to enter the cell.

An additional aspect of the invention relates to a method of producing a recombinant parvovirus particle, comprising providing to a cell permissive for parvovirus replication: (a) a recombinant parvovirus template comprising (i) a heterologous nucleic acid, and (ii) at least one inverted terminal repeat; and (b) a polynucleotide comprising replication protein coding sequence(s) and sequence(s) encoding the capsid protein of the invention; under conditions sufficient for the replication and packaging of the recombinant parvovirus template; whereby recombinant parvovirus particles are produced in the cell.

These and other aspects of the invention are set forth in more detail in the description of the invention below.

BRIEF DESCRIPTION OF THE DRAWINGS

FIGS. 4A-4C show the effect of capsid:heparin interactions on the transduction phenotype of 265 mutation. (A) Transgene expression 7 dpi of rAAV2 capsid mutants into the GC. (B) Pymol depiction of the rAAV6 capsid with residues T265 (purple), K531 (orange) and R585 (blue) denoted, in the context of the 3-fold axis of symmetry. Dashed circle represents general outline of heparin binding footprint. (C) Transgene expression of rAAV2 and rAAV1 constructs injected into GC following preincubation in either a saline or heparin sulfate solution. All data represents n=4 per group.

FIGS. 5A-5D show heparin affinity chromatography elution profiles of rAAV2 and rAAV6 constructs used in this study. rAAV2 (A, B) and rAAV6 (C, D) constructs used in this study were incubated with heparin-conjugated agarose beads and then eluted from beads using increasingly stringent NaCl washes. Elution profiles were collected by quantifying the number of viral genomes present in each eluted fraction using RT-qPCR. Experiments were repeated in triplicate; one representative chromatogram is shown per group.

Figure 6:
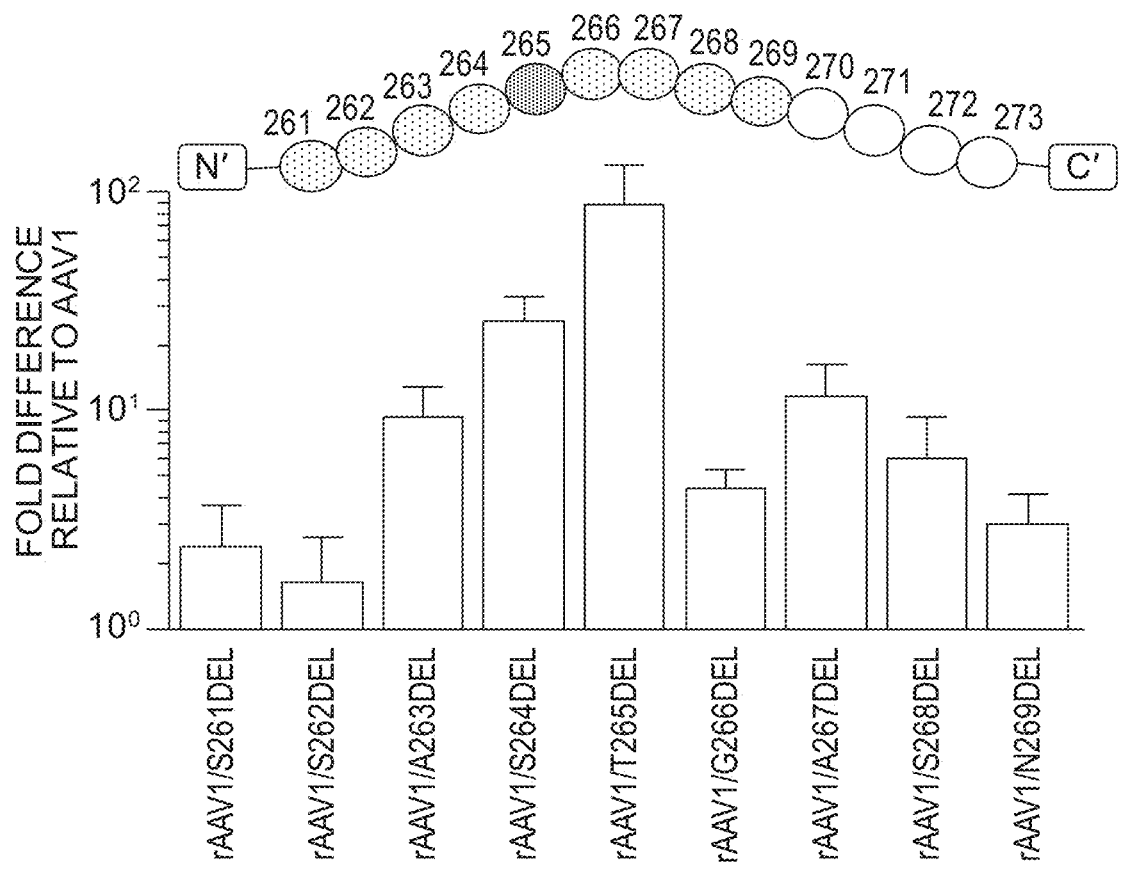

FIG. 6 shows transgene expression of VR1 deletion scanning mutants in the rAAV1 capsid. Single deletion mutations were created in the VR1 loop of the rAAV1 capsid, and constructs were injected into mouse GC at a dose of 1e10vg. Transgene expression is depicted as fold difference relative to that measured following injection of rAAV1. Cartoon above graph depicts residues that were mutated for this study in light grey, with position 265 depicted in dark grey. The location of N- and C-terminal beta sheets surrounding VR1 is also shown. Data is representative of n=4 per group.

Figure 7:
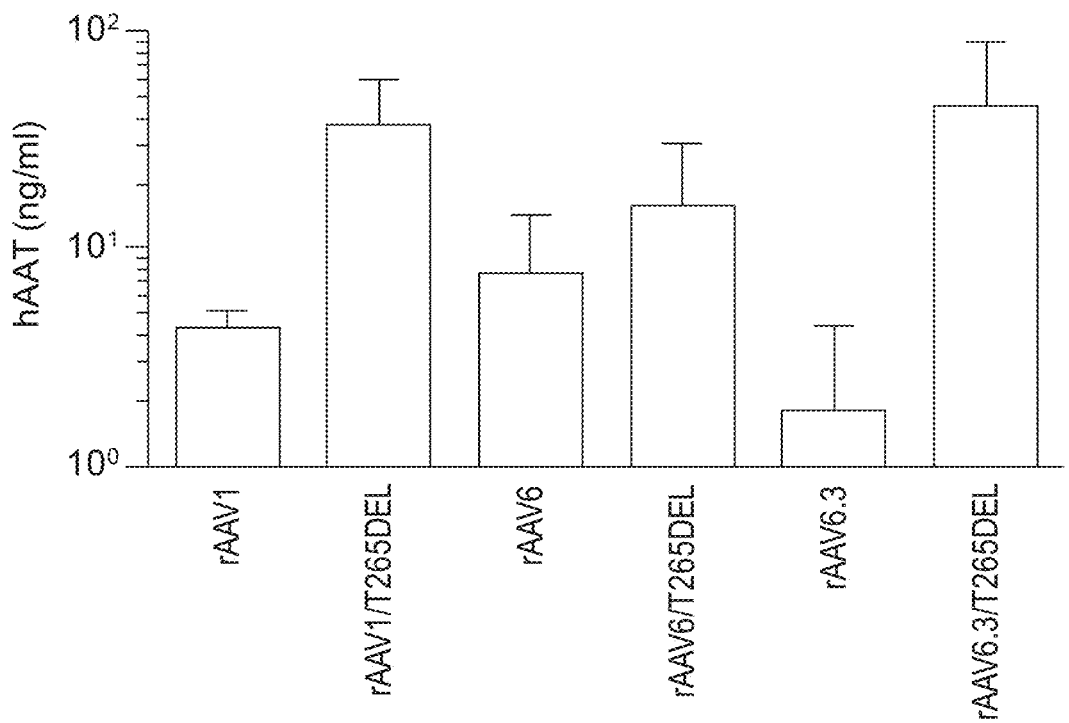

FIG. 7 shows serum concentration of hAAT following i.m. injection of rAAV1 and rAAV6 constructs. rAAV1 and rAAV6 capsid packaging an hAAT transgene were injected into GC muscle at a dose of 1e10vg. 5 weeks post injection, serum was collected and ELISA used to determine quantities of hAAT protein within the blood. Data represents n=4 per group.

FIG. 8 shows hydrogen bonds in the VR1 region of rAAV1 and rAAV6 capsids. Atom pairs involved in hydrogen bond formation were calculated for rAAV1 and rAAV6 crystallographic coordinates using MolProbity all atom contact analysis and visualized using KiNG graphics program. Residues comprising the VR1 loop are labeled. Hydrogen bonds generated from residue 265 are visualized using green dots and are indicated by arrows. VR1 side chains are colored orange and the protein backbone is colored yellow.

Figure 9:
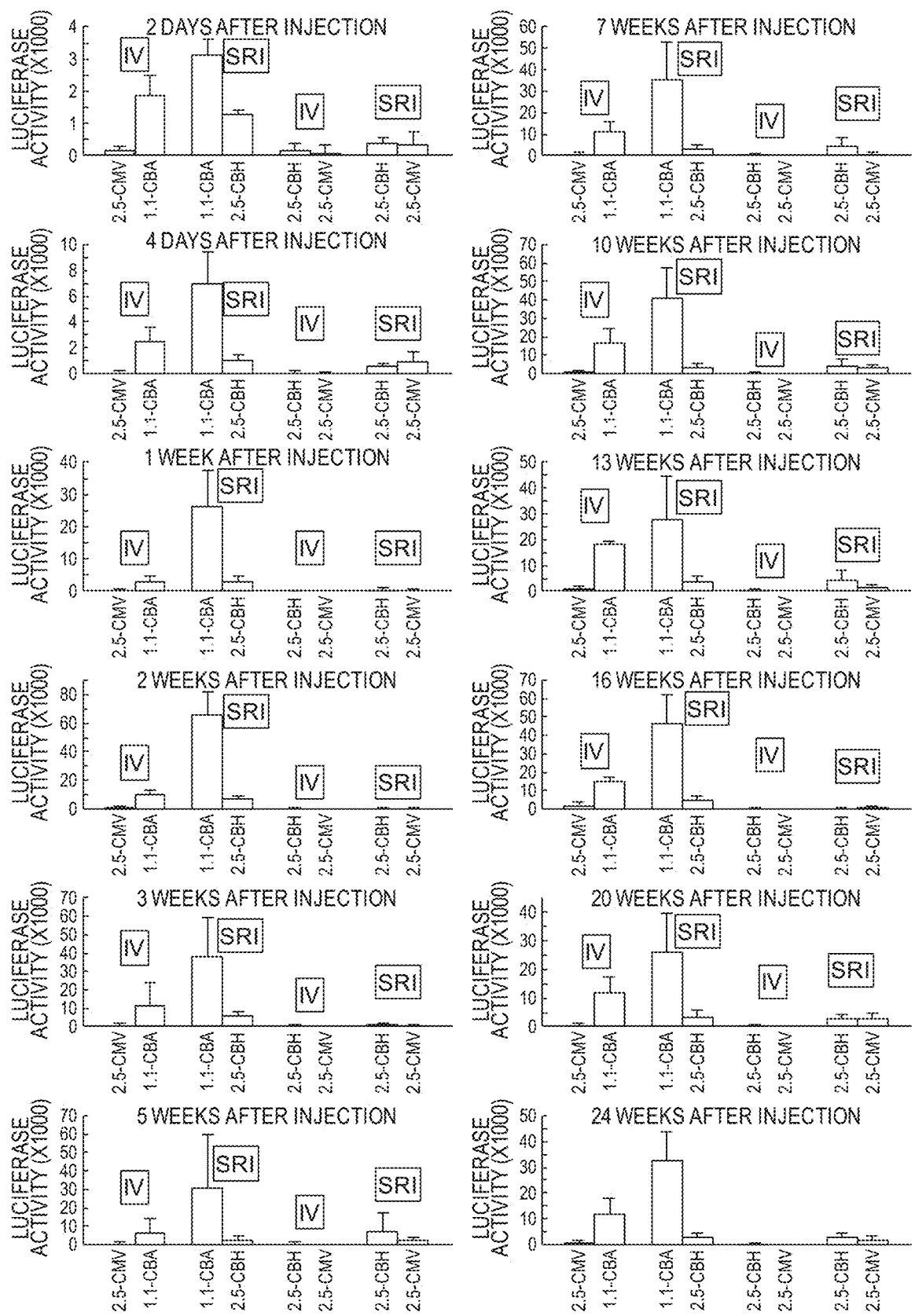

FIG. 9 shows transgene expression after injection of rAAV1 and rAAV6 constructs into the eye.

Figure 10:
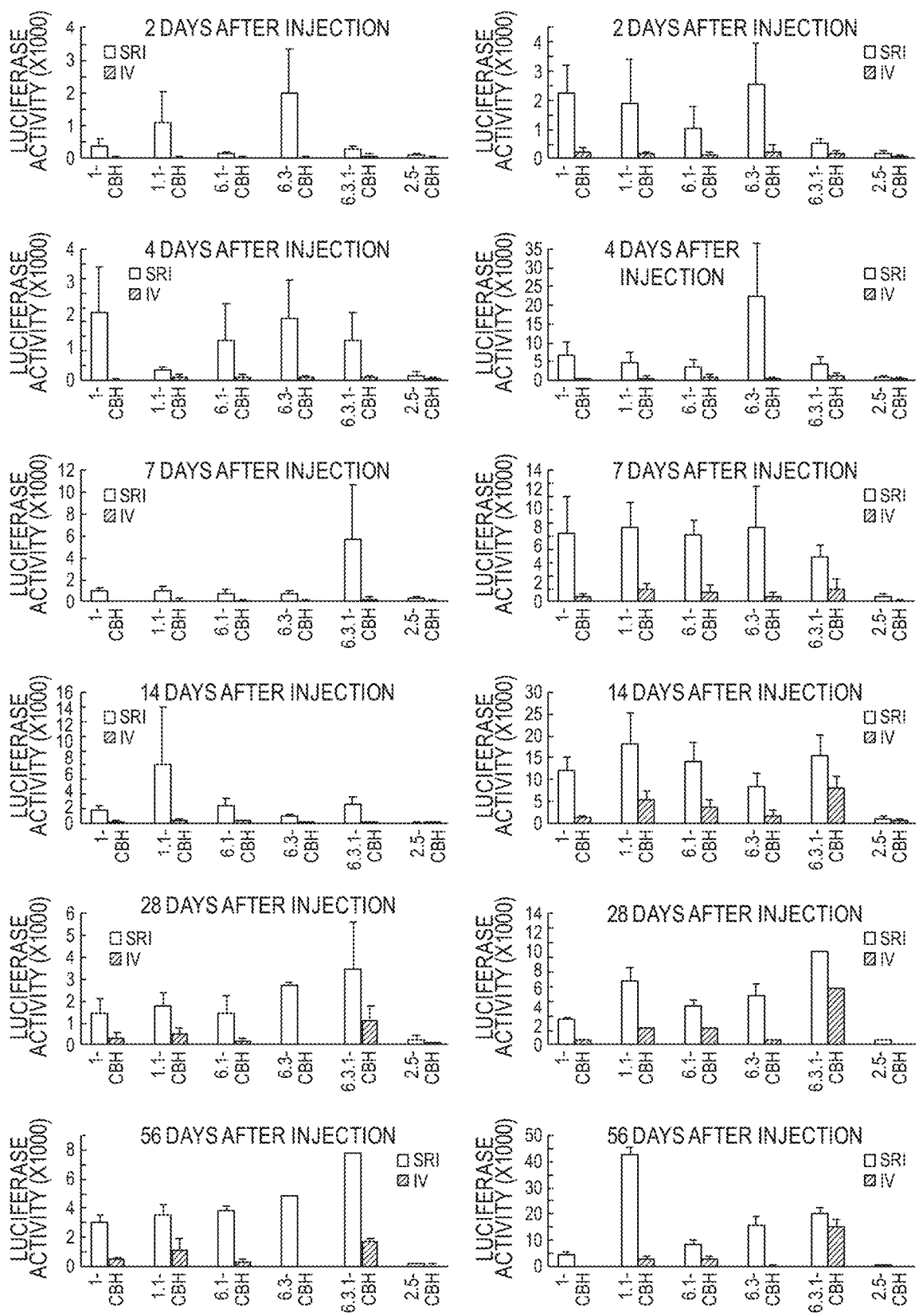
Figure 11A:
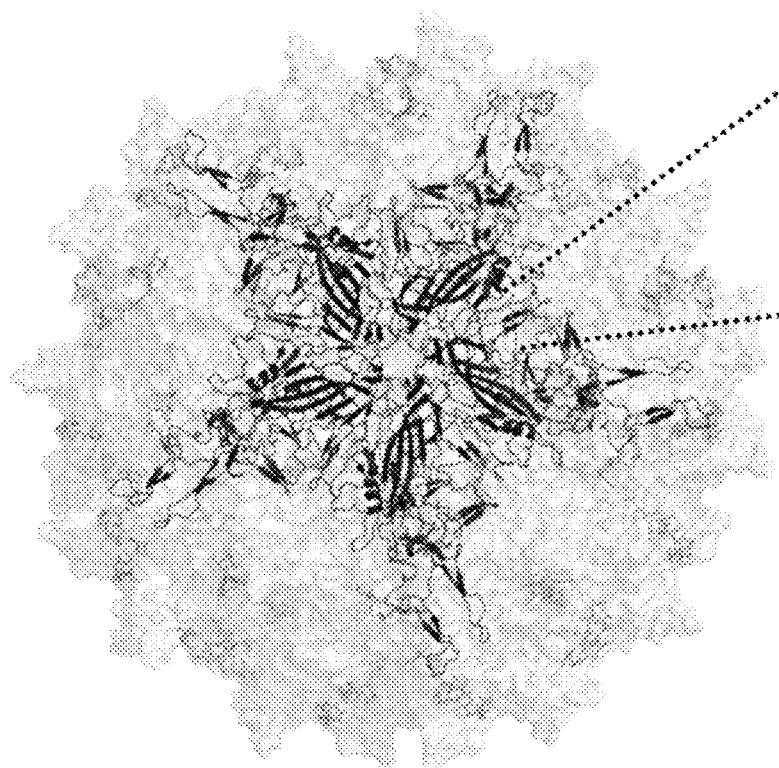
Figure 11B:
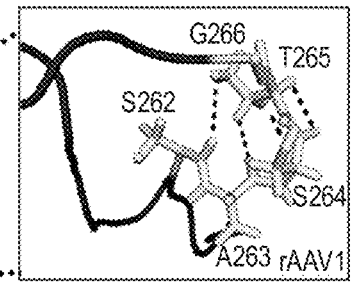
Figure 11C:
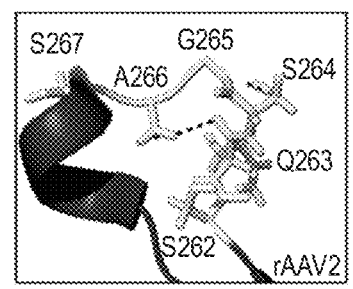
Figure 11D:
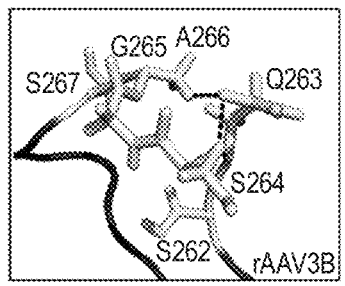
Figure 11E:
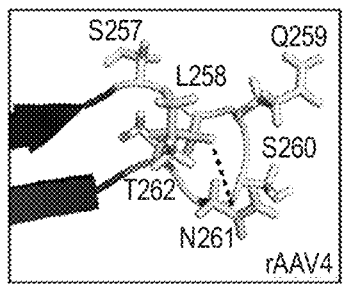
Figure 11F:
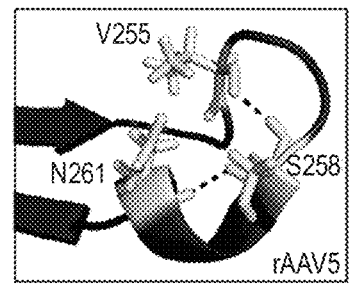
Figure 11G:
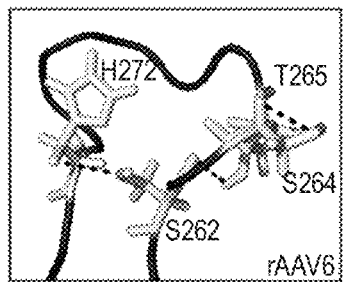
Figure 11H:
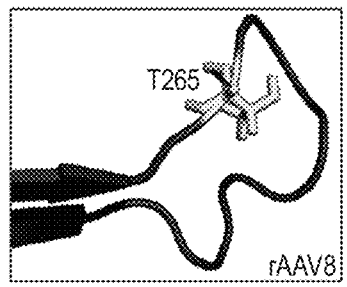
Figure 11I:
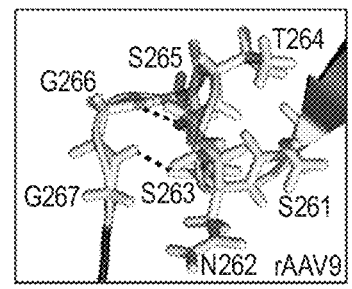
Figure 12A:
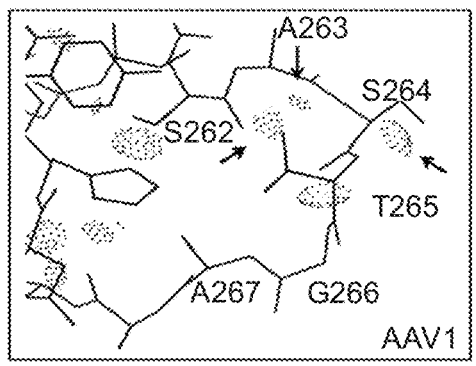
Figure 12E:
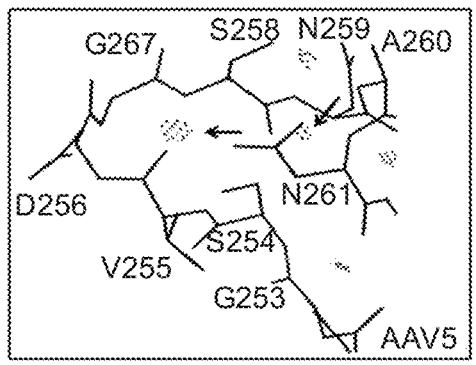
Figure 12B:
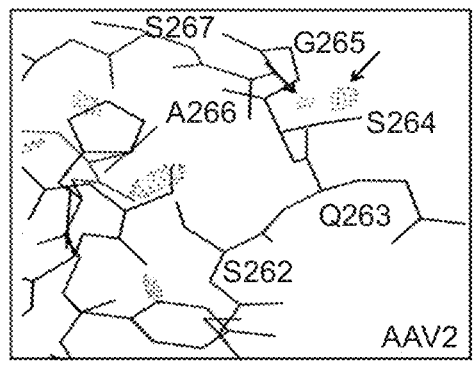
Figure 12F:
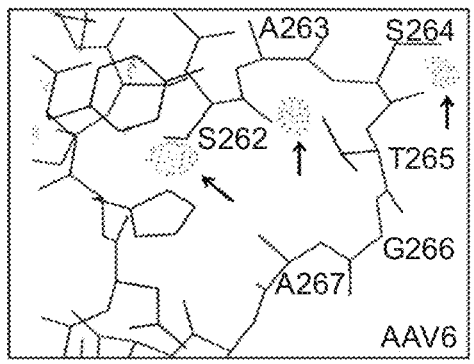
Figure 12C:
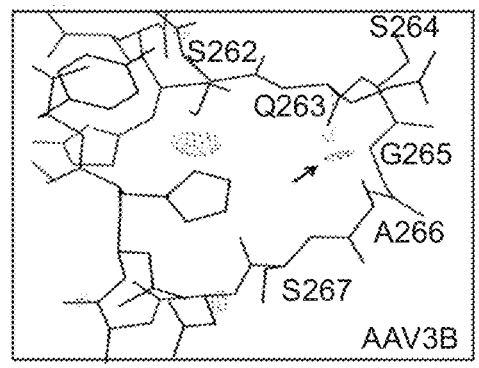
Figure 12G:
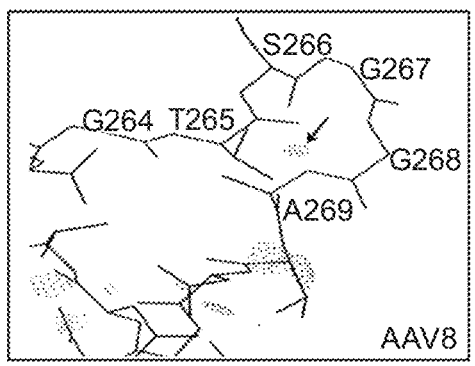
Figure 12D:
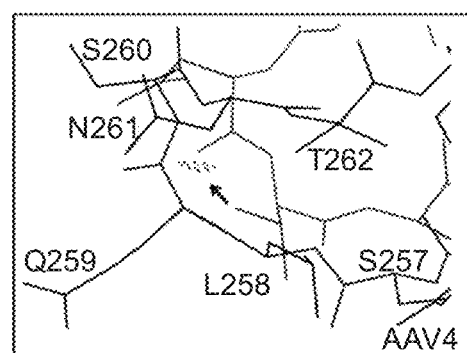
Figure 12H:
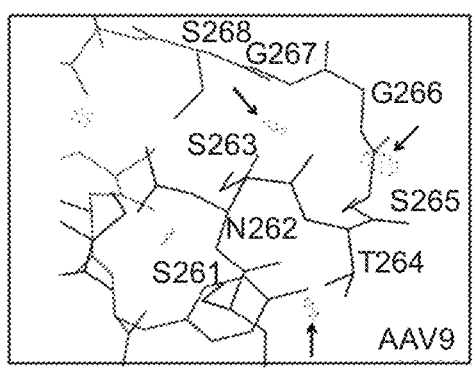

FIG. 10 shows transgene expression after injection of rAAV1 and rAAV6 constructs into the eye.

FIGS. 11A-11I show VR1 hydrogen bonding networks visualized by KiNG display software (A). Protein main chains are depicted in orange, side chains in light green. Hydrogen bonds are shown as dark green clouds, with arrows indicating hydrogen bonds present in VR1. VR1 residues are labeled. In panel (B), the following bonds are highlighted for rAAV1: HG1 T265 to O S262; O A263 to HG1 T265; OG S264 to H T265. In panel (C), the following bonds are highlighted for rAAV2: OG S264 to H G265; H A266 to O Q263. In panel (D), the following bonds are highlighted for rAAV3b: O Q263 to H A266; O Q263 to H G265. In panel (E), the following bonds are highlighted for rAAV4: O L258 to H N261. In panel (F), the following bonds are highlighted for rAAV5: H S258 to O V255; O S258 to H N261. In panel (G), the following bonds are highlighted for rAAV6: O S264 A to HG S264 A; HG1 T265 to O S262; OG S262 to HD1 H272. In panel (H), the following bonds are highlighted for rAAV8: HG1 T265 to O T265. In panel (I), the following bonds are highlighted for rAAV9: HG S265 to O S265; H G267 to O S263.

FIGS. 12A-12H show VR1 hydrogen bond networks in various rAAV serotypes. Pymol images are focused on capsid loop VR1. Dashed lines represent hydrogen bonds present in the crystal structures of rAAV1 (PDB ID, 3NG9), rAAV2 (PDB ID, 1LP3), rAAV3b (PDB ID, 3KIC), rAAV4 (PDB ID, 2G8G), rAAV5 (PDB ID, 3NTT), rAAV6 (PDB ID, 3OAH), rAAV8 (PDB ID, 2QAO), and rAAV9 (PDB ID, 3UX1). VR1 amino acids participating in hydrogen bond networks are depicted. as sticks and colored green. Amino acids that were mutated for this study are colored cyan. In rAAV1 (A), bonds are shown between residues T265 and S262, T265 and A263, T265 and S264, and S264 and G266. In rAAV2 (B), bonds are shown between residues S264 and G265, and Q263 and A266. In rAAV3b (C), bonds are shown between residues Q263 and A266, and Q263 and G265. In rAAV4 (D), bonds are shown between residues L258 and N261. In rAAV5 (E), bonds are shown between residues S258 and V255, and S258 and N261. In rAAV6 (F), bonds are shown between residues T265 and S262, and S262 and H272. In rAAV8 (G), bonds are shown between residues T265 and T265 (residue hydrogen bonds to itself). In rAAV9 (H), bonds are shown between residues S263 and G267, and S265 and S265 (residue hydrogen bonds to itself).

FIGS. 13A-13F show biodistribution of rAAV1 and rAAV6 capsids bearing VR1 deletion mutations. Live-animal bioluminescent imaging of rAAV1 (A) and rAAV6 (D) capsids at 9 days post tail vein injections of 1e11 vector genomes per construct. At 10 dpi, indicated organs were harvested, lysed and homogenized, and luciferase expression and total protein content of lysate quantified (B, E). Values are shown in relative light units per milligram total protein (RLU/mg). An indicated subset of organs was further processed via qPCR (C, F) to determine number of vector genomes per cell genomes (vg/cg). Each data point represents n=3; images are of one representative mouse per group. Error bars reflect standard deviation.

FIGS. 14A-14I show biodistribution of rAAV7, rAAV8, and rAAV9 capsids bearing VR1 deletion mutations. Live-animal bioluminescent imaging of rAAV7 (A), rAAV8 (D), and rAAV9 (G) capsids at 9 days post tail vein injections of 1e11 vector genomes per construct. At 10 dpi, indicated organs were harvested, lysed and homogenized, and luciferase expression and total protein content of lysate quantified (B, E, H). Values are shown in relative light units per milligram total protein (RLU/mg). An indicated subset of organs was further processed via qPCR (C, F, I) to determine number of vector genomes per cell genomes (vg/cg). Each data point represents n=3; images are of one representative mouse per group. Error bars reflect standard deviation.

FIGS. 15A-15D show qualitative biodistribution of VR1 deletion mutant capsids in serotypes rAAV2 and rAAV3b. In panels (A) and (B), 1e11vg of each of the indicated constructs was administered via the tail vein. Mice were imaged at 10 dpi. In panels (C) and (D), 5e11vg of each of the indicated constructs was administered via the tail vein. Mice were imaged at 10 dpi. In all cases N=3 was evaluated; one representative mouse from each group is shown.

Figures 16A, 16B, 16C:
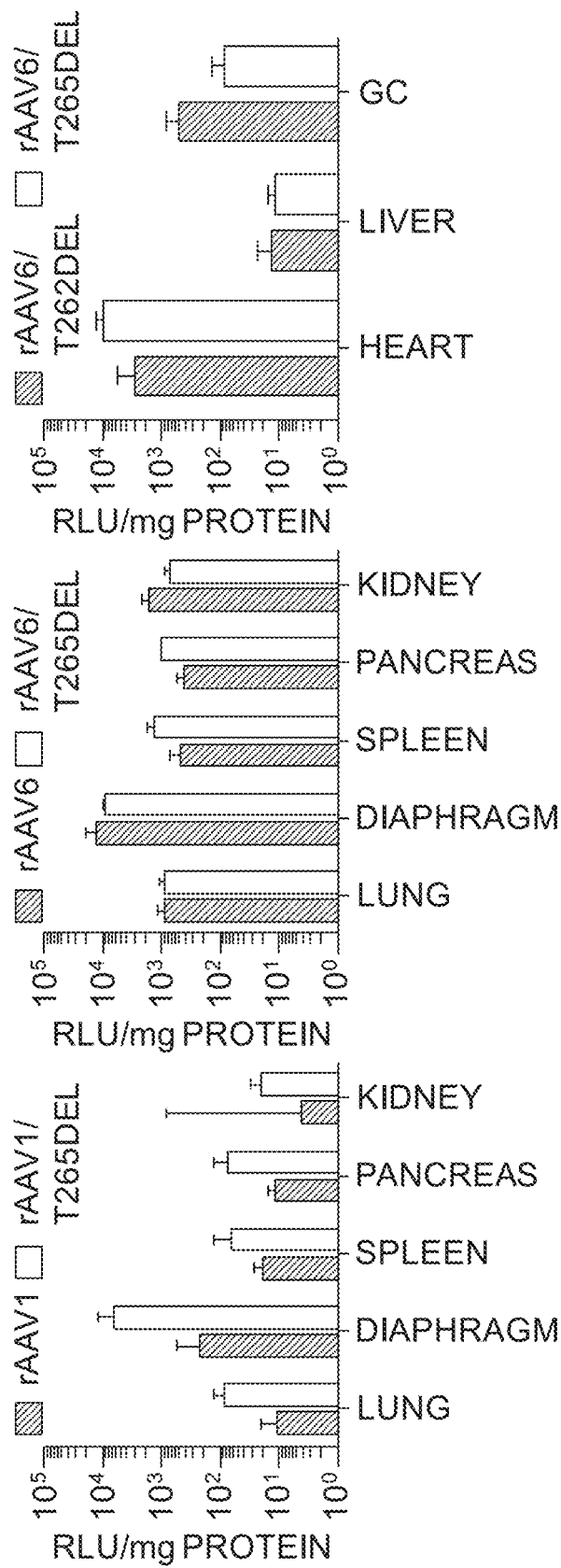

FIGS. 16A-16C show quantitative biodistribution for VR1 deletion mutant rAAV1 and rAAV6 capsids. Panels (A) and (B) depict luciferase expression via average RLU/mg protein for visceral organs following tail vein injection of 1e11vg of the indicated constructs. Panel (C) compares luciferase expression via average RLU/mg protein between rAAV6/T262del and rAAV6/T265del in heart, liver and GC. N=3; error bars represent standard deviation.

FIGS. 17A-17D show quantitative and qualitative biodistribution of VR1 deletion mutant rAAV7, rAAV8, and rAAV9 capsids. Panels (A), (B), and (C) depict luciferase expression via average RLU/mg protein for visceral organs following tail vein injection of 1e11vg of the indicated constructs. In panel (D) mice were injected via the tail vein with 1e11vg per indicated construct and imaged at 10 dpi. N=3 for all experiments error bars represent standard deviation. In panel (D) one representative mouse from each group is shown.

FIGS. 18A-18L show biodistribution of rAAV1, rAAV2, rAAV3b, and rAAV6 capsids bearing VR1 insertion/substitution mutations. Live-animal bioluminescent imaging of rAAV2 (A), rAAV3b (D), rAAV1 (G), and rAAV6 (J) capsids at 9 days post tail vein injections of 1e11 vector genomes per construct. At 10 dpi, indicated organs were harvested, lysed and homogenized, and luciferase expression and total protein content of lysate quantified (B, E, H, K). Values are shown in relative light units per milligram total protein (RLU/mg). An indicated subset of organs was further processed via qPCR (C,F, I, L) to determine number of vector genomes per cell genomes (vg/cg). Each data point represents n=3; images are of one representative mouse per group. Error bars reflect standard deviation.

FIGS. 19A-19D show quantitative biodistribution for VR1 265D mutant rAAV1, rAAV2, rAAV3b, and rAAV6 capsids. Panels (A), (B), (C) and (D) depict luciferase expression via average RLU/mg protein for visceral organs following tail vein injection of 1e11vg of the indicated constructs. N=3; error bars represent standard deviation.

Figure 20A:
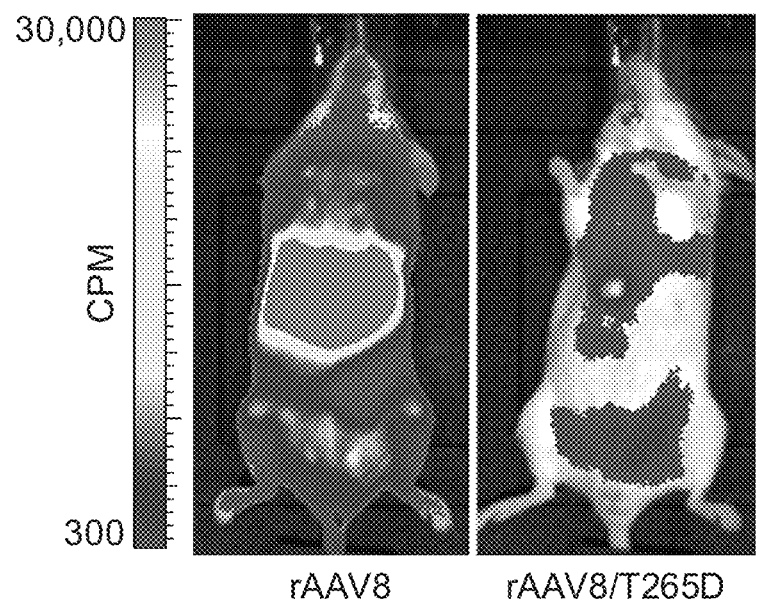
Figure 20B:
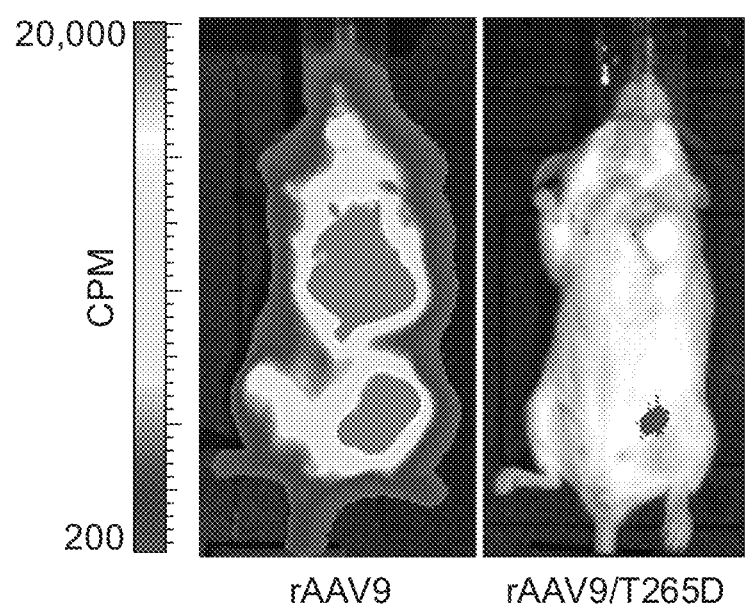
Figure 21A:
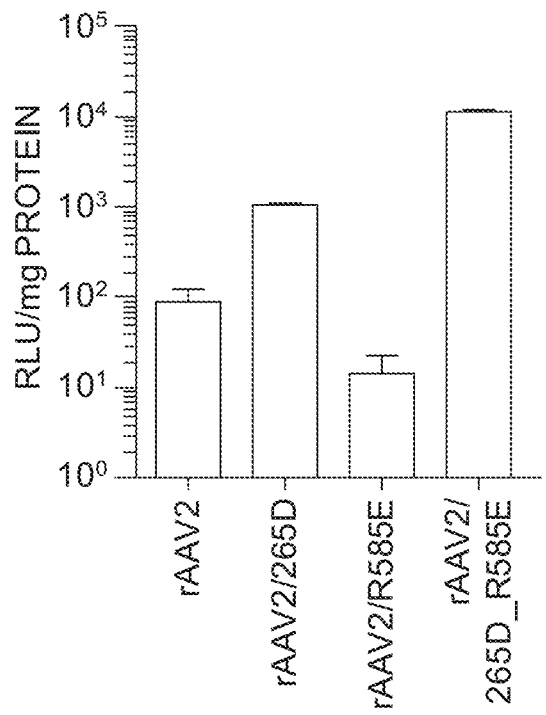
Figure 21B:
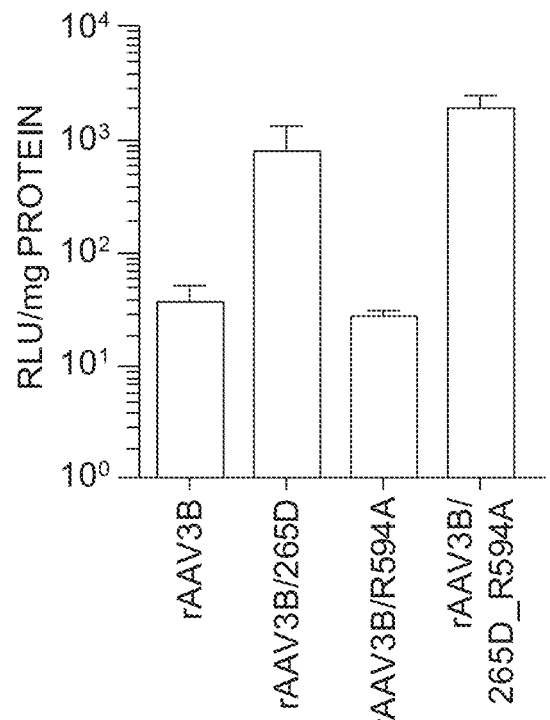
Figure 21C:
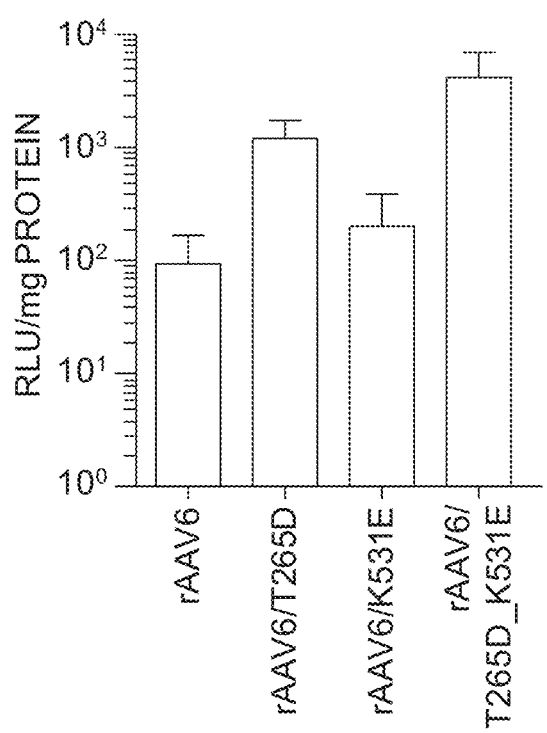
Figure 21D:
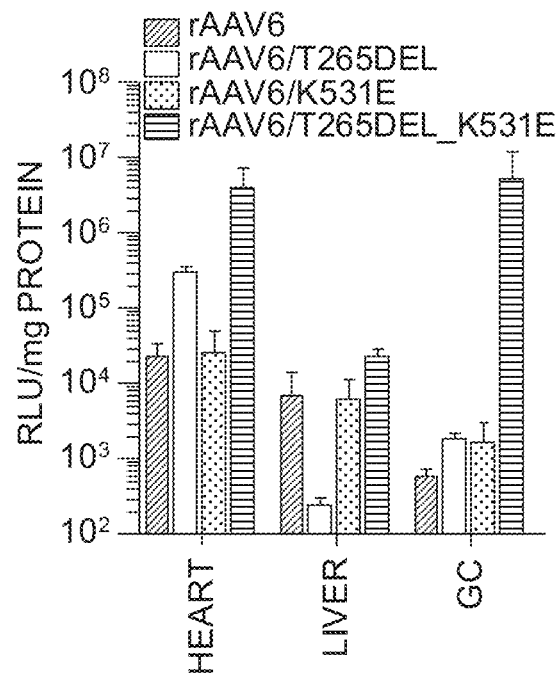
Figure 22A:
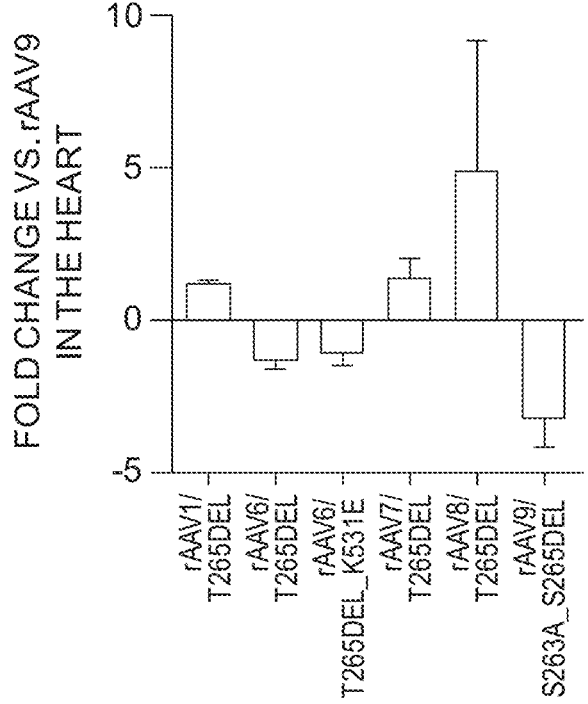
Figure 22C:
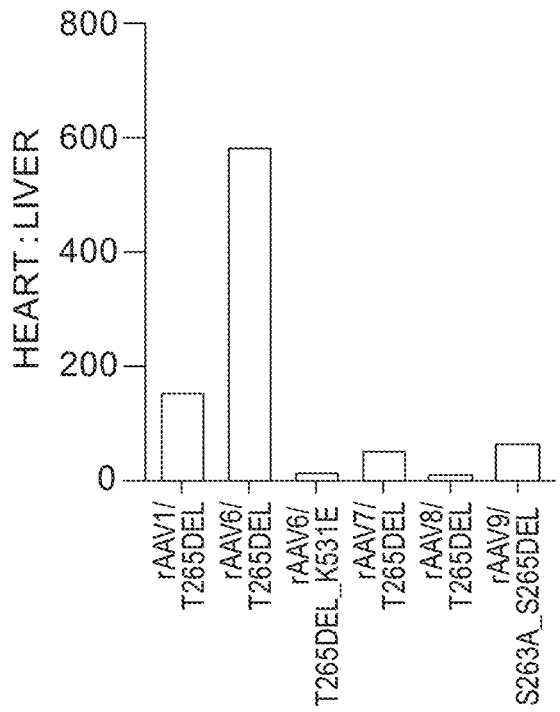
Figure 22B:
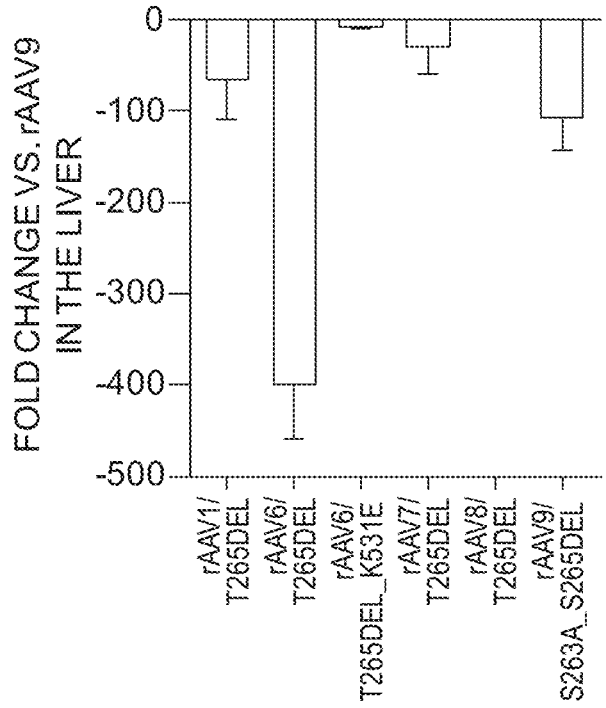
Figure 22D:
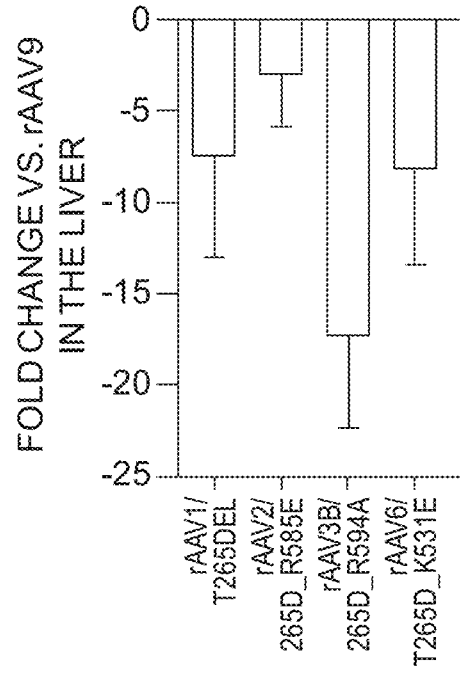

FIGS. 20A-20B show qualitative biodistribution of 265D mutant rAAV8 and rAAV9 capsids. In panels (A) and (B), 1e11vg of each of the indicated constructs was administered via the tail vein. Mice were imaged at 10 dpi. In all cases N=3 was evaluated; one representative mouse from each group is shown.

FIGS. 21A-21D show the impact of capsid heparin binding ability on transduction efficiency of capsids bearing VR1 insertion/substation mutations. Ex vivo luciferase assay results on liver samples taken 10 dpi from mice injected with 1e11vg of an rAAV2 capsid subset (A) including 265D, heparin-null, and 265D heparin null combination mutants; an rAAV3b capsid subset (B) including 265D, heparin-null, and 265D heparin null combination mutants; and an rAAV6 capsid subset (C) including 265D, heparin-null, and 265D heparin null combination mutants. Ex vivo luciferase assay results on heart, liver, and GC samples taken 10 dpi from mice injected with 1e11vg of an rAAV6 capsid subset (D) including T265del, heparin-null, and T265del heparin-null combination mutants. Data represent relative light units normalized per mg of protein analyzed (RLU/mg). Each data point represents n=3; error bars reflect standard deviation.

FIGS. 22A-22D show the comparison of VR1 mutant to wild-type capsid transduction efficiency in cardiac and hepatic tissues. Ex vivo luciferase assay results on tissue samples taken from the heart (A) and liver (B) at 10 dpi of 1e11vg of a panel of VR1 deletion mutant capsids. Data represented as fold-change relative to values obtained for rAAV9, after measuring relative light units per mg of protein analyzed. Ratio of heart to liver transduction (C) of organs analyzed in A and B. Ex vivo luciferase assay results on liver tissue samples (D) taken at 10 dpi of 1e11vg of a panel of 265D mutant capsids. Data represented as fold-change relative to values obtained for rAAV8 after measuring relative light units per mg of protein analyzed. Each data point represents n=3; error bars reflect standard deviation.

Figure 23A:
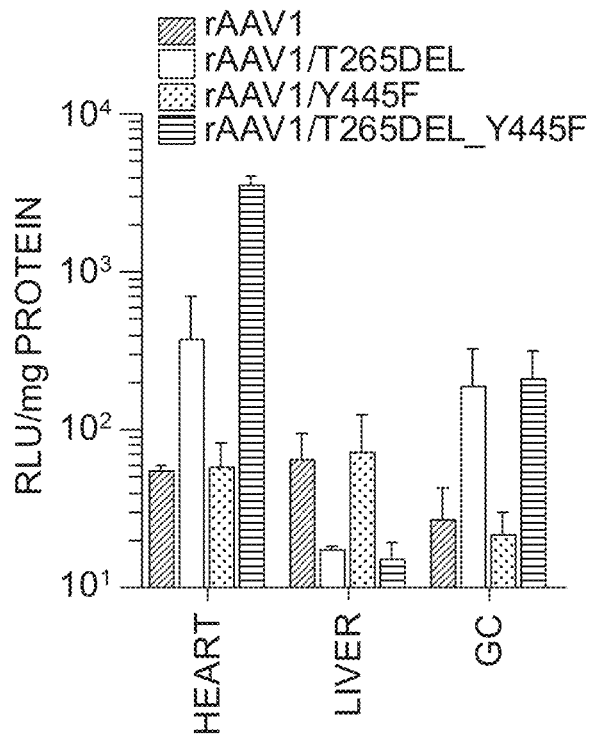
Figure 23B:
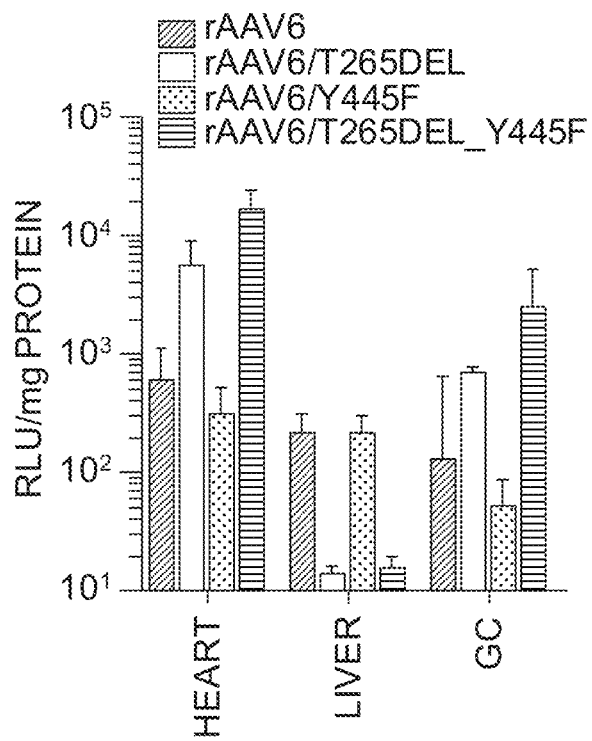

FIGS. 23A-23B show the transduction efficiency of rAAV1 and rAAV6 capsids bearing VR1 mutations in conjunction with tyrosine-to-phenylalanine mutations. Ex vivo luciferase assay results on a panel of heart, liver, and GC tissues taken from a panel of rAAV1 capsids (A) bearing VR1 deletion mutations alone and in conjunction of Y445F mutations, and from a panel of rAAV6 (B) capsids with the equivalent mutations. Data represent relative light units normalized per mg of protein analyzed (RLU/mg). Tissue samples were taken at 10 dpi of 1e11vg per construct. Each data point represents n=3; error bars reflect standard deviation.

Figure 24:
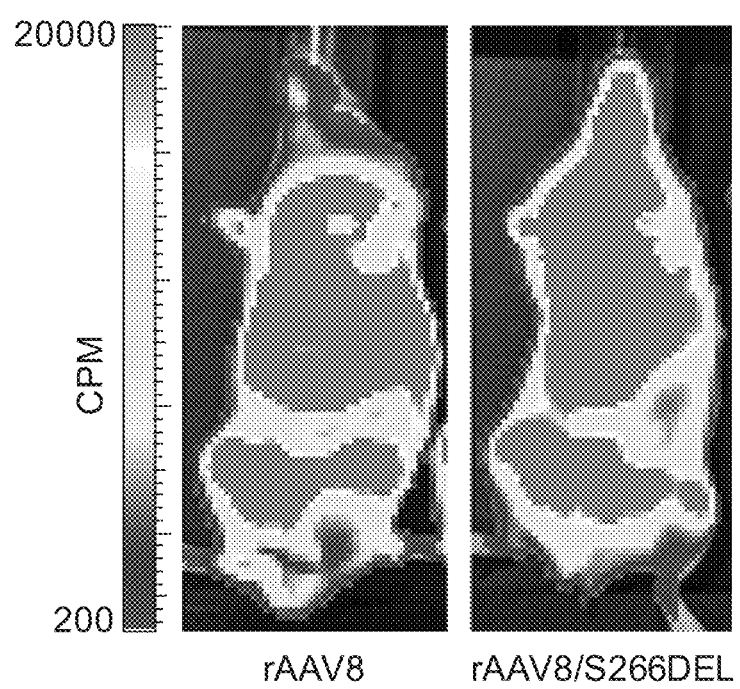

FIG. 24 shows qualitative biodistribution of rAAV8 and rAAV8/S266del capsids. 1e11vg of each of the indicated constructs was administered via the tail vein. Mice were imaged at 10 dpi. In all cases N=3 was evaluated; one representative mouse from each group is shown.

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual*, 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL. 2nd Ed. (Cold Spring Harbor, N.Y., 1989); AUSUBEL et al., CURRENT PROTOCOLS IN MOLECULAR BIOLOGY (Green Publishing Associates. Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention e.g., rAAV replication). See, In re Herz, 537 F.2d. 549. 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in transduction activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus,* and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1).

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by parvovirus or AAV refers to parvovirus/AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |

TABLE 1-continued

| Complete Genomes | GenBank Accession Number |
|---|---|
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |

TABLE 1-continued

| Complete Genomes | GenBank Accession Number |
|---|---|
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Nail. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al. J. Mol. Evol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wust1/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucleic Acids Res. 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s)

relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirely). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbial. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. FIG. 24 provides examples of synthetic ITRs contemplated by the present invention.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

TABLE 2-continued

| Amino Acid Residue | Abbreviation | |
| --- | --- | --- |
| | Three-Letter Code | One-Letter Code |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

Amino Acid Residue Derivatives

| Modified Amino Acid Residue | Abbreviation |
| --- | --- |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense imitations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

Modified Parvovirus Capsid Proteins

The present invention provides modified parvovirus capsid proteins that provide enhanced tissue transduction capabilities and/or modified tissue specificities and can be used to prepare parvovirus vectors for efficient delivery of nucleic acids to cells. The inventors have discovered that destabilization of the variable region 1 (VR1) loop of the capsid protein by disruption of hydrogen bonding between amino acid residues results in enhanced cell transduction and/or modified tissue specificities.

One aspect of the invention relates to a parvovirus capsid protein comprising a capsid protein amino acid sequence from an AAV serotype or any other parvovirus with an icosahedral capsid structure of T=1. wherein the variable region 1 (VR1) loop comprising amino acid residues 258 to 272 of AAV1 capsid protein or the corresponding amino acid residues from another AAV or parvovirus capsid protein is modified by deletion and/or substitution of one or more amino acid residues to cause regional destabilization within the loop due to the targeted destruction of hydrogen bonding patterns orchestrated by the residues, wherein the capsid protein comprising the modification provides to a virus vector comprising the capsid protein increased transduction efficiency and/or modified tissue specificity relative to a virus vector comprising a capsid protein that does not contain the modification.

AAV serotypes are well known in the art and are described above in Table 1. AAV serotypes have an icosahedral capsid structure of T=1.

There are 8 genera wider the subfamily Parvoviridae that are capable of infecting vertebrates, and all are distinguished by capsids bearing T=1 icosahedral symmetry. Parvoviridae include, without limitation, the following viruses.

1.) Amdoparvovirus (species include: Aleutian mink disease virus, Gray fox amdovirus)
2.) Aveparvovirus (species include: Aveparvovirus)
3.) Bocaparvovirus (species include: Carnivore bocaparvovirus 1-3; Pinniped bocaparvovirus 1 and 2; Primate bocaparvovirus 1 and 2; Ungulate bocaparvovirus 1-5)
4.) Copiparvovirus (species include: Copiparvovirus)
5.) Dependoparvovirus (species include: Adeno-associated dependoparvovirus A; Adeno-associated dependoparvovirus B; Anseriform dependoparvovirus 1; Avian dependoparvovirus 1; Chiropteran dependoparvovirus 1; Pinniped dependoparvovirus 1; Squamate dependoparvovirus 1)
6.) Erythroparvovirus (species include: Primate erythroparvovirus 1-4; Rodent erythroparvovirus 1; Ungulate erythroparvovirus 1)
7.) Protoparvovirus (Species include: Carnivore protoparvovirus 1; Rodent protoparvovirus 1 and 2; Ungulate parvovirus 1)
8.) Tetraparvovirus (Species include: Chiropteran tetraparvovirus 1; Primate tetraparvovirus 1; Ungulate tetraparvovirus 1-4)

Capsid protein sequences are known in the art and are available in sequence databases such as GenBank. The amino acid residue numbers used herein with respect to the capsid protein from AAV1, AAV2, AAV3b, AAV4, AAV5, AAV6, AAV7, AAV8, and AAV9 refer to the sequences as disclosed in GenBank Accession Nos. as listed in Table 1.

The VR1 region is an art-recognized portion of the capsid protein sequence of AAV serotypes and parvoviruses with an icosahedral capsid structure of T=1. The loop that makes up the VR1 region consists essentially of amino acid residues 258 to 272 of AAV1 or the corresponding amino acid residues from another AAV or parvovirus. Because the VR1 loop is a well recognized structure, the corresponding amino acid residues may be readily identified by one of skill in the art. For example, Table 4 lists includes a list of exemplary VR1 amino acid residues. While specific residues are listed, it will be understood by one of skill in the art that the boundaries of the VR1 region are approximate and may vary by one or two residues.

TABLE 4

| Parvovirus | VR1 Amino Acid Residues |
|---|---|
| AAV1 | $_{262}$SSASTGASNDNHY$_{273}$ (SEQ ID NO: 1) |
| rAAV2 | $_{262}$SSQSGAS$_{268}$ (SEQ ID NO: 2) |
| rAAV3b | $_{262}$SSQSGASNDNHY$_{273}$ (SEQ ID NO: 3) |
| rAAV4 | $_{256}$ESLQSNTYK$_{263}$ (SEQ ID NO: 4) |
| rAAV5 | $_{252}$SGSVDGS$_{258}$ (SEQ ID NO: 5) |
| rAAV6 | $_{262}$SSASTGASNDNHY$_{273}$ (SEQ ID NO: 6) |
| rAAV8 | $_{263}$NGTSGGAT$_{270}$ (SEQ ID NO: 7) |
| rAAV9 | $_{261}$SNSTSGGSS$_{269}$ (SEQ ID NO: 8) |

The VR1 region of parvovirus and AAV is characterized by a number of hydrogen bonds that stabilize the region. For example, the AAV1 capsid contains four hydrogen bonds in the VR1 region and the AAV6 capsid contains two hydrogen bonds in the BR1 region (see FIG. 8). The stability of the VR1 loop can be reduced by eliminating one or more of the hydrogen bonds in the region, e.g., by deleting an amino acid residue involved in hydrogen bonding or substituting the amino acid residue with a residue that does not form a hydrogen bond. In some embodiments, at least 1, 2, 3, or 4 or more hydrogen bonds are disrupted within the VR1 loop.

Hydrogen bonds formed by amino acid residues in the VR1 loop can be identified by methods known in the art, including the computational analysis of capsid protein crystal structures, capsid protein nuclear magnetic resonance structures, comparisons of sequence homology, etc. Examples of amino acid residues directly involved in hydrogen bonding in the VR1 loop are listed in Table 5.

TABLE 5

| Virus | Hydrogen Bonds |
|---|---|
| AAV1 | HG1 T265 to O S262<br>O A263 to HG1 T265<br>OG S264 to H T265 |

TABLE 5-continued

| Virus | Hydrogen Bonds |
|---|---|
| AAV2 | OG S264 to H G265 |
|  | H A266 to O Q263 |
| AAV3b | O Q263 to H A266 |
|  | O Q263 to H G265 |
| AAV4 | O L258 to H N261 |
| AAV5 | H S258 to O V255 |
|  | O S258 to H N261 |
| AAV6 | O S264 A to HG S264 A |
|  | HG1 T265 to O S262 |
|  | OG S262 to HD1 H272 |
| AAV8 | HG1 T265 to O T265 |
| AAV9 | HG S265 to O S265 |
|  | H G267 to O S263 |

For example, crystal structures may be downloaded from public databases, e.g., the RCSB Protein Data Bank (rcsb.org), a publicly accessible repository for all structures that were generated using NIH funding. Individual pdb files may be run through a structural validity program, such as the publicly available MolProbity4 structural validation program (molprobity.biochem.duke.edu), which analyzes the geometric relationships between individual molecules within a crystal structure as well as their electron-cloud positions in order to provide visual information on the location of hydrogen bonding in a given structure/pdb file. The output of MolProbity is a Kinemage, which is a graphic representation of the crystal structure with included hydrogen bonding, and which can be visualized using the publicly available software program KiNG (kinemage.biochem.duke.edu).

In some embodiments, the transduction efficiency of a virus vector comprising the modified capsid protein is increased at least about 10% relative to a virus vector comprising a capsid protein that does not contain the modification, e.g., at least about 10%, 20%, 30%, 40%, 50%, 60%, 70%, 80%, 90%, 100%, 150%, 200%, 500%, or more. The capsid protein that does not contain the modification may be a wild-type capsid protein or may be a synthetic capsid protein as long as it does not contain the modifications of the present invention. Transduction efficiency may be measured by techniques well known in the art and as described herein.

In some embodiments, the tissue specificity of a virus vector comprising the modified capsid protein is altered. In certain embodiments, the transduction of muscle, e.g., skeletal and/or cardiac muscle, is increased at least about 10% relative to a virus vector comprising a capsid protein that does not contain the modification, e.g., at least about 10%, 20%, 30%, 40%, 50%, 60%, 70%, 80%, 90%, 100%, 150%, 200%, 500%, or more. In certain embodiments, the transduction of liver is decreased at least about 10% relative to a virus vector comprising a capsid protein that does not contain the modification, e.g., at least about 10%, 20%, 30%, 40%, 50%, 60%, 70%, 80%, 90%, 100%, 150%, 200%, 500%, or more. In some embodiments, the transduction of muscle is increased and the transduction of liver is decreased relative to a virus vector comprising a capsid protein that does not contain the modification. In certain embodiments, the transduction of liver is increased at least about 10% relative to a virus vector comprising a capsid protein that does not contain the modification, e.g., at least about 10%, 20%, 30%, 40%, 50%, 60%, 70%, 80%, 90%, 100%, 150%, 200%, 500%, or more.

In some embodiments, the capsid is modified by deleting or substituting one or more amino acid residues of amino acid residues 258 to 272 of AAV1 capsid protein or the corresponding amino acid residues from another AAV or parvovirus capsid protein, e.g., 1, 2, 3, 4, 5. 6, 7, 8, 9, or 10 or more residues are deleted or substituted. The deleted or substituted residue may be any residue in the VR1 that results in a change in rotamer state for residues that are participating in hydrogen bond networks. In another embodiment, the capsid is modified by deleting or substituting one or more amino acid residues of amino acid residues 261 to 269 of AAV1 capsid protein or the corresponding amino acid residues from another AAV or parvovirus capsid protein. In a further embodiment, the capsid is modified by deleting or substituting amino acid residue 265 of AAV1 capsid protein or the corresponding amino acid residues from another AAV or parvovirus capsid protein.

In certain embodiments, the modification is made to a AAV1 or AAV6 capsid, resulting in an increase in muscle transduction and a decrease in liver transduction. In certain embodiments, the modification is made to a AAV7, AAV8, or AAV9 capsid, resulting in and a decrease in liver transduction while maintaining muscle transduction. In some embodiments, the modification is one or more of the modifications shown in Table 6. In certain embodiments, the modified capsid is not from AAV2, AAV3b, AAV4, or AAV5.

TABLE 6

Variable region 1 deletion mutations.

| Serotype | Mutations |
|---|---|
| rAAV1 | T265del |
| rAAV2 | Q263del, S264del |
| rAAV3b | Q263del |
| rAAV4 | N261del |
| rAAV5 | S258del |
| rAAV6 | S262del, T265del |
| rAAV7 | T265del |
| rAAV8 | T265del |
| rAAV9 | S263del, S265del, S263del_S265del |

In some embodiments, the capsid is modified by inserting one or more amino acid residues (e.g., an aspartic acid) after amino acid residue264 of AAV2 capsid protein or the corresponding amino acid residues from another AAV or parvovirus capsid protein. In another embodiment, the capsid is modified by substituting an amino acid residue of amino acid residue 265 (e.g., with an aspartic acid) of AAV1 capsid protein or the corresponding amino acid residues from another AAV or parvovirus capsid protein.

In certain embodiments, the modification is made to a AAV1, AAV2, or AAV3b capsid, resulting in an increase in liver transduction. In certain embodiments, the modification is made to a AAV6 capsid, resulting in an increase in liver transduction and muscle transduction. In certain embodiments, the transduction of liver is increased at least about 10% relative to a virus vector comprising a capsid protein that does not contain the modification, e.g., at least about 10%, 20%, 30%, 40%, 50%, 60%, 70%, 80%, 90%, 100%, 150%, 200%, 500%, or more. In other embodiments, the modification is one or more of the modifications shown in Table 7.

TABLE 7

Variable region 1 aspartic acid insertion and substitution mutations.

| Serotype | Mutations |
|---|---|
| rAAV1 | T265D |
| rAAV2 | 265D |
| rAAV3b | 266D |
| rAAV6 | T265D |
| rAAV8 | T265D |
| rAAV9 | S265D |

A further aspect of the invention relates to the effect of reducing the heparin sulfate binding capability of capsid proteins on transduction efficiency. The examples herein demonstrate that substantially reducing the binding of the capsid protein to heparin sulfate enhances transduction efficiency. It is further demonstrated that, in some instances, the substantial reduction of heparin sulfate binding capability allosterically interacts with destabilization of the VR1 loop to provide a substantial increase in transduction efficiency compared to either modification alone.

In one aspect of the invention, the capsid protein comprising a modification in the VR1 loop is from an AAV serotype or other parvovirus that binds to heparin sulfate, wherein one or more amino acid residues that mediate binding of the capsid protein to heparin sulfate are substituted and/or deleted, wherein binding of the capsid protein to heparin sulfate is substantially reduced. The term "substantially reduced," as used herein, refers to a reduction in heparin sulfate binding ability of at least about 80%, e.g., at least about 85%, 90%, 95%, 96%, 97%, 98%, or 99%, or more. The binding of capsid proteins to heparin sulfate can be measured by techniques well known in the art and as described herein.

In some embodiments, the capsid protein that binds heparin sulfate is from an AAV2, AAV3a, AAV3b, AAV6, or AAV8 serotype. In some embodiments, the capsid protein that binds heparin sulfate is from an AAV3a, AAV3b, AAV6, or AAV8 serotype. The amino acid residue(s) involved in heparin sulfate binding in each of these serotypes are well known in the art. Examples include, without limitation, R484, R487, K532, R585, and R588 in AAV2, K531 in AAV6, and R594 in AAV3b. In some embodiments, the capsid protein that binds heparin sulfate includes any synthetic AAV or parvovirus capsid protein that has been modified to provide heparin sulfate binding capability.

In one embodiment, the capsid protein comprises the amino acid sequence from an AAV6 serotype, wherein amino acid residue 531 has been substituted to substantially reduce binding to heparin sulfate, e.g., by substitution with glutamic acid. In another embodiment, the capsid protein comprises the amino acid sequence from an AAV2 serotype, wherein amino acid residue 585 has been substituted to substantially reduce binding to heparin sulfate, e.g., by substitution with glutamic acid. In another embodiment, the capsid protein comprises the amino acid sequence from an AAV3b serotype, wherein amino acid residue 594 has been substituted to substantially reduce binding to heparin sulfate, e.g., by substitution with alanine.

Another aspect of the invention relates to capsid proteins in which one or more amino acid residues that mediate binding of the capsid protein to heparin sulfate are substituted and/or deleted, wherein binding of the capsid protein to heparin sulfate is substantially reduced. In some embodiments, these capsid proteins do not have a modification in the VR1 loop. In some embodiments, the capsid protein comprises an amino acid sequence from an AAV3a, AAV3b, AAV6, or AAV8 serotype. In one embodiment, the capsid protein comprises the amino acid sequence from an AAV6 serotype, wherein amino acid residue 531 has been substituted to substantially reduce binding to heparin sulfate, e.g., by substitution with glutamic acid.

A further aspect of the invention relates to an AAV capsid protein comprising an amino acid sequence from an AAV2, AAV3a, or AAV3b serotype, wherein the capsid protein comprises an insertion of one or more amino acid residues immediately following residue 264 of AAV2 capsid protein or the corresponding residue of AAV3a or AAV3b capsid protein, and one or more amino acid residues that mediate binding of the capsid protein to heparin sulfate are substituted and/or deleted, wherein binding of the capsid protein to heparin sulfate is substantially reduced, wherein the capsid protein provides to a virus vector comprising the capsid protein increased transduction efficiency relative to a virus vector comprising an unmodified capsid protein.

The insertion of one or more amino acid residues immediately following residue 264 of AAV2 capsid protein has been demonstrated to enhanced transduction efficiency (see, e.g., U.S. Pat. No. 7,892,809, incorporated herein by reference in its entirety). In one embodiment, the insertion immediately following residue 264 of AAV2 capsid protein or the corresponding residue of AAV3a or AAV3b capsid protein is of an aspartic acid, glutamic acid, or phenylalanine residue. In one embodiment, the capsid protein comprises an amino acid sequence from an AAV2 serotype, wherein amino acid residue 585 has been substituted to substantially reduce binding to heparin sulfate, e.g., with glutamic acid.

A further aspect of the invention relates to an AAV capsid protein comprising a deletion and/or substitution of one or more amino acid residues of amino acid residues 258 to 272 of AAV1 capsid protein or the corresponding amino acid residues from another AAV or parvovirus capsid protein and further comprising a substitution of a tyrosine residue, e.g., to improve cardiac transduction efficiency. Mutation of select tyrosine residues on the rAAV capsid surface has been shown to enhance rAAV transduction efficiency by avoiding the phosphorylation and ultimate proteasomal degradation of intracellular capsids before they are able to reach the nucleus (Zhong et al., *Virology* 381(2):194 (2008)). In some embodiments the tyrosine substitution is Y445F AAV1 or AAV6.

One aspect of the invention relates to a polynucleotide encoding the capsid protein of the invention. In some embodiments, the polynucleotide comprises, consists essentially of, or consists of a nucleotide sequence encoding the capsid protein of the invention, e.g., one of the sequences disclosed herein. In other embodiments, the polynucleotide comprises, consists essentially of, or consists of a nucleotide sequence encoding a capsid protein that is at least 80% identical, at least 85%, 90%, 95%, 96%, 97%, 98%, or 99% identical to one of the capsid protein sequences disclosed herein.

An additional other aspect of the invention relates to a parvovirus capsid comprising the capsid protein of the invention. In some embodiments, all of the capsid proteins in the capsid are capsid proteins of the invention. In other embodiments, some but not all of the capsid proteins in the capsid are capsid proteins of the invention.

The invention also provides a viral vector comprising the parvovirus capsid of the invention. The viral vector may be a parvovirus vector, e.g., an AAV vector. The viral vector may further comprise a nucleic acid comprising a recombinant viral template, wherein the nucleic acid is encapsidated by the parvovirus capsid. The invention further provides a recombinant parvovirus particle (e.g., a recombinant AAV particle) comprising the capsid protein of the invention. Viral vectors and viral particles are discussed further below.

In certain embodiments, the viral vector exhibits a modified tropism due to the presence of the capsid protein of the invention. In one embodiment, the parvovirus vector exhibits systemic tropism for skeletal, cardiac muscle, and/or diaphragm muscle, e.g., for skeletal muscle. In other embodiments, the parvovirus vector has reduced tropism for liver compared to a virus vector comprising a wild-type capsid protein.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a heterologous nucleotide sequence, and (ii) a parvovirus ITR; (b) a polynucleotide comprising Rep coding sequences and the Cap coding sequences of the invention; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can he collected from the medium and/or by lysing the cells.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can he provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et at., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g , for vaccines), or diagnostic polypeptides.

Therapeutic polypeptides include, but are not limited to, cystic fibrosis transmembrane regulator protein (CFTR), dystrophin (including mini- and micro-dystrophins (see, e.g., Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. Parvovirus vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Set. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al., *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.), Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882, 652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis vim immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can he operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inns), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, vim vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-firming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may he either solid or liquid. For inhalation administration, the carrier will be respirable, and optionally can be in solid or liquid particulate form.

By "pharmaceutically acceptable" it is meant a material that is not toxic or otherwise undesirable, i.e., the material may he administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered. to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye [including intravitreal and subretinal], skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radians brevis, extensor carpi radialis longus, extensor carpi ulnaris, extensor digiti minimi, extensor digitorum, extensor dilzitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus inferior gemellus, inferior oblique, inferior rectus, infraspinatus, interspinalis, inteitransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the toot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, stemohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder e.g., a metabolic disorder, such as diabetes (e.g., insulin), hemophilia Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of deliverine virus vectors to skeletal muscle are described in more detail herein.

The invention can also he practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally or subretinally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins as are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and pen-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

EXAMPLE 1

Materials and Methods

Plasmids and viruses. All plasmids were obtained from the University of North Carolina Gene Therapy Center Vector Core facility. Virus was generated via triple transfection of HEK293 cells and purified by cesium chloride density ultracentrifugation. Viral titer was obtained using real time quantitative PCR (qPCR) analysis, using the following primer set designed to recognize the luciferase transgene: (forward) 5'-AAA AGC ACT CTG ATT GAC AAA TAC-3' (SEQ ID NO:9) and (reverse) 5'-CCT TCG CTT CAA AAA ATG GAA C-3' (SEQ ID NO:10); or the following primer set designed to recognize human α1 antitrypsin gene: (forward) 5'-GAA GTC AAG GAC ACC GAG GA-3' (SEQ ID NO:11) and (reverse) 5'-CCC AGC TGG ACA GTC TCT TA-3' (SEQ ID NO:12). For all experimental groups, relevant viral constructs were titered together on the same qPCR plate prior to being used. Site-directed mutagenesis (Stratagene QuikChange) was used for nucleotide deletion or substitution. Table 8 lists the primer sequences used for all VR1 mutants examined in this study. rAAV1→rAAV6 point mutants (e.g., rAAV6.1, etc) were already part of general lab stocks. DNA sequencing was performed on each plasmid used in this work to verify sequence identity prior to making virus.

TABLE 8

Primers used for site-directed mutagenesis of VR1 mutants.

| Name | Sequence (listed 5' to 3') |
|---|---|
| rAAV1/T265D | gca atc tcc agt gct tca gac ggg gcc agc aac g (SEQ ID NO: 13) |
| rAAV1/T265E | gca atc tcc agtngct tca gag ggg gcc agc aac g (SEQ ID NO: 14) |
| rAAV1/T265F | gca atc tcc agt gct tca ttc ggg gcc agc aac gac (SEQ ID NO: 15) |
| rAAV1/S261del | caa gca aat cag tgc ttc aac ggg gg (SEQ ID NO: 16) |
| rAAV1/S262del | gca aat ctc cgc ttc aac ggg gg (SEQ ID NO: 17) |
| rAAV1/A263del | gca aat ctc cag ttc aac ggg ggc (SEQ ID NO: 18) |
| rAAV1/S264del | caa atc tcc agt gct acg ggg gcc aga aac (SEQ ID NO: 19) |
| rAAV1/T265del* | ctc cag tgc ttc agg ggc cag caa cg (SEQ ID NO: 20) |
| rAAV1/G266del | cca gtg ctt caa cgg cc gca agc (SEQ ID NO: 21) |
| rAAV1/A267del | gct tca acg ggg agc aac gac aac c (SEQ ID NO: 22) |
| rAAV1/S268del | cgg ggg cca acg aca acc ac (SEQ ID NO: 23) |
| rAAV1/N269del | cgg ggg cca gcg aca acc act tc (SEQ ID NO: 24) |

*exact rAAV1/T265del primer was used to create rAAV6/T265del mutants.

Live-animal studies. All animals were maintained and treated in accordance with National Institutes of Health guidelines, under protocols approved by the IACUC at the University of North Carolina, Chapel Hill. rAAV variants packaging either the CBA-luciferase or CBA-hAAT transgene were injected into the GC of 6-8 week old female BALB/c mice (Jackson Laboratories) at indicated quantities. All injections were performed in 50 µL total volume per injection. Mice were anesthetized using isoflurane gas prior to injection. Luciferase transgene expression was monitored at indicated time points using a Xenogen IVIS Lumina imaging system (Perkin Elmer/Caliper Life Sciences) following intraperitoneal injection of D-luciferin substrate (Nanolight) at 120 mg/kg body weight. Bioluminescent image analysis was performed using Living Image software (Perkin Elmer/Caliper Life Sciences), and luciferase expression is reported in CPM/ROI (counts per minute over a selected region of interest).

Ex vivo quantitation of transgene expression and copy number. For ex vivo luciferase assay, mice were sacrificed at 7 dpi of 1e10vg and injected muscle tissue harvested.

Approximately 50 mg of each tissue was minced on ice. Each tissue aliquot was then homogenized in 150 μL of 2× Passive Lysis Buffer (Promega) using a Tissue Tearor (Cole-Parmer). 35 μL of lysates and 100 μL of D-luciferin substrate (Promega) were transferred to 96-well plates for luminometric analysis using a Victor2 luminometer (Perkin Elmer). Total protein concentration in tissue lysates was determined via Bradford assay (Bio-Rad). At 3 dpi of 1e10vg, injected GC was harvested homogenized and lysed as above, and a ~25 mg tissue aliquot was processed using a DNeasy kit (Qiagen) to extract host and vector genomic DNA. The number of cells was determined via qPCR with the following primers designed specific to the mouse Lamin (a housekeeping gene): (forward) 5'-GGA CCC AAG GAC TAC CTC AAG GG-3' (SEQ ID NO:25) and (reverse) 5'-AGG GCA CCT CCA TCT CGG AAA C-3' (SEQ H) NO:26). The number of viral genomes per cell was determined via qPCR with primers designed specific to the luciferase transgene, as described above.

Heparin competition. Indicated constructs were incubated in either a 250 μg/mL solution of porcine heparin sulfate sodium salt (Sigma-Aldrich) dissolved in Ringer's saline solution (RSS), or Ringer's saline solution alone, overnight at 4° C. with rotation. 1e10vg of each group was injected per GC in a total volume of 50 μL per injection. At 7 dpi, live animal bioluminescent imaging was performed.

Molecular modeling. The three-dimensional structures of rAAV1, rAAV2 or rAAV6 were displayed as whole capsids (a kind gift from Dr. Mavis Agbandje-Mckenna) using previously published coordinates in PyMol (pymol.org). The PyMol align command was used to align various structures. Atom pairs involved in hydrogen bonding were calculated on crystal structure coordinates using MolProbity and visualized using KiNG graphic software (kinemage.biochem.duke.edu).

Heparin affinity chromatography. Indicated constructs were incubated with heparin sulfate conjugated agarose beads (Sigma-Aldrich) overnight at 4° C. with rotation. Slurry was transferred to a micro chromatography column (Bio-Rad) and washed 3 times with RSS, followed by increasingly stringent NaCl washes. Solutions were made by dissolving appropriate quantity of NaCl into RSS, after adjusting for amount of NaCl already present in the solution. All wash fractions were collected. Percent virus contained in each fraction was determined by qPCR quantification of viral particles contained within each wash, using primers designed against the luciferase transgene, described above.

ELISA detection of human AAT. Mouse blood was collected via retro-orbital bleed using heparinized capillary tubes (Sigma-Aldrich). Immediately following collection, samples were pelleted and serum collected and stored at −80° C. for future use. Mice were anesthetized with isoflurane gas prior to bleeding. A 96-well plate was coated with rabbit anti-human AAT antibody (Sigma-Aldrich) at 10 mg/mL overnight at 4° C. Plate was then washed and blocked with serum dilution solution (PBS with 2.5% bovine albumin and 0.05% Tween) for 1 hour at room temperature. Indicated serum dilutions (100 μL total per each sample) were added to plate and incubated for 2 hours at room temperature. After washing 4 times with PBS, 100 μL of HRP-conjugated goat anti-human AAT antibody (10 ug/mL; Abcam) was added to plate for 1 hour at room temperature. After further washing, color was developed by addition of the TMB substrate (Pierce) and arrested by 10% $H_2SO_4$. Optical density was read using an iMark microplate reader (Bio-Rad). Murine AAT was not detectable with this assay.

EXAMPLE 2

Figure 1A:
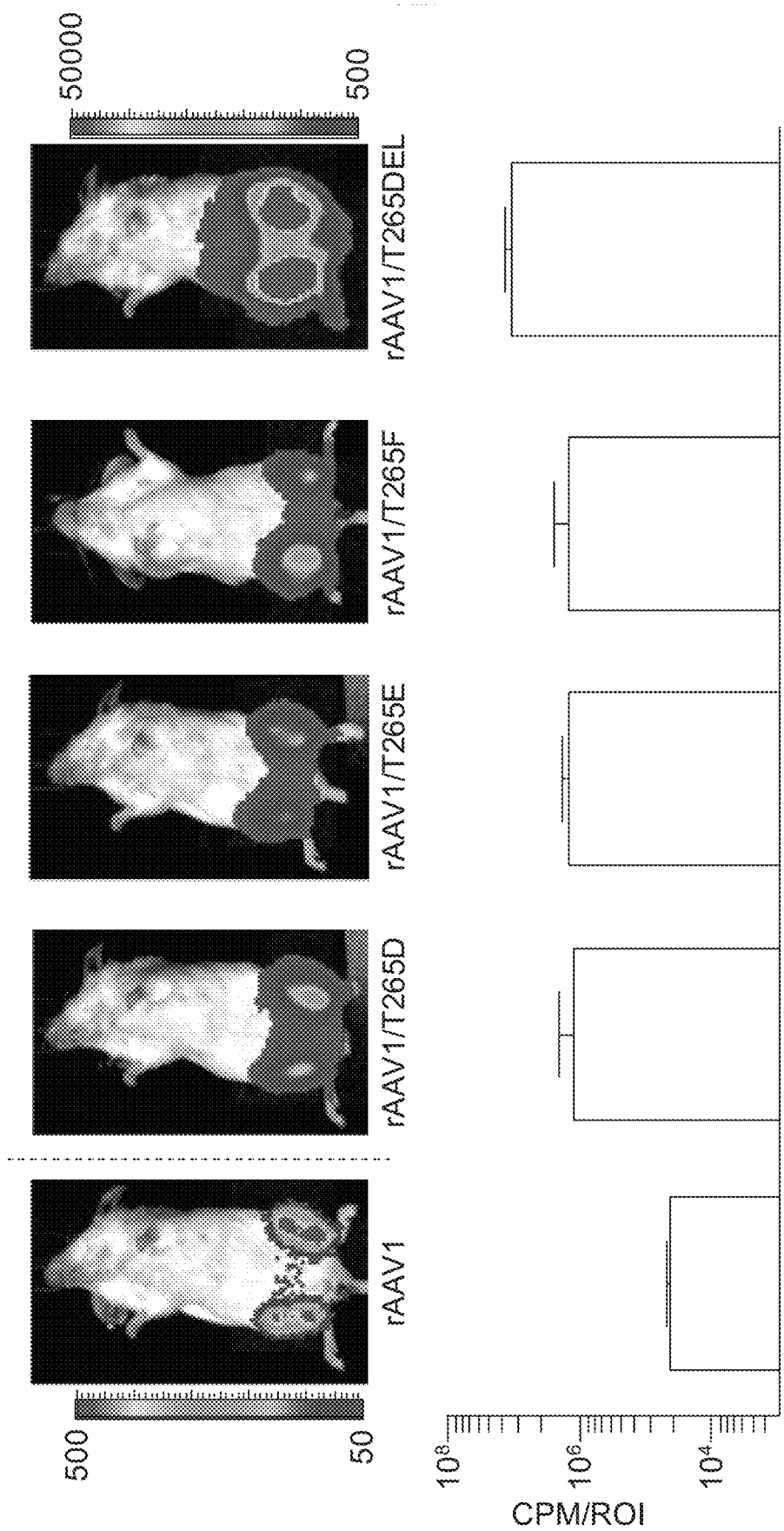
FIGS. 1A-1D show in vivo characterization of rAAV1 position 265 mutants following i.m. injection. (A) Mice were administered 1e10 vg into the GC. Luciferase transgene expression was visualized and quantified using live animal bioluminescent imaging at 7 dpi. Units displayed are counts per minute over region of interest (CPM/ROI). For visualization purposes, rAAV1 is shown on a different scale than the 265 mutants. This does not affect image quantitation. For ex vivo quantification of transduction phenotype (B), injected muscle was harvested and lysed, and luciferase assay performed on tissue lysate. Measurements depicted as relative light units normalized to mg total protein (RLU/mg protein). (C) Viral transgene copy numbers per cell (vg/cg) were measured using qPCR. (D) A time course of expression kinetics was performed on rAAV1 and rAAV1/T265del following injection of 1e10vg. All data represents n=4 per group; in panel (A) one representative image is displayed per group.

Mutation of Position 265 on the rAAV1 Capsid Enhances Transduction of Skeletal Muscle As insertions of aspartic acid, glutamic acid or phenylalanine following position 264 in the rAAV2 capsid (creating a de novo position 265) enhanced skeletal muscle transduction by an order of magnitude, we hypothesized that substitution of the naturally present threonine at position 265 in rAAV1 with D, E, or F would enhance skeletal muscle transduction in this serotype (rAAV1 is one amino acid longer than rAAV2 in this capsid loop). As a control, T265 was deleted from rAAV1, so as to resemble unmodified rAAV2. rAAV1, rAAV1/T265D, rAAV1/T265E, rAAV1/T265F and rAAV1/T265del capsids packaging the chicken β-actin promoter driven firefly luciferase (CBA-luc) transgene were injected into murine gastrocnemius (GC) muscle at a dose of 1e11 viral genomes (vg). Live-animal bioluminescent imaging was performed 7 days post injection (dpi) in order to quantify transgene expression via measurement of emitted light (FIG. 1A). rAAV1/T265D, rAAV1/T265E and rAAV1/T265F enhanced transgene expression relative to rAAV1 by 28-, 34- and 36-fold, respectively, supporting our previous analysis in the rAAV2 capsid backbone. Surprisingly, rAAV1/T265del enhanced transduction by approximately 200-fold over rAAV1. In an effort to better understand this phenomena, the 265 deletion mutant was used in the majority of remaining analyses within this study.

Figure 1B:
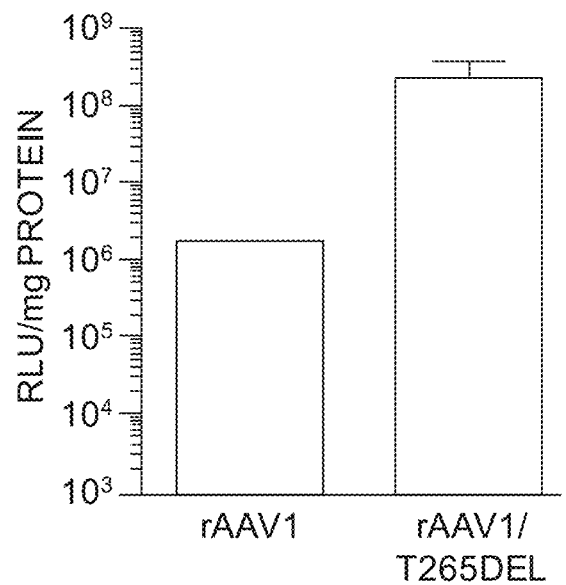
Figure 1C:
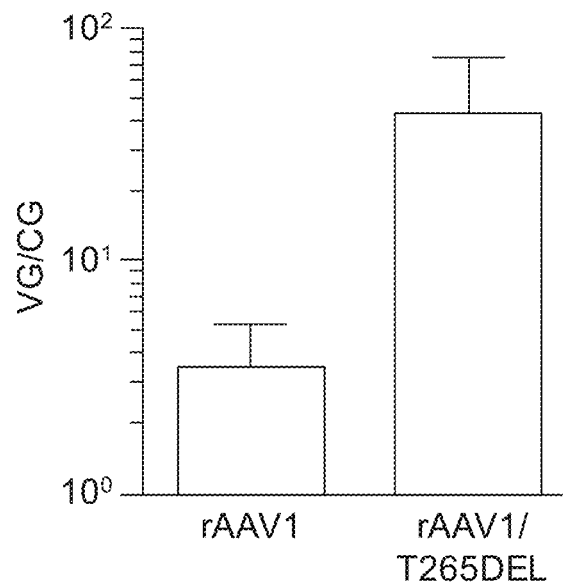

To confirm that the image quantification method used to generate the above data was an accurate representation of transgene expression levels within injected muscle tissue, injected GCs were removed, homogenized/lysed and ex vivo luciferase assay performed on tissue lysate. In this assay, transduction efficiency with rAAV1/T265del was enhanced by 137-fold over rAAV1, when normalized for relative light units emitted per mg of tissue analyzed (FIG. 1B). Increased rAAV1/T265del reporter gene expression correlated with enhanced transgene delivery to muscle: 14.5-fold more viral genome copies were detected per muscle cell relative to rAAV1 by quantitative real-time PCR (qPCR) analysis (FIG. 1C). All results were confirmed in multiple experiments using independent preparations of vectors purified by several methods (e.g., density ultracentrifugation, affinity chromatography) to ensure that measured effects were not specific to batch or purification method.

Figure 1D:
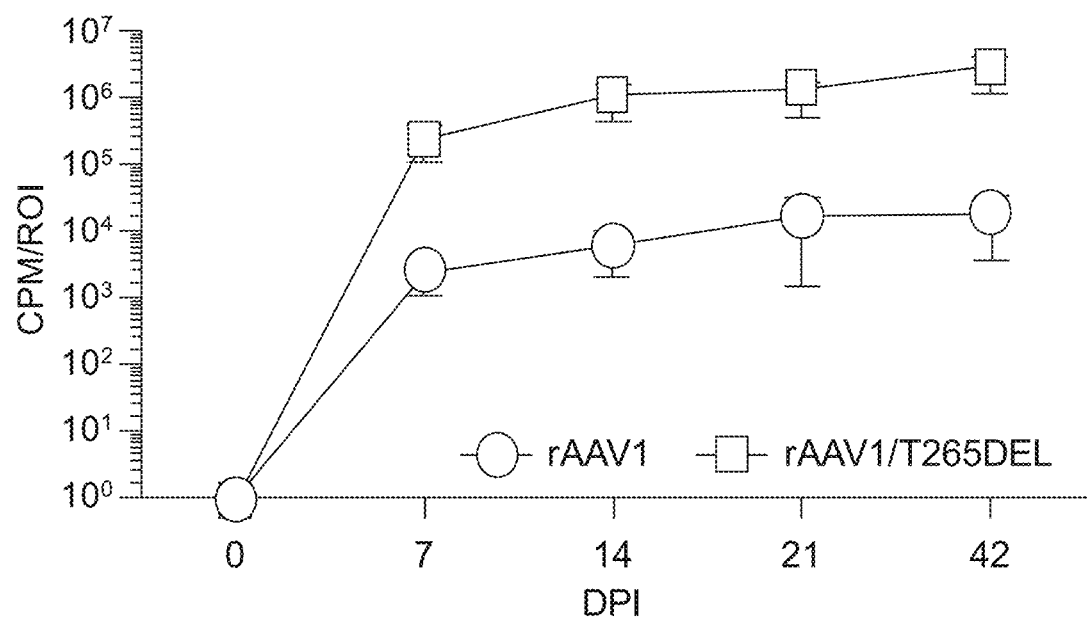

To ensure an appropriate time point was examined, a time course of rAAV1 and rAAV1/T265del transgene expression was performed, with measurements collected at 7, 14, 21 and 42 dpi (FIG. 1D). Expression kinetics appeared the same, with robust expression observed at 7 dpi, increasing by 7.5-fold between days 7 and 42 following injection of rAAV1 and by 12-fold during same time period following injection of rAAV1/T265del. At all time points, rAAV1/T265del outperformed rAAV1 by approximately two orders of magnitude (100-fold at day 7, 176-fold at day 14, 81-fold at day 21, and 159-fold at day 42). Taken together, these data demonstrate that deletion of amino acid 265 in the rAAV1 capsid backbone is a highly effective strategy to enhance both transgene delivery and expression in skeletal muscle tissue. More importantly, this enhancement is maintained over a sustained period of time supporting our observation of increased vector genome copy numbers as documented by qPCR analysis.

EXAMPLE 3

Figure 2A:
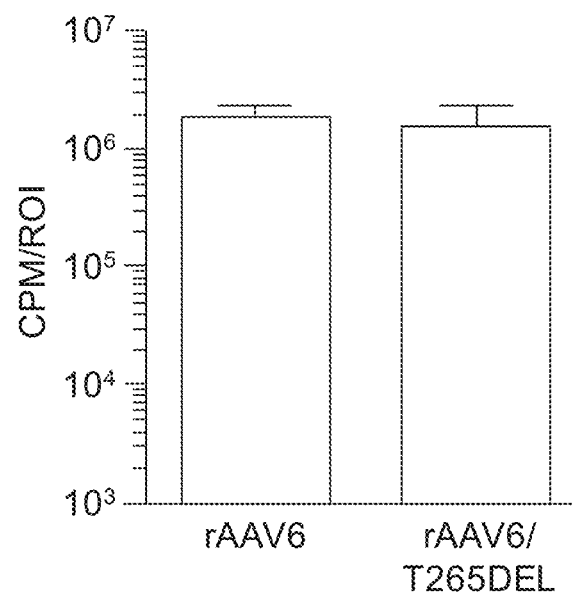
FIGS. 2A-2C show the phenotype of 265 deletion mutant in rAAV6. (A) Luciferase transgene expression 7 dpi of 1e10 vg of either rAAV6 or rAAV6/T265del. (B) Alignment of the VR1 capsid region of rAAV1 (light grey) and rAAV6 (dark grey). Residue 265 is highlighted in dark blue on rAAV1 and in yellow on rAAV6. Image generated in PyMol using available crystallographic coordinates for these capsids. (C) Transgene expression following injection of rAAV1→rAAV6 point mutants into mouse GC. Data represented as fold difference relative to measured expression of rAAV6. All data represents n=4 per group.
Figure 2B:
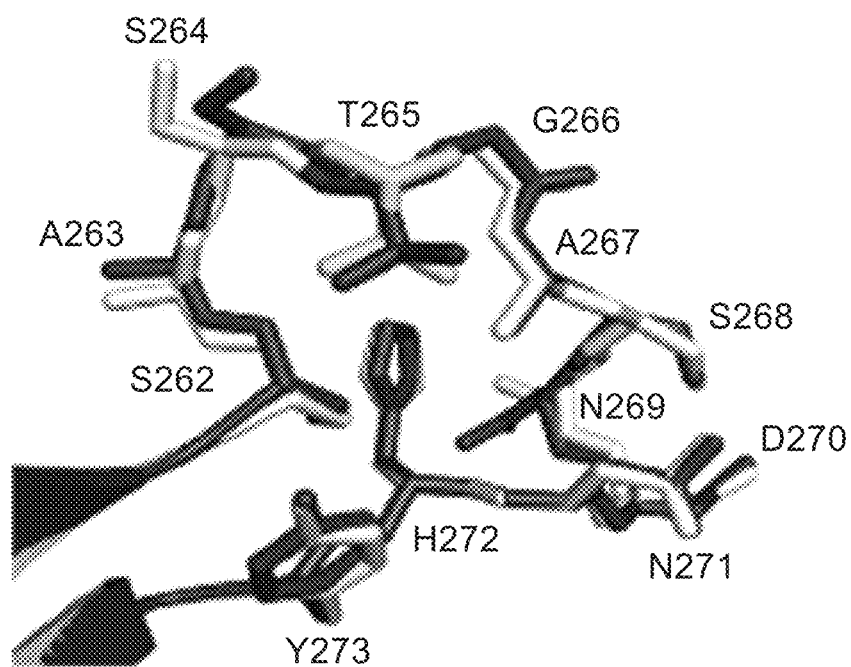

Distal Residues Work in Conjunction with 265 to Modulate Transduction Efficiency rAAV6 is considered another top candidate for musculoskeletal gene therapy applications, and is the serotype with the highest capsid sequence homology (99.2%) to rAAV1. To determine whether the enhanced transduction phenotype obtained by the deletion of position 265 in the rAAV1 capsid would be conserved in the context of rAAV6, rAAV6 and rAAV6/T265del capsids packaging CBA-luc were generated. Seven days following injection of each into murine GC at a dose of 1e10vg, transgene expression was quantified. Intriguingly, the transgene expression following injection of rAAV6/T265del was only 82% of that measured when using rAAV6 (FIG. 2A). This was surprising considering the dramatic effects on transduction that deletion of position 265 produced in rAAV1, and that of the only 6 amino acids by which rAAV1 and rAAV6 differ, none are located within sufficient spatial proximity to position 265 to form direct interactions. Furthermore, any residue that differs between rAAV1 and rAAV6 is located at least 22 Å away from position 265. In order to form direct interactions such as hydrogen bonding, residues must be within ~3 Å of each other. Despite this, there are conformational differences within the structure of rAAV1 and rAAV6 around position 265 (FIG. 2B), as visualized by alignment of available crystallographic data for each.

Figure 2C:
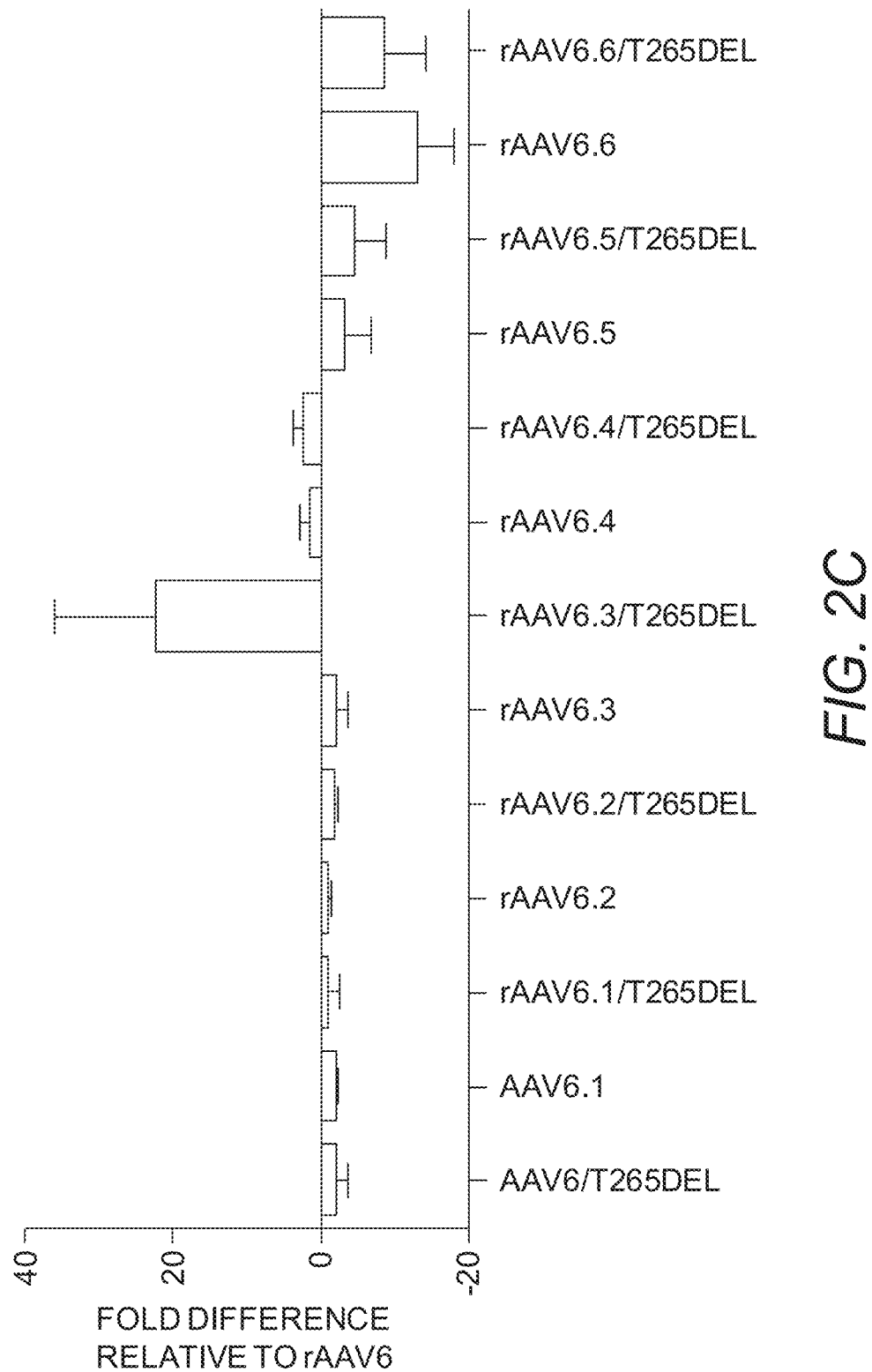

To resolve which residues within the rAAV6 capsid might inhibit the effectiveness that deleting position 265 has on enhancing transduction efficiency a version of marker rescue experiment was employed, wherein the rAAV6 capsid was mutated at each residue that differs between rAAV1 and rAAV6 to the amino acid present in rAAV1, in conjunction with deletion of 265. Mutants were designated rAAV6.1 (rAAV6 with the first non-conserved residue (F129I) mutated to the equivalent amino acid in rAAV1), rAAV6.2 (D418E), rAAV6.3 (K531E), rAAV6.4 (L584F), rAAV6.5 (V598A) and rAAV6.6 (H642N), respectively. The majority of changes to the rAAV6 capsid produced minimal change to transduction (FIG. 2C). Transgene expression decreased by ≤2-fold with constructs rAAV6.1, rAAV6.1/T265del, rAAV6.2, rAAV6.2/T265del and rAAV6.3, respectively. Transgene expression was increased by approximately 2-fold in both rAAV6.4 and rAAV6.4/T265del. Mutations at position 598 and 642 (rAAV6.5 and rAAV6.6) reduced transgene expression relative to rAAV6 more dramatically than other mutations, decreasing it by 3.4- and 13.1-fold, respectively. Deletion of position 265 in conjunction with rAAV6.5 and rAAV6,6 produced little change to the performance of these constructs, decreasing transgene expression by 4.8- and 8.7-fold in rAAV6.4/T265del and rAAV6.5/T265del, respectively. Strikingly, only a single amino acid change, at position 531 (rAAV6.3), was required to rescue the 265 phenotype observed with rAAV1, with rAAV6.3/T265del enhancing transduction efficiency by 23-fold relative to rAAV6 (FIG. 2C).

Figure 3A:
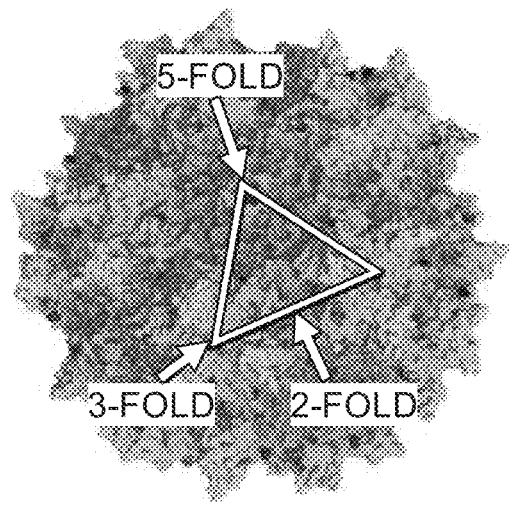
FIGS. 3A-3D show the visualization of amino acid positions 265 and 531 on the rAAV6 capsid. Pymol depiction of the crystallographic coordinates of the rAAV6 capsid (A), with each icosahedral axis of symmetry labeled. (B) Close up of the 3-fold axis of symmetry, with residues 265 and 531 colored purple and orange, and denoted by arrows. (C) Close up of the 5-fold axis of symmetry, with residues 265 and 531 colored purple and orange, and denoted by arrows. (D) Close up of the 2-fold axis of symmetry, with residues 265 and 531 colored purple and orange, and denoted by arrows.
Figure 3B:
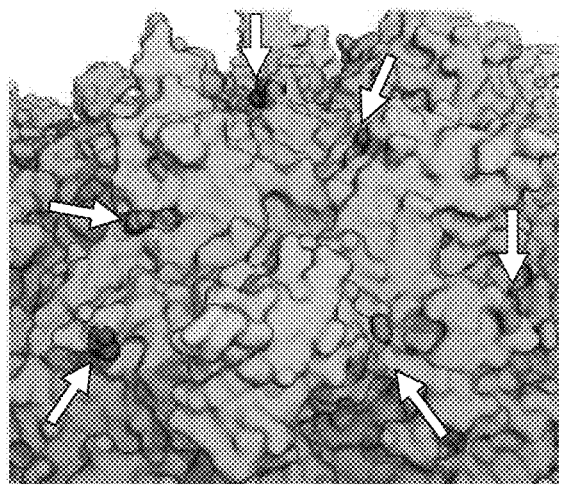
Figure 3C:
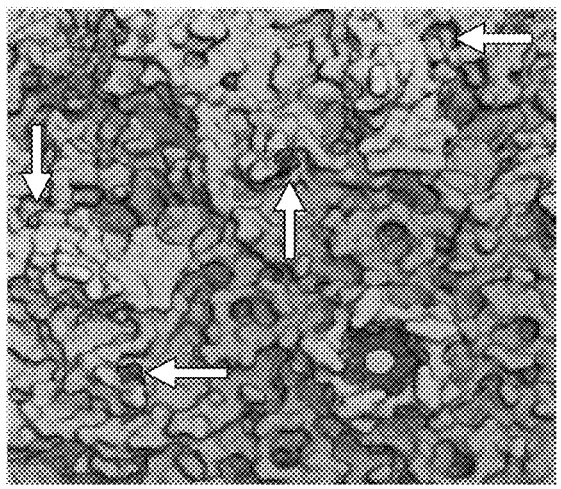
Figure 3D:
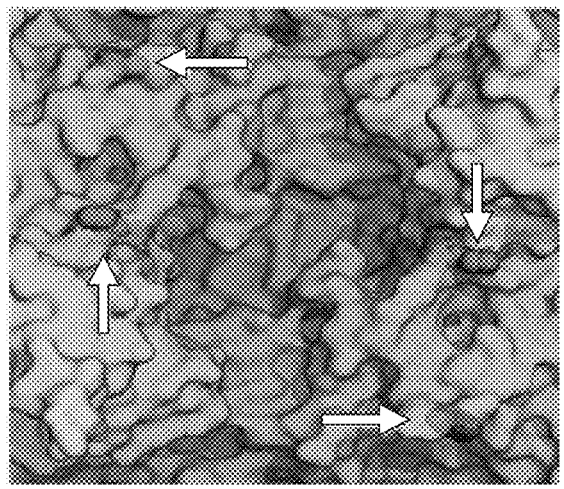
Figure 5A:
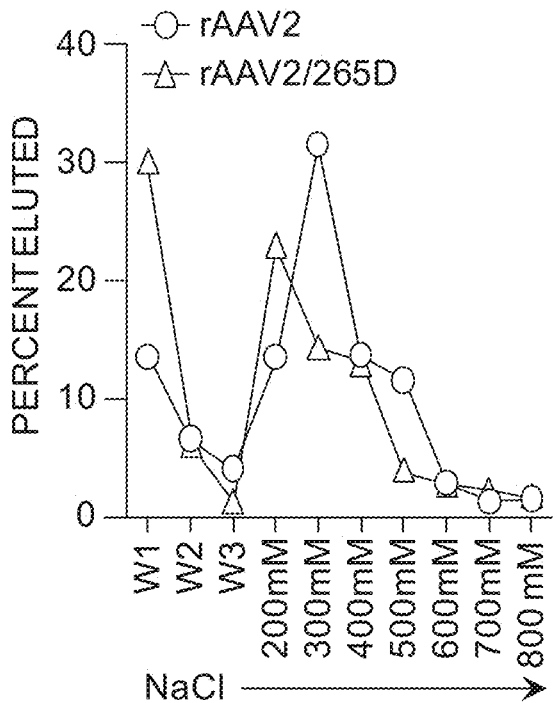
Figure 5B:
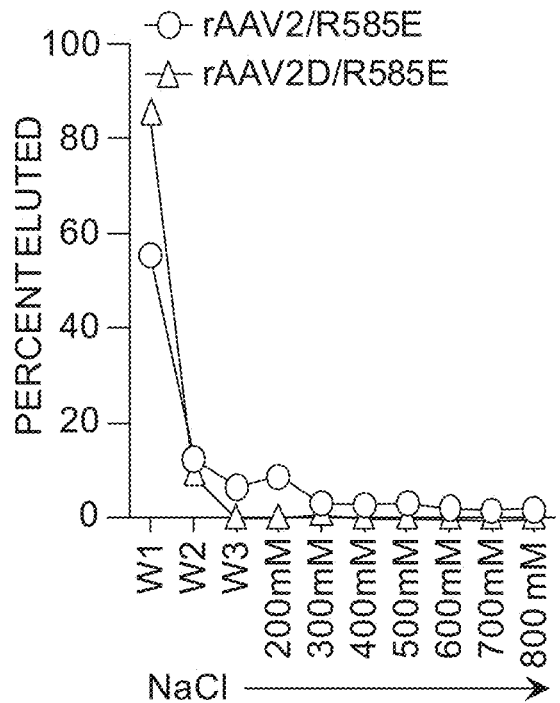
Figure 5C:
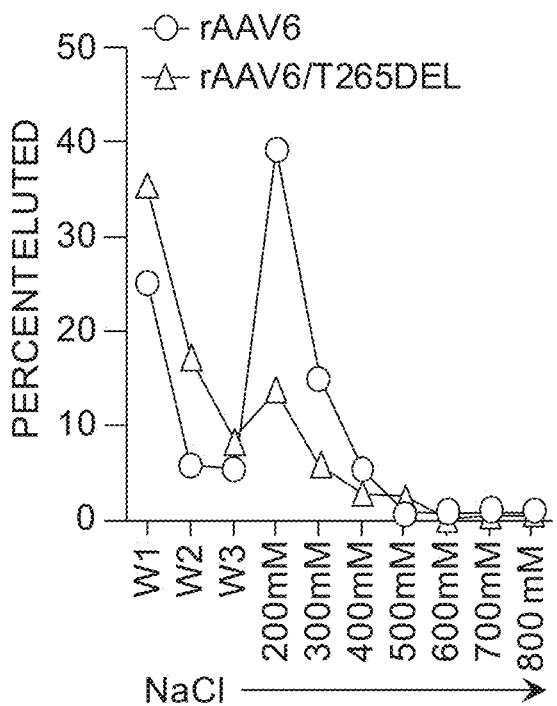
Figure 5D:
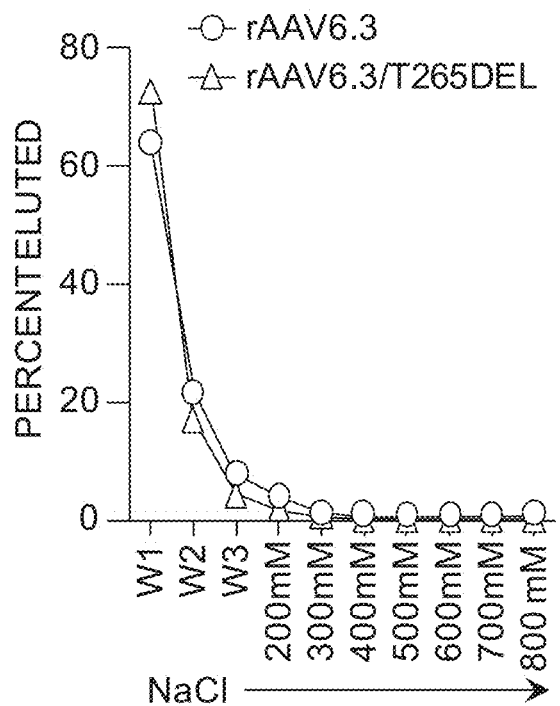

The spatial relationship between residues 531 and 265 was examined in the context of the rAAV6 crystal structure (FIGS. 3A-3D). Amino acids 265 and 531 are not close enough to form direct interactions in any of the icosahedral axes of symmetry. In the 2-fold axis, positions 265 and 531 are ~26.7 Å apart, whereas in the 5-fold axis, they are ~42.6 Å apart. However, in the 3-fold axis of symmetry, despite being located ~22.8 Å apart, both residues are surface-exposed in the same plane (FIG. 3B). Residue 531 sits at the base of each 3-fold "spike" and 265 sits in a slight protrusion between spikes. Taken together, at this point in time, the above data suggests that the most likely context in which positions 265 and 531 may together modulate transduction efficiency is through the protrusions forming the 3-fold axis of symmetry.

EXAMPLE 4

Capsid Heparin Binding Ability Affects the 265 Phenotype, and Vice-Versa rAAV 1 and rAAV6 both engage N-linked sialic acid as a primary receptor; however, rAAV6 also binds to heparin sulfate moieties. Previously, our results have shown that K531 is the sole residue required for rAAV6 to interact with heparin sulfate. K531 is also the sole residue required to rescue the 265 deletion phenotype observed in rAAV1. To further explore the functional relationship between capsid heparin binding and the enhanced transduction resulting from mutation of position 265 we examined rAAV2, the prototypical serotype known to utilize heparin sulfate proteoglycans as primary receptors for infection. rAAV2 was mutated at position 585 (a mutation known to attenuate rAAV2 heparin binding) in conjunction with insertion of aspartic acid to create a de novo position 265 as previously described. rAAV2, rAAV2/265D, rAAV2/K585E and rAAV2/265D,K585E were injected into murine GC at a dose of 1e10vg. In agreement with previous reports, ablation of heparin binding enhanced rAAV2 transduction of skeletal muscle. However, concomitant mutation of position 265 and elimination of heparin binding ability produced the strongest enhancement of transduction efficiency (FIG. 4A), increasing transduction by 96-fold over rAAV2 and 7-fold over rAAV2/265D and in agreement with above results observed for rAAV6 (FIG. 2C). It is notable that residue 531 was mutated to ablate heparin binding in rAAV6 and residue 585 was mutated to ablate heparin binding in rAAV2. Though residues 531 and 585 are not close to each other in linear sequence, they both fall within an overlapping basic patch on the capsid surface that is the footprint for heparin binding (FIG. 4B).

To resolve whether direct inhibition of heparin binding enhances transduction of 265 mutants, heparin competition was performed prior to injection of 265 mutant constructs into mice. rAAV2 binds heparin with stronger affinity than into rAAV6, and is the only serotype historically shown to have effective diminution of transduction following incubation in a heparin sulfate solution, so this question was examined in the context of rAAV2. rAAV2 and rAAV2/265D capsids were incubated in either a saline solution or a 250 µg/mL heparin sulfate solution overnight. rAAV1 was included as a control. Viruses were injected into murine GC at a dose of 1e10vg, and mice were imaged 7 dpi. Incubation with heparin sulfate reduced transduction efficiency by approximately 3-fold in both rAAV2 and rAAV2/265D and had virtually no effect on rAAV1, reducing transduction by 0.3-fold (FIG. 4C). These results suggest that the need to ablate heparin sulfate binding in order for mutation of position 265 to be effective at enhancing transduction is due to structural change within the capsid and not inhibition of heparin binding, per se.

Heparin affinity chromatography verified that all rAAV2 and rAAV6 capsid mutations made to decrease heparin binding performed as expected (FIGS. 5A-5D). Relevant constructs were incubated with heparin-conjugated agarose and eluted with an increasing NaCl gradient. Interestingly, in capsids with position 265 mutated, heparin binding was attenuated relative to parental capsids. For example, 20% more rAAV2/265D than rAAV2 eluted during the first wash step following column loading of virus. Similarly, 20% less rAAV2/265D eluted in the 300 mM NaCl fraction than did rAAV2. Likewise, 37% more rAAV6/T265del eluted during column washing than rAAV6, while 25% less rAAV6/T265del eluted at the 200 mM NaCl wash than did rAAV6, supporting the hypothesis of interplay between these two protein motifs (elution of rAAV6 during a less stringent wash fraction than rAAV2 agrees with previous work). While rAAV2/K585E attenuated rAAV2 heparin binding, rAAV2/265D,K585E furthered this effect. 75% of rAAV2/K585E and 96.5% of rAAV2/265D,K585E was eluted during initial wash steps. 10% less rAAV2/265D,K585E than rAAV2/K585E was eluted at 200 mM NaCl. Combined with the data presented in FIGS. 3 and 4, these results add evidence that changes to the capsid region harboring position 265 affect the structural conformation of that region harboring the heparin binding site, and vice-versa.

EXAMPLE 5

Multiple Disruptions to VR1 Structure Enhance Skeletal Muscle Transduction

The data presented thus far suggests that changes in the structural conformation of VR1 alone is the driving force behind the enhanced transduction following mutation of position 265. Therefore, we sought to determine whether additional disruption to VR1 structure could produce a similar enhanced transduction phenotype. rAAV1 was thus mutated to generate S261del, S262del, A263del, S264del, G266del, A267del, S268del and N269del, as illustrated in FIG. 6A. These constructs were injected into murine GC at 1e10vg, alongside rAAV1 and rAAV1/T265del. Transgene expression was quantified 7 dpi (FIG. 6B). Each mutant enhanced transduction efficiency to varying degrees relative to rAAV1. Transduction was enhanced by ≤3-fold in the S261, S262 and N269 deletion constructs. The G266 and S268 deletion constructs enhanced transduction by ~5-fold and the A263del and A267del by ~10-fold relative to rAAV1. The S264 and T265 deletion constructs enhanced transduction the most robustly over rAAV1, increasing transgene expression by 25- and 100-fold, respectively. These data indicate that any disruption made to the VR1 loop via deletion of an amino acid will enhance transduction in rAAV1, with such enhancement peaking via deletion of position 265 and tapering off as mutations are made further away from position 265 (FIG. 6b).

EXAMPLE 6

265 Deletion Mutants Improve Expression of a Therapeutic Transgene

To compare the relative efficacy of the 265-deletion panel, six capsids were packaged with the hAAT expression cassette currently in clinical trial use. rAAV1, rAAV1/T265del, rAAV6, rAAV6/T265del, rAAV6.3 and rAAV6.3/T265del capsids were injected into murine GC at 1e10vg. Serum concentrations of hAAT were measured via ELISA 5 weeks post injection (FIG. 7). In agreement with above, transgene expression was enhanced by deletion of position 265; however, the degree of enhancement did not reach the levels measured by luciferase assay (e.g., by ELISA there was a 9-fold increase in rAAV1/T265del expression over rAAV1, whereas the average measured by luciferase assay was >100-fold). Nonetheless, all 265 mutants outperformed parent serotypes, with rAAV6.3/T265del producing the greatest serum concentration of hAAT.

EXAMPLE 7

Enhanced Transduction Efficiency in the Eye

AAV constructs were injected either subretinally (SRI) or intravitreally (IV) into mice anesthetized with a ketamine/xylazine cocktail. All AAV capsids packaged the reporter gene luciferase under the chicken beta actin promoter (CBh). Constructs that were examined included AAV1 (1-CBh), AAV1/T265del (1.1-CBh), AAV6/T265del (6.1-CBh), AAV6/K531E (6.3-CBh), AAV6/T265del_K531E (6.3.1-CM), and an AAV2 variant previously characterized in our lab, AAV2.5 (2.5-CBh) (Bowles et al., Mol. Ther. 20(2):443 (2012)). Transgene expression was measured as luciferase activity at indicated time points post injection, using the IVIS lumina live animal imaging system. Mice were imaged following intraperitoneal injection of D-luciferin substrate (Nanolight) at 120 mg/kg body weight, and images were quantified by measuring photons within a given region of interest, according to IVIS manufacturer instructions. Results are shown in FIGS. 9 and 10.

Success in the translation of rAAV gene therapy has been challenged by low transduction efficiency in vivo. This study employed structural analysis of the rAAV capsid to develop a rational engineering strategy that can clearly yield novel capsid variants with enhanced transduction phenotypes in skeletal muscle. The overall approach was made possible by earlier reports from our lab, which uncovered VR1 as a key determinant of transduction efficiency in rAAV2. As we had previously discovered in rAAV2, enhancement of transduction was observed with substations of various amino acids at position 265 in rAAV1. Remarkably, however, disruption of VR1 via the deletion of single amino acids in the more clinically relevant rAAV1 yielded novel vectors with transduction enhanced by orders of magnitude (FIG. 1). This observation alone has significant implications for patient dosing protocols currently utilizing rAAV1 and may lead to vector production easement moving forward. It was noted that in the rAAV6 capsid a similar outcome was obtained, but only after secondary mutations was created to disrupt the basic amino acid patch previously shown to confer heparin sulfate binding activity. Using a marker rescue approach made possible by analyzing capsid sequence homology, two distal regions of the capsid surface were defined that work in concert to modulate transduction efficiency and primary receptor recognition, shedding light on the complex role of capsid topology during the viral life-cycle.

The antagonistic relationship between position 265 and primary receptor binding suggests that the 265 deletion phenotype results from a modification in protein:protein interactions between the capsid and a binding partner. Whether this occurs at initial attachment to the cell surface or during a post entry event remains to be determined. That the only measurable correlation to transgene expression was an increase in the number of vector genomes per cell, and not in expression kinetics or longevity, strongly suggests that the 265 phenotype is a result of alterations in cellular entry phenomena. VR1 has been implicated in receptor binding in rAAV2, as well as in a chimeric vector generated via directed evolution, though explicit structural details of the nature of these interactions have not yet been defined. The spatial relationship of position 265 relative to the protrusions that comprise the three-fold axis of symmetry—the primary region of the capsid responsible for receptor engagement—lends further evidence to this idea. Of note, no differences were seen between wild-type and mutant constructs in 1.) heat denaturation assays testing capsid stability, 2.) Western blotting to examine the ratio and size of capsid proteins, or 3.) in electron microscopy to search for overt differences in capsid topology or population distribution of empty versus full capsids. Furthermore, dose response data suggest that the 265 enhanced transduction profile can be dialed in for respective clinical applications (e.g., AAT vs lipoprotein lipase deficiency).

It is well known that phosphorylation of threonine residues effects intracellular protein dynamics. Indeed, the phosphorylation of select serine, threonine and tyrosine residues on the rAAV capsid surface ultimately results in proteasomal clearance of capsids prior to transgene delivery and mutation of these residues to non-phosphorylable species prevents capsid clearance, thereby enhancing transduction efficiency. That multiple different types of amino acid at position 265 (deletion of threonine, substitution with phosphomimetics or bulky hydrophobics) all enhanced transduction suggests that phosphorylation is not likely responsible for transduction enhancements mediated by 265 mutation. Furthermore, the structure of VR1 could be disrupted throughout the loop to obtain an improved transduction phenotype. It is possible that these disruptions relieve the capsid from interacting with an inhibitory protein, though this has yet to he determined. However, there is evidence of a similar effect in rAAV2, in which ablation of capsid heparin binding ability substantially improves transduction of muscle tissue$^{((null)(null))}$. Indeed, such data was recapitulated in this work. It has been argued that the ability of rAAV2 to bind heparin sulfate proteoglycans has evolved through tissue culture adaptation of the virus and that binding to such receptors has been detrimental to the in vivo transduction efficiency of this serotype. Likewise, in the case of adenovirus, robust hepatic transduction is maintained even when the capsid is mutated to exclude binding to its primary tethering receptor, CAR, as alternate regions of the capsid are able to compensate by facilitating productive interactions with alternate receptors.

It is interesting that transduction efficiency peaked following deletion of position 265, specifically. In analyzing the hydrogen bonding network of VR1 in rAAV1 (FIG. 8A), it is noteworthy that VR1 is stabilized by a network of hydrogen bonds primarily orchestrated by position 265. Indeed, the next best transducers resulted from deletion of positions 264 and 263, both of which also participate in the structural stabilization of VR1 via this network. Of course, the only way to truly examine the effects of these mutations on the stability of VR1 would be through crystallographic resolution of these constructs. It is significant, however, that rAAV6 is inherently less stabilized around position 265 (FIG. 8B), and that in practice rAAV6 requires additional mutation to replicate the position 265 phenotype. Many studies have attempted to unravel the phenotypic disparity (e.g., differences in receptor preferences and tissue tropism) between the closely related rAAV1 and rAAV6. Virtually all previous studies have examined the six capsid amino acids that differ between these two viruses, with the understanding that pinpointing these locations allows dissection of capsid regions that directly influence the viral life-cycle. While this is true, we demonstrate here for the first time an additional, far more subtle layer of capsid architecture that differs on a structural level between these two serotypes to regulate viral biology, along with a rational design approach to exploit these attributes.

Another compelling finding is the discrepancy of measured transduction enhancement between rAAV1 and rAAV1/T265del when examining transgene expression within injected tissue directly (i.e., ex vivo luciferase assay, which produced 137-fold enhancement) versus measurement of transgene expression of a secreted protein (i.e., ELISA to determine the concentration of hAAT, which produced 9-fold enhancement). It is noteworthy that in previous experiments comparing the measurements of secreted hAAT from i.m. injected rAAV2, rAAV2.5 and AAV2/265D, no obvious differences were found by ELISA, despite order of magnitude increases in luciferase expression relative to rAAV2 when using the engineered capsids. Likewise, while it has been found that the proteasome inhibitor Bortezomib can enhance rAAV2 transduction in liver tissue by approximately 10-fold when measured by luciferase assay, that enhancement drops to less than 2-fold when measuring serum for the expression of secreted Factor IX. It is likely that measuring transgene expression directly from harvested tissue is a more sensitive technique than is the collection and subsequent measurement of secreted factors due to differences such as protein half-life within an intracellular environment versus serum, as well as overall efficiency of protein secretion relative to protein expression. Such findings highlight the exquisite increase in transduction that needs to be achieved for translatable applicability when designing rAAV vectors meant to deliver transgenes encoding secreted proteins.

The goal of these efforts is the continued improvement of rAAV vector technology so that gene therapy becomes a more practical and effective clinical choice, such as through reducing vector dosing required to achieve therapeutically beneficial transgene levels. Such efforts may allay clinical concerns around vector dose-dependent toxicity and ease clinical-grade vector production efforts. Here we present a simple and effective strategy for improving the performance of rAAV serotypes currently being used in clinical trials targeting skeletal muscle by direct injection. As this strategy utilizes a region of the capsid unique to other major advancements in rAAV vector development (e.g., the Tyr-to-Phe capsid mutants), it will be interesting to determine whether it can be integrated synergistically with such technological advancements to further optimize rAAV vectors for gene therapy. As we continue evaluating the potential of our 265 mutant panel to target and enhance transgene expression in cardiac tissue, as well as whole body skeletal muscle following systemic administration, the work contained herein provides a starting foundation for the development of next generation translational rAAV vectors. Furthermore, we have produced a collection of rAAV capsid reagents available for further detailed (e.g, crystallographic) analysis that will eventually lead to a more comprehensive understanding of the unique and significant role that single amino acids play in rAAV vector biology.

EXAMPLE 8

Materials and Methods

Plasmids and viruses: All plasmids were obtained from the University of North Carolina Gene Therapy Center Vector Core facility. Virus was made by way of triple transfection of HEK293 cells and purified by cesium chloride density ultracentrifugation, as previously described (Grieger et al., *Nat. Protoc.* 1(3):1412 (2006)). Viral titer was measured using real time quantitative PCR (qPCR) analysis, with the following primer set designed to recognize the luciferase transgene: (forward) 5'-AAA AGC ACT CTG ATT GAC AAA TAC-3' (SEQ ID NO:10) and (reverse) 5'-CCT TCG CTT CAA AAA ATG GAA C-3' (SEQ ID NO:11). For each experimental group, relevant viral constructs were titered together on the same qPCR plate prior to being used. Site-directed mutagenesis (Stratagene QuikChange) was used to create nucleotide deletions or substitutions. Table 9 lists the primer sequences used for all VR1 mutants created in this study. Prior to making virus, DNA sequencing was performed to verify that the sequence identity of each plasmid used in this work was correct.

TABLE 9

Site-directed mutagenesis primers used in this study.

| Construct | Primer Sequence (5' -> 3') |
|---|---|
| pXR1/T265del* | ctc cag tgc ttc agg ggc cag caa cg (SEQ ID NO: 27) |
| pXR1/T265D* | gca atc tcc agt gct tca gac ggg gcc agc aac g (SEQ ID NO: 13) |
| pXR1/Y445F* | cat cga cca gta cct gta ttt cct gaa cag aac tca (SEQ ID NQ: 2.8) |
| pXR2/Q263del | caa aca aat ttc cag ctc agg agc ctc g (SEQ ID NO: 29) |
| pXR2/S264del | caa art tcc agc caa gga gcc tcg aac g (SEQ ID NO: 3026) |
| pXR3b/Q263del | caa gca aat ctc cag ctc agg agc ttc (SEQ ID NO: 31) |
| pXR3b/266D | ctc cag cca atc aga cgg agc ttc aaa cg (SEQ ID NO: 32) |
| pXR3b/R594A | cag ctc cca cga ctg caa ctg tca atg atc (SEQ ID NO: 33) |
| pXR4/N261del | gag cct gca gtc cac cta caa cgg (SEQ ID NO: 34) |
| pXR5/258del | ccg tcg acg gaa acg cca acg cc (SEQ ID NQ: 35) |
| pXR6/S262del | gca aat ctc cgc ttc aac ggg gg (SEQ ID NO: 36) |
| pXR7/T265del | caa atc tcc agt gaa gca ggt agt acc (SEQ ID NO: 37) |
| pXR8/T265del | ctc caa cgg gtc ggg agg agc (SEQ ID NO: 38) |
| pXR8/T265D | caa atc tcc aac ggg gac tcg gga gcc acc (SEQ ID NO: 39) |

TABLE 9-continued

Site-directed mutagenesis primers used in this study.

| Construct | Primer Sequence (5' -> 3') |
|---|---|
| pXR8/S266del | tct cca acg gga cag gag gag cca acc (SEQ ID NO: 40) |
| pXR9/S263del | caa gca aat ctc cag cac atc tgg agg (SEQ ID NO: 41) |
| pXR9/S265del | ctc caa cag cac agg agg atc ttc aaa tg (SEQ ID NO: 42) |
| pXR9/T265D | caa cca aat ctc caa cag cga ctc tgg agg atc ttc aaa tg (SEQ ID NO: 43) |
| pXR9/S263A_S266del | gca aat ctc caa cgc cac agg agg atc ttc aaa tga c (SEQ ID NO: 44) |

*indicates that same primer sequence was used for pXR1 and pXR6 constructs

Structural analysis and molecular modeling: Indicated pdb files were processed through MolProbity structural validation software (molprobity.biochem.duke.edu) to add hydrogen bonds based on electron-cloud x-H bond lengths, using H-bond optimization via the inclusion of Asn/Gln/His flips where necessary. Files were then analyzed for all-atom contacts and geometry, and visualized in KiNG (kinemage.biochem.duke.edu) to determine VR1 atoms participating in hydrogen bonds. PDBs were then opened in PyMol (pymol.org), shown as stick diagrams with hydrogens visualized, and hydrogen bonds identified in KiNG were translated into dashed lines using the measure.

Live-animal studies: Animals were maintained and handled in accordance with National Institutes of Health guidelines, under protocols approved by the IACUC at the University of North Carolina, Chapel Hill. rAAV variants packaging the CBA-luciferase transgene were injected into the tail vein of 6-8 week old female BALB/c mice (Jackson Laboratories) at indicated quantities. All injections were performed in 200 μL total volume per injection (volume was brought to 200 μL using 1× PBS). Luciferase transgene expression was visualized using a Xenogen IVIS Lumina imaging system (Perkin Elmer/Caliper Life Sciences) following intraperitoneal injection of D-luciferin substrate (Nanolight) at 120 mg/kg body weight. Bioluminescent image analysis was performed using Living Image software (Perkin Elmer/Caliper Life Sciences).

Ex vivo quantification of transgene expression and copy number: To obtain tissue samples for analysis via ex vivo luciferase assay, mice were sacrificed at 10 dpi and indicated organs were harvested and flash frozen. Tissue was homogenized on ice using a razor blade, and approximately 50 mg of each tissue homogenate was then suspended in 250 μL of 2× Passive Lysis Buffer (Promega) and lysed mechanically using a Tissue Tearor (Cole-Parmer). 35 μL of each tissue lysate was then transferred to a 96-well plate and mixed with 100 μL of D-luciferin substrate (Promega) immediately prior to performing luminometric analysis using a Victor2 luminometer (Perkin Elmer). The total protein concentration of each tissue lysate was determined by Bradford assay (Bio- Rad). Additionally, a ~25 mg aliquot of the above generated tissue homogenate was processed using a DNeasy kit (Qiagen) to extract host and vector genomic DNA. The number of cells was determined using qPCR with the following primers designed specific to mouse Lamin (a housekeeping gene): (forward) 5'-GGA CCC AAG GAC TAC CTC AAG GG-3' (SEQ ID NO:45) and (reverse) 5'-AGG GCA CCT CCA TCT CGG AAA C-3' (SEQ ID NO:46). The number of viral genomes per cell was also determined using qPCR with primers designed specific to the luciferase transgene, as described above.

EXAMPLE 9

Structural Analysis of the rAAV Capsid to Identify Hydrogen Bond Networks in VR1

We have previously demonstrated that the deletion of select amino acids within VR1 of the rAAV1 capsid leads to log order increases in transduction efficiency following intramuscular injection into mice (Warischalk et al., *Mol. Ther.* 2015). Analysis of the rAAV1 crystal structure revealed that the most efficient VR1 deletion mutations corresponded to amino acids participating in intra-loop hydrogen bond networks, suggesting that the destabilization of VR1 structural elements leads to enhanced transduction phenotypes. The goal of the present study was to determine: 1) whether rAAV1 VR1 mutant capsids can efficiently target muscle tissue following intravenous injection (versus simply having a phenotype of enhanced transduction), and 2) whether the targeted destabilization of VR1 structural elements is a conserved method of improving transduction in additional rAAV serotypes. To address these questions, a collection of rAAV capsids including rAAV1, rAAV2, rAAV3, rAAV4, rAAV5, rAAV6, rAAV7, rAAV8, and rAAV9 were analyzed with the open source structural validation software MolProbity (Davis et al., *Nucleic Acids Res.* 35(Web Server issue):W375 (2007)) and VR1 hydrogen bond patterns visualized in KiNG (Chen et al., *Protein Sci.* 18(11):2403 (2009)) (FIG. 11A-11H). These serotypes were chosen for analysis based on the availability of both capsid crystal structure data (Govindasamy et al., *J. Virol.* 80(23): 11556 (2006); Miller et al., *Acta Crystallogr. Sect. F Struct. Biol. Cryst. Commun.* 62(Pt 12):1271 (2006); Xie et al., *Proc. Natl. Acad. Sci. USA*, 99(16):10405 (2002); Lerch et al., *Virology* 403(1):26 (2010); Govindasamy et al., *J. Virol.* 87(20):11187 (2013); Xie et al., *Acta Crystallogr. Sect. F Struct. Biol. Cryst. Commun.* 64(Pt 11):1074 (2008); Nam et al., *J. Virol.* 81(22):12260 (2007); Mitchell et al., *Acta Crystallogr. Sect. F Struct. Biol. Cryst. Commun.* 65(Pt 7):715 (2009)) and pre-existing knowledge of their in vivo transduction phenotypes (Zincarelli et al., *Mol. Ther.* 16(6): 1073 (2008)). There is no publicly available structural information for rAAV7; however, this serotype was included for the sake of completeness. For ease of visualization, identified hydrogen bond patterns were then translated into PyMol images (FIG. 12A-12H).

Based on these analyses, amino acids from each serotype that were found to participate in intra-loop VR1 hydrogen bond networks were selected for deletion. Table 10 lists the VR1 amino acid sequence for serotypes rAAV1-rAAV9 and the amino acids chosen for mutation in this study, as well as how many hydrogen bonds are hypothesized to be broken with each mutation. In the case of rAAV7, mutation of the threonine at position 265 was chosen based on previous results obtained for rAAV1 (Warischalk et al., *Mol. Ther.* 2015). In the case of rAAV9, the structure of VR1 appears to be stabilized by hydrogen bonds in two locations, the first primarily orchestrated by bonds originating around residue S263, and the second by bonds originating around residue S265. Therefore, mutant capsids comprising rAAV9/S263del and rAAV9/S265del were created, in addition to the double mutant rAAV9/S263del_S265del. However, the double deletion mutant was unable to produce intact viral particles, which led to the alternate strategy of mutating position S263 to an alanine in conjunction with deletion of position S265, to create rAAV9/S263A_S265del. For detailed atomic descriptions of the hydrogen bond relationships observed for all of the serotypes included within this study, refer to the legend for FIG. 11.

TABLE 10

Variable region 1 amino acid sequences and deletion mutations made in rAAV1-rAAV9.

| Serotype | Variable Region 1 | Mutations |
| --- | --- | --- |
| rAAV1 | $_{262}$SSASTGASNDNHY$_{273}$ (SEQ ID NO: 1) | T265del+++ |
| rAAV2 | $_{262}$SSQSGAS$_{268}$ (SEQ ID NO: 2) | Q263del+, S264del+ |
| rAAV3b | $_{262}$SSQSGASNDNHY$_{273}$ (SEQ ID NO: 3) | Q263del++ |
| rAAV4 | $_{256}$ESLQSNTY$_{263}$ (SEQ ID NO: 4) | N261del+ |
| rAAV5 | $_{252}$SGS VDGS$_{258}$ (SEQ ID NO: 5 ) | S258del++ |
| rAAV6 | $_{262}$SSASTGASNDNHY$_{273}$ (SEQ ID NO: 6) | S262del++, T265del+ |
| rAAV7 | n/a | T265del |
| rAAV8 | $_{263}$NGTSGGAT$_{270}$ (SEQ ID NO: 7) | T265del+ |
| rAAV9 | $_{261}$SNSTSGGSS$_{269}$ (SEQ ID NO: 8) | S263del++, S265del+, S263del_ S265del+++ |

+indicates number of hydrogen bonds hypothesized to be broken following mutation

EXAMPLE 10

Biodistribution of rAAV Capsids Mutated to Destabilize Hydrogen Bond Networks in VR1

To visualize tissue distribution and transduction efficiency of the above detailed wild-type and VR1 mutant capsids, each member of the collection was packaged with the chicken β-actin promoter driven firefly luciferase (CBA-luc) reporter transgene and injected into mice via the tail vein at a dose of 1e11 viral genomes (vg) per injection. Live-animal bioluminescent imaging was performed at 9 days post injection (dpi). At 10 dpi, mice were sacrificed and select organs removed, homogenized and lysed. Vector biodistribution was then quantified by subjecting tissue lysates to ex vivo luciferase assays in order to measure transgene expression, and qPCR analysis to quantify viral genome copy numbers per cell. The deletion of VR1 amino acids resulted in four phenotypes: 1) selective and robust targeting of cardiac and/or skeletal muscle, as observed for rAAV1 and rAAV6 (FIG. 13); 2) maintenance of innate cardiac and/or skeletal muscle transduction efficiency, coupled with a substantial reduction in transduction of the liver, as seen in rAAV7, rAAV8, and rAAV9 (FIG. 14); 3) a widespread absence of transduction, as in rAAV2 and rAAV3 (FIG. 15A-15B); and, 4) the inability to produce intact viral particles, as in the case of rAAV4 and rAAV5.

VR1 mutations in rAAV1 and rAAV6 capsids led to substantial gains in transduction efficiency in cardiac and skeletal muscle tissues (FIG. 13). Transgene expression measured 21-fold higher in cardiac and 26-fold higher in gastrocnemius (GC) tissue samples taken from mice treated with rAAV1/T265del versus rAAV1. rAAV1/T265del transduction efficiency was also enhanced in several other tissue types, including the diaphragm (26-fold), the spleen (3.5 fold), the kidney (5-fold), the pancreas (6-fold), and the lung (8-fold), (FIG. 16A). Surprisingly, there was a 3.5-fold decrease in hepatic transduction relative to rAAV1 (FIG. 13B). Similarly, rAAV6/T265del capsids transduced cardiac and GC muscle at levels 14-fold and 3-fold higher then wild-type rAAV6, concomitant with a 28-fold decrease in transduction of the liver (FIG. 13E). There were no remarkable differences in measured transgene expression between rAAV6 and rAAV6/T265del capsids in any other tissue tested (FIG. 16B). rAAV6/S262del produced a similar phenotype to rAAV6/T265del, transducing at levels 3.5-fold lower and 6-fold higher then rAAV6/T265del in cardiac and GC muscle, respectively, and within 1-fold of rAAV6/T265del in the liver (FIG. 16C). These results suggest that rAAV1 and rAAV6 VR1 mutant constructs preferentially transduce muscle tissue when systemically administered to mice.

The numbers of vector genomes present per host cell were quantified via qPCR on a subset of organs including the heart, GC, and liver (FIG. 13C, 13F). In tissue samples obtained from mice treated with rAAV1/T265del and rAAV6/T265del capsids, changes in host cell transgene populations measured by qPCR trended similarly to those observed for transgene expression measured by luciferase assay (i.e., more vector genomes correlated with increased transgene expression, and vice-versa). However, differences amongst transgene population measurements were more subtle than those obtained for transduction efficiency. For example, in mice treated with rAAV6/T265del there were 4-fold more vector genomes per heart cell than in mice treated with rAAV6, whereas there was a 14-fold increase in cardiac transduction with the mutant capsid (FIG. 13F). Likewise, there were 4-fold fewer rAAV6/T265del genomes per liver cell, versus a 28-fold decrease in transduction. Intriguingly, vector genomes per cardiac cell were substantially lower than those measured per liver cell in the case of both rAAV1 and rAAV1/T265del, despite that transduction of the heart was far greater than that of the liver in both constructs. Collectively, these data indicate that the reduced ability of rAAV1 and rAAV6 VR1 mutant capsids to transduce the liver corresponds with an inability of these capsids to deliver a persistent transgene to hepatic cells. Additionally, transgenes delivered by VR1 mutant capsids to muscle tissues appear to be more effectively expressed than those delivered by their wild-type counterparts. Finally, it would appear that some facet of the liver's microenvironment imposes a hurdle towards the rAAV1 capsid's ability to either enter the nucleus or uncoat once there.

Figures 14G, 14H, 14I:
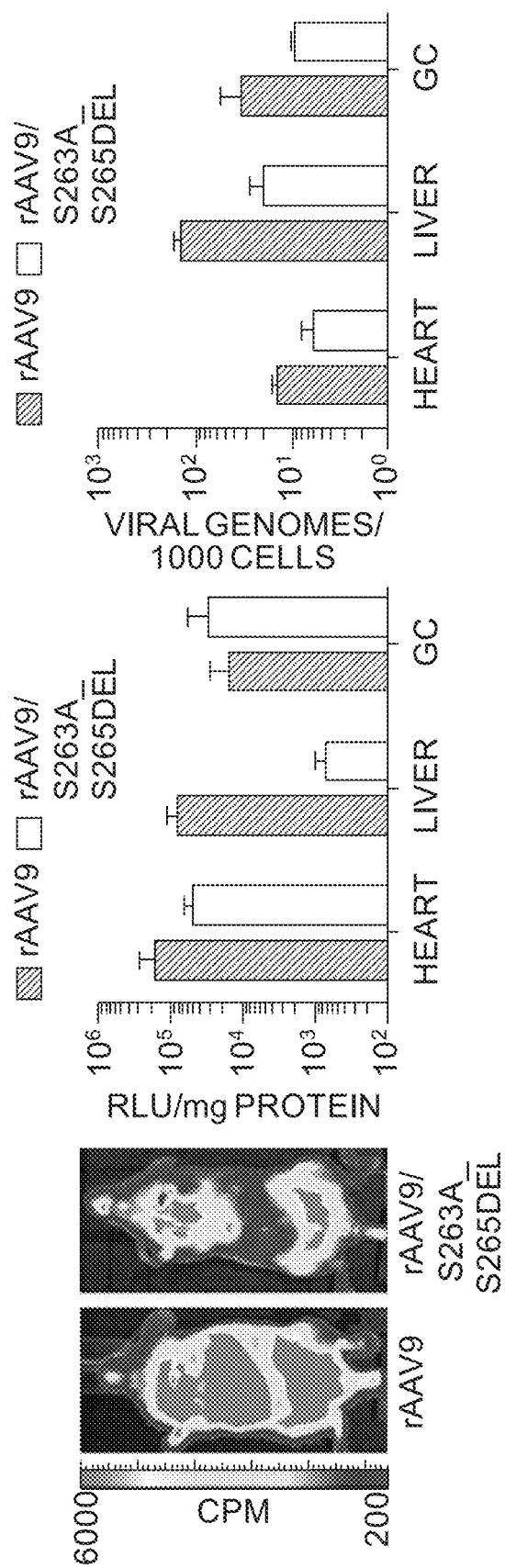

Deleting VR1 amino acids from rAAV7, rAAV8 and rAAV9 capsids created biodistribution profiles with strikingly similar phenotypes (FIG. 14A, 14B, 14G). The primary feature observed for each was a sharp reduction in hepatic transduction (427-fold in rAAV7, 23-fold in rAAV8 and 107-fold in rAAV9 relative to wild-type capsids), while native cardiac and skeletal muscle transduction levels were maintained. Transduction efficiency in muscle tissue did not markedly change between rAAV7 and rAAV7/T265del; however, rAAV8/T265del enhanced transduction efficiency in GC tissue by approximately 8-fold relative to rAAV8 (FIG. 14E). rAAV9/S263del_S265del produced variable effects in muscle tissue, transducing cardiac tissue 3-fold lower and GC tissue 2-fold higher than rAAV9 (FIG. 14H). There were no prominent transduction differences between VR1 mutant and wild-type capsids of this subset in any other tissue type sampled (FIG. 174-17C). It is notable that simultaneous mutations at positions S263 and S265 were required to produce a muscle-targeted biodistribution profile in rAAV9, and that single deletions at either of these positions substantially reduced overall transduction efficiency (FIG. 14D).

The numbers of vector genome copies present per host cells were quantified in cardiac, GC and hepatic tissue samples. In all VR1 mutant capsids of this subset, reduced hepatic transgene expression corresponded to reduced transgene populations within liver cells (85-fold fewer vector genomes per liver cell for rAAV7/T265del, 27-fold fewer for rAAV8/T265del and 7-fold fewer for rAAV9/S263del_S265del; FIG. 14C, 14F, 14I). The relationship between transgene population and transduction efficiency was less clear in muscle tissue samples. For example, there was a 22-fold reduction in transgene copies per cardiac cell when comparing rAAV7/T265del to rAAV7, yet transduction efficiency between the capsids was virtually the same. These data suggest that VR1 mutant capsids of this subset are deficient in the ability to deliver a stable transgene population to hepatic cells, while transgenes delivered by these capsids to muscle tissues are more effectively expressed than those delivered by their wild-type counterparts.

Figure 15A:
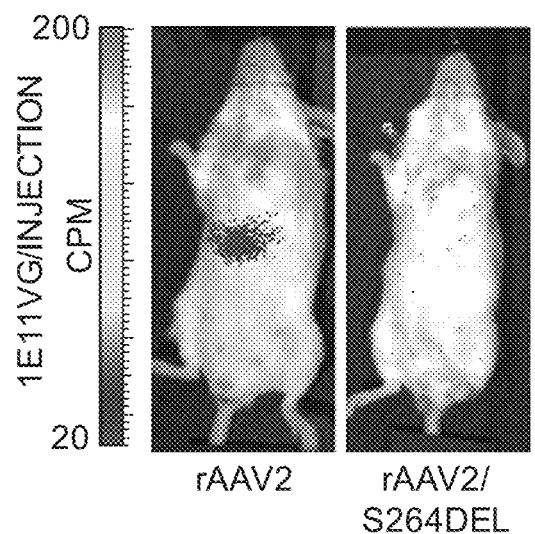
Figure 15B:
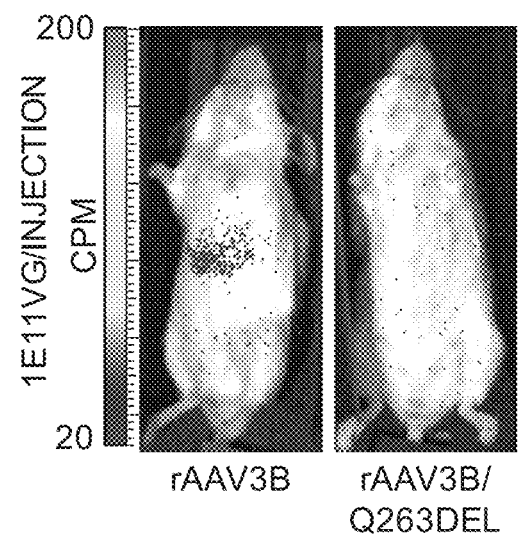
Figure 15C:
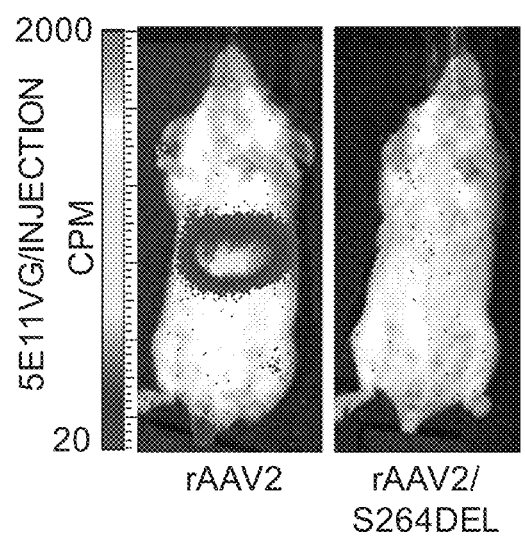
Figure 15D:
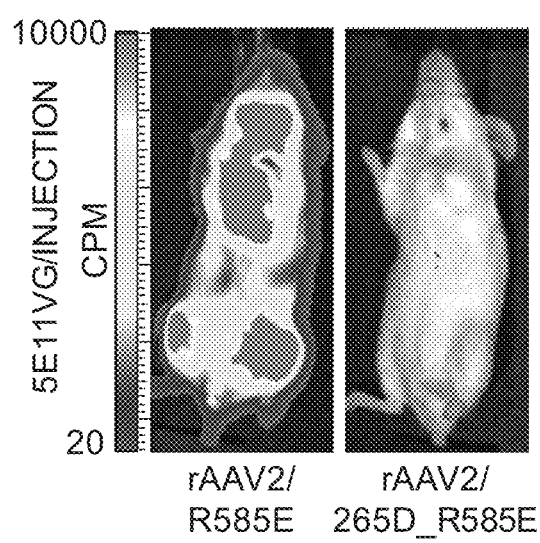

The deletion of VR1 amino acids produced deleterious effects in rAAV2, rAAV3b, rAAV4 and rAAV5 capsids. In rAAV4 and rAAV5, VR1 amino acid deletions led to an inability to produce intact virions. Vector production was attempted several times with both constructs to verify the repeatability of this result. In rAAV2 and rAAV3b, VR1 amino acid deletions had no measurable impact on vector production however, in both of these serotypes VR1 deletion mutations resulted in the elimination of measurable transduction in mice following intravenous injection (FIG. 15A-15B). Again, to verify the repeatability of these results, these experiments were duplicated with fresh stocks of vector in a second cohort of mice at a 5-fold higher dose (5e11vg/injection) of rAAV2 and rAAV2/S264del (FIG. 15C). Overall, the dramatic effects observed in these serotypes in response to VR1 deletion mutations suggests that maintaining a defined VR1 structure is critical towards these capsids' abilities to complete a productive viral life-cycle.

EXAMPLE 11

Identification of a Capsid Motif that Enables Highly Efficient Hepatic Transduction Previous studies have demonstrated that rAAV2 capsids harboring amino acid insertion mutations following position 264 in the capsid protein (creating a de novo position 265) exhibit markedly enhanced transduction efficiency in skeletal muscle following intramuscular injection (Bowles et al., *Mol. Ther.* 20(2):443 (2012); Li et al., *J. Virol.* 2012. 86(15):7752 (2012)). The insertion of aspartic acid in particular (rAAV2/265D) has been found to enhance transduction by orders of magnitude (Li et al., *J. Virol.* 2012. 86(15):7752 (2012)). As the deletion of VR1 amino acids rendered rAAV2 capsids incapable of transduction, we next examined whether the alternative—the insertion of amino acids into VR1—could enhance the biodistribution phenotype of rAAV2. rAAV2 and rAAV2/265D capsids packaging CBA-luc were injected into the tail vein of mice and live animal bioluminescent imaging was performed at 9 dpi (FIG. 18A). At 10 dpi organs were harvested and quantified for transgene expression, as described above. Intriguingly, while VR1 amino acid deletions in other serotypes led to sharp reductions in hepatic transduction, the insertion of additional amino acids into VR1 led to an opposite phenotype. Hepatic transduction was increased by 10-fold in rAAV2/265D relative to rAAV2 (FIG. 14B), while transduction differences between the two capsids differed by ≤2-fold in all other tissues studied (FIG. 14B and FIG. 15A). Vector genome copies per host cell differed by less than 1-fold between the two capsids in heart and GC tissues; however, there was a 10-fold increase in vector genome copies per liver cell in mice administered rAAV2/265D versus rAAV2 (FIG. 18C). Thus, rAAV2/265D capsids are either more capable of targeting to and entering liver cells than are rAAV2 capsids, or the genomes delivered by these mutant capsids are better able to persist within these cells (or both).

Figure 19A:
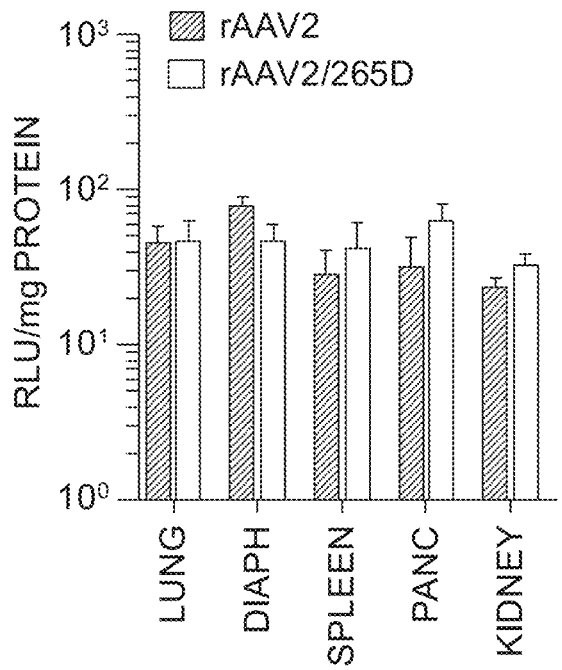
Figure 19B:
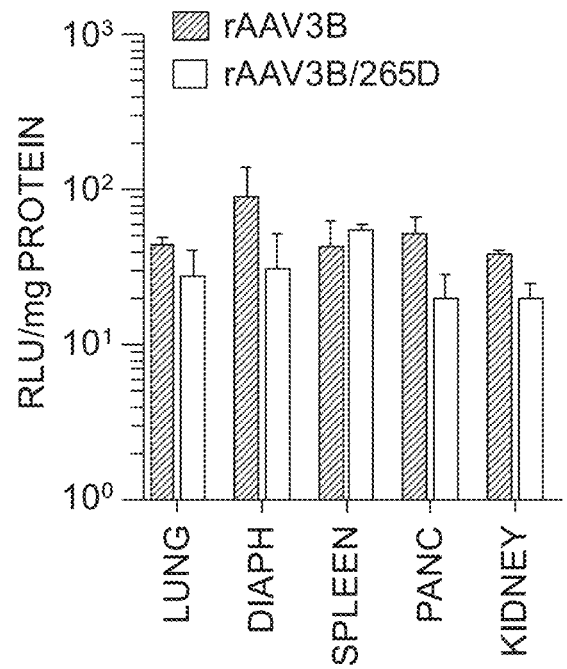
Figure 19C:
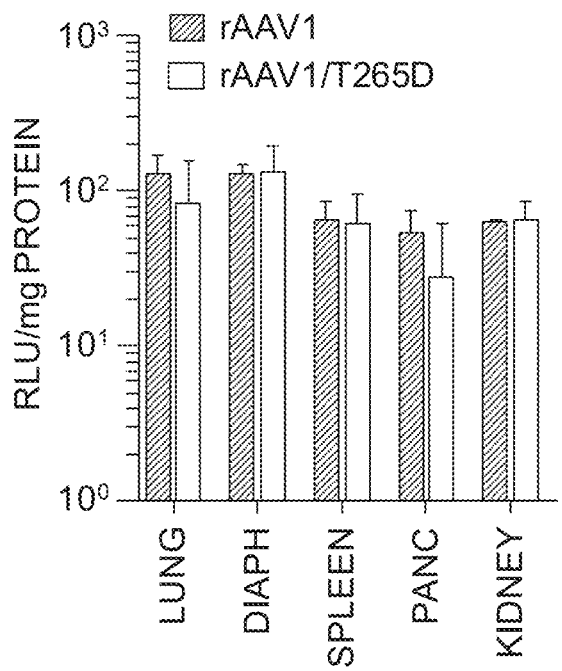
Figure 19D:
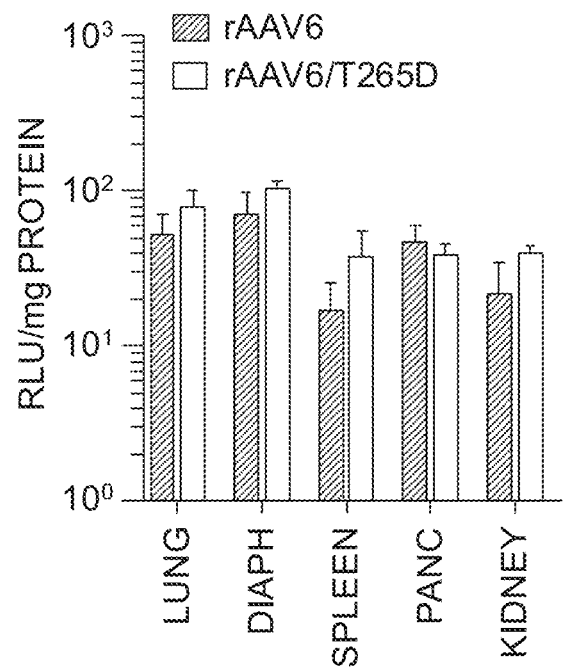

To determine whether the presence of an aspartic acid in VR1 could enhance hepatic transduction in additional serotypes, substitution mutations (Table 11) were made in rAAV1 (rAAV1/T265D) and rAAV6 (rAAV6/T265D), and an insertion mutation was made in rAAV3b (rAAV3b/265D). In all cases, a strong transduction preference for the liver was observed: rAAV1/T265D transduced the liver by approximately 212.5-fold higher than rAAV1 (FIG. 18H), rAAV6/T265D by 28-fold relative to rAAV6 (FIG. 18K), and rAAV3b/265D by 9-fold relative to rAAV3b (FIG. 18E). In the case of rAAV1 and rAAV1/T265D, transduction differences between the two constructs differed by 2.5-fold or less in all other tissues examined (FIG. 18H and FIG. 19C). rAAV6/T265D enhanced transduction of cardiac and GC muscle relative to rAAV6 by 32- and 4.5-fold, respectively (FIG. 18K). In all remaining tissues, transduction efficiencies of the two constructs were virtually identical (FIG. 19D). Finally, when comparing the biodistribution of rAAV3b and rAAV3b/265D, the mutant construct enhanced transduction by approximately 3-fold in cardiac and diaphragm tissues, while no remarkable transduction differences between the two constructs were observed in any remaining tissues (FIG. 18E and FIG. 19B). Taken together, the data show that the insertion or substitution of aspartic acid into VR1 preferentially enhances hepatic transduction following intravenous administration of rAAV.

TABLE 11

Variable region 1 amino acid sequences and aspartic acid insertion and substitution mutations made in select rAAV capsids.

| Serotype | Variable Region 1 | Mutations |
|---|---|---|
| rAAV1 | *<br>$_{262}$SSASDGASNDNHY$_{273}$<br>(SEQ ID NO: 1) | T265D |
| rAAV2 | *<br>$_{262}$SSQSDGAS$_{268}$<br>(SEQ ID NO: 2) | 265D |
| rAAV3b | *<br>$_{262}$SSQSDGASNDNHY$_{273}$<br>(SEQ ID NO: 3) | 266D |
| rAAV6 | *<br>$_{262}$SSASDGASNDNHY$_{273}$<br>(SEQ ID NO: 6) | T265D |
| rAAV 8 | *<br>$_{263}$NGDSGGAT$_{270}$<br>(SEQ ID NO: 7) | T265D |
| rAAV9 | *<br>$_{261}$SNSDSGGSS$_{269}$<br>(SEQ ID NO: 8) | S265D |

Bolded text indicates conserved primary amino acid sequence; asterisks highlight aspartic acid mutations.

To determine if transduction efficiency correlated with genome copy number within each tissue, vector genome copies per host cell were quantified for heart, liver, and GC tissue samples. There were increased numbers of vector genomes present in the livers of mice treated with rAAV1/T265D and rAAV3b/265D relative to wild-type counterparts (4.5-fold and 182-fold, respectively; FIG. 18F, 18I). In the case of rAAV6, vector genome copies per liver cell were virtually identical between wild-type and mutant capsids (FIG. 18I). VR1 aspartic acid imitations also substantially enhanced the number of vector genome copies per GC cell in mice treated with rAAV1/T265D or rAAV3b/T265D (60-fold and 51-fold more genomes than wild-type, respectively; FIG. 18F, 18I, 18L), though transduction efficiencies between mutant and wild-type constructs in this tissue type were identical (in either case, values measured within 2-fold of those obtained for wild-type capsids). The lack of consistent correlation between vector genome copy numbers and transduction efficiencies strongly suggests that post entry processing of viral capsids is at least partially responsible for driving the enhanced liver transduction efficiencies of these mutant capsids.

While rAAV1, rAAV2, rAAV3b and rAAV6 capsids were made to contain the same SSXSDGAS (SEQ H) NO:47) VR1 amino acid sequence following 265D mutation, rAAV8 and rAAV9 have substantially different amino acid sequences in this region of the capsid (Table 11). Therefore, to clarify whether the enhanced preferential liver transduction produced by capsids bearing a 265D mutation was due to primary amino acid sequence versus some electrostatic or structural effect imparted by aspartic acid itself, 265D mutations were made in rAAV8 and rAAV9 capsids. rAAV8/T265D and rAAV9/T265D capsids packaging CBA-luc were produced in tandem with rAAV8 and rAAV9, and all were intravenously injected into mice. Bioluminescent imaging was performed at 10 dpi. In rAAV8 and rAAV9 capsids, the T265D mutation substantially reduced overall transduction efficiency relative to wild-type capsids (FIG. 20). These results suggest that the SSXSDGAS (SEQ ID NO:48) VR1 amino acid sequence is the driving force behind enhanced hepatic transduction efficiency in the relevant rAAV capsids, and not a structural feature imparted by aspartic acid itself.

EXAMPLE 12

Impact of Capsid Heparin Binding Ability on Transduction Efficiency of VR1 Mutant Capsids We have previously demonstrated that the ability of a given capsid to bind to heparin sulfate impedes the enhanced transduction phenotype produced by VR1 mutation in capsids administered via intramuscular injection (Warischalk et al., *Mol. Ther.* 2015). It has been previously shown that heparin binding can be disrupted in rAAV2, rAAV3b, and rAAV6 through single point mutations in each capsid (Kern et al., *J. Virol.* 77(20):11072 (2003); Opie et al., *J. Virol.* 77(12):6995 (2003); Lerch et al., *Virology,* 423(1):6 (2012); Wu et al., *J. Virol.* 80(22):11393 (2006)). Therefore, to determine whether VR1 mutant capsid transduction efficiency could be further enhanced, these mutations were incorporated into rAAV2, rAAV3b, and rAAV6 to create rAAV2/R585E, rAAV3b/R594A, and rAAV6/K531E. The inability of these mutant capsids to interact with heparin was verified using heparin affinity chromatography. The above capsids were packaged with CBA-luc and intravenously administered to mice in tandem with rAAV2/265D_R585E, rAAV3b/265D_594A, and rAAV6/T265D_K531E and their single mutant and wild-type counterparts. At 10 dpi, mice were sacrificed and livers removed for quantitation of transgene expression. As has been previously shown (Asokan et al., *Nat. Biotechnol.* 28(1):79 (2010); Kern et al., *J. Virol.* 77(20):11072 (2003)), impairing heparin binding from the rAAV2 capsid decreased hepatic transduction in mice by about 6.5-fold (FIG. 21A). However, when combining this heparin-null rAAV2 capsid with the VR1 mutation 265D, the resultant rAAV2/265D_R585E outperformed both rAAV2 and rAAV2/265D in the liver by 132- and 11-fold, respectively (FIG. 21A). Impairing capsid heparin binding ability in rAAV3b and rAAV6 in combination with the VR1 265D mutation also enhanced transduction compared to the respective parent capsids. rAAV3b/265D_R594A transduced the liver by 53-fold over rAAV3b and 2.5-fold over rAAV3b.265D, while rAAV6/T265D_K531E was respectively 46-fold and 4-fold more efficient than rAAV6 and rAAV6/T265D (FIG. 21B, 21C). Finally. because VR1 deletion mutations applied to rAAV6 capsids enhanced transduction efficiency in muscle tissue (unlike similar mutations in rAAV2 and rAAV3b which became transduction deficient following VR1 amino acid deletions), we also sought to determine whether nullification of rAAV6 heparin binding would serve to further increase transduction within this context. Individual mice were administered 1e11vg of rAAV6, rAAV6/T265del, rAAV6/K531E or rAAV6/T265del_K531E. At 10 dpi, mice were sacrificed and heart and GC samples removed to determine ex vivo luciferase expression. As with rAAV6/T265D, above, abrogation of rAAV6 capsid heparin binding ability further enhanced the transduction efficiency of rAAV6/T265del. rAAV6/T265del_K531E was 170-fold and 13-fold more efficient at transducing cardiac tissue than rAAV6 and rAAV6/T265del, respectively, 9027-fold and 2795-fold more efficient than each in GC tissue (FIG. 21D). Taken together, these studies indicate that in order to optimize the transduction efficiency of VR1 mutant capsids, it is necessary to ensure that capsid heparin binding capabilities are removed from the applicable serotypes.

EXAMPLE 13

Transduction of VR1 Mutant Capsids Relative to Most Efficient Wild-Type Serotypes When delivered intravenously into mice, rAAV8 and rAAV9 are generally considered to be the most efficient serotypes at transducing hepatic and cardiac tissue, respectively (Bish et al., *Hum. Gene Thur.* 19(12).1359 (2008); Davidoff et al., *Mol. Ther.* 11(6):875 (2005)). Therefore, to adequately assess the in vivo performance of our collection of VR1 mutant capsids within the context of existing reagents, capsids bearing VR1 deletion mutations and those bearing VR1 insertion mutations were evaluated in tandem with rAAV9 and rAAV8, respectively. rAAV1/T265del, rAAV6/T265del, rAAV6/T265del_K531E, rAAV7/T265del, rAAV8/T265del, rAAV9/S264del_S266del and rAAV9 capsids packaging CBA-luc were produced concurrently and titered together in the same reaction plate via qPCR. Mice were individually injected with 1e11vg of each construct, and sacrificed at 10 dpi to collect heart and liver tissue samples for quantitative analysis. Liver tissue was collected in addition to heart as a measure of vector specificity. rAAV1/T265del, rAAV6/T265del, rAAV6/T265del_K531E, and rAAV7/T265del each transduced the heart at levels identical to rAAV9, while rAAV8/T265del was approximately 5-fold more efficient than rAAV9 and rAAV9/S263A_S265del approximately 3-fold less efficient (FIG. 22A). We next wanted to determine whether our mutants preferentially transduced cardiac tissue over other organs such as the liver. All VR1 mutant capsids exhibited greater cardiotropism than rAAV9 (FIG. 22B, 22C), with the exception of rAAV8/T265del, which transduced the liver at an equivalent level as rAAV9. rAAV6/T265del produced the most promising cardiotropic profile, transducing the heart approximately 582 times more efficiently than the liver (FIG. 22C) versus rAAV9, which transduced the heart only 2-fold more efficiently than the liver. Collectively, these data present six new reagents with a more favorable cardiotropism than rAAV9.

To assess the ability of our 265D mutant capsid panel to transduce the liver relative to rAAV8, rAAV1/T265D, rAAV2/265D_R585E, rAAV3b/265D_R594A, and rAAV6/T265D_K531E vectors packaging CBA-luc were produced in tandem with rAAV8. All constructs were titered on the same qPCR plate and injected into mice at a dose of 1e11vg. Mice were sacrificed at 10 dpi and samples of liver tissue removed for analysis. None of the 265D mutant capsids reached the transduction efficiency of rAAV8, though rAAV2/265D_R585E came within <3-fold (FIG. 22D). rAAV1/T265D and rAAV6/T265D_K531E each transduced the liver approximately 8-fold less efficiently than rAAV8, and rAAV3b/265D_R594A by approximately 17-fold less efficiency (FIG. 22D). Collectively, these results show that while the insertion or substitution of an aspartic acid residue into VR1 can substantially enhance hepatic transduction efficiency in numerous serotypes, rAAV8 is still superior in transduction of the liver in this mouse model.

EXAMPLE 14

Cardiotropism of VR1 Mutant Capsids is Enhanced by Incorporation of Y→F Mutations Mutation of select tyrosine residues on the rAAV capsid surface has been shown to enhance rAAV transduction efficiency by avoiding the phosphorylation and ultimate proteasomal degradation of intracellular capsids before they are able to reach the nucleus (Zhong et al., *Virology* 381(2): 194 (2008)). We wanted to determine if these mutations could synergize with VR1 mutant capsids to enhance transduction efficiency while maintaining the biodistributive phenotypes imparted by VR1 mutation. As rAAV1 has been the most utilized serotype for translational human studies aimed at correcting cardiac and skeletal muscle disease (Flotte et al., *Hum. Gene Ther.* 22(10):1239 (2011); Greenberg et al., *JACC Heart Fail.* 2(1):84 (2014)), an rAAV1 capsid was created to include both Y445F and T265del mutations. Though tyrosine-to-phenylalanine mutations have not been previously evaluated in the context of rAAV1, Y445F has been proven to enhance transduction efficiency in rAAV6 following intramuscular injection (Qiao et al., *Hum. Gene Ther.* 21(10):1343 (2010)). rAAV1 and rAAV6 have >99% homology in capsid protein sequence (Wu et al. *J. Virol.* 80(22):11393 (2006)), thus it was reasonable to expect that this mutation may function similarly in the context of rAAV1. Nevertheless, rAAV6 was also included in this analysis. Wild-type rAAV1 and rAAV6 capsids packaging CBA-luc were produced concurrently with single and double T265del and Y445F mutant capsids. Mice were injected via the tail vein with 1e11vg of each, and heart, liver, and GC tissue samples were removed at 10 dpi for analysis. In both serotypes, the double T265del_Y445F mutant capsids further improved cardiac transduction efficiency: rAAV1/T265del_Y445F transduced the heart 66-fold and 9-fold higher than rAAV1 and rAAV1/T265del (FIG. 23A), respectively, while rAAV6/T265del_Y445F transduced 30-fold and 3-fold higher than rAAV6 and rAAV6/T265del. The double T265del_Y445F mutation led to variable effects in GC tissue, wherein transduction was enhanced by 3.5-fold in rAAV6/T265del_Y445F versus rAAV6/T265del (FIG. 23B), and was virtually the same between the rAAV1 counterpoints to these mutants. In both serotypes the liver detargeting imparted by the VR1 mutant capsids was wholly maintained in the context of Y445F mutation. Curiously, the Y445F mutant alone could not enhance the transduction efficiency of either rAAV1 or rAAV6 following intravenous delivery, despite the fact that in cell culture experiments the mutant enhanced transduction markedly over wild-type capsids. To our knowledge, these mutants have not been previously evaluated following intravenous injection into mice and thus it is difficult to speculate why they would not outperform their parental counterparts via this route of delivery. Perhaps a tyrosine residue at position 445 is required for successful trafficking across barriers imposed by blood vasculature. Altogether, these data suggest that incorporating Y445F into VR1 mutant capsids can further enhance cardiac transduction while maintaining a liver-detargeted biodistribution profile.

We present here a novel capsid engineering method that can be used to improve the targeting and transduction of muscle tissue in systemically delivered rAAV. Previous observations have shown that disrupting the stability of rAAV1 capsid loop VR1 via the deletion of select amino acids significantly enhanced skeletal muscle transduction following intramuscular injection (Warischalk, J. K. a. S., *Mol. Ther.* 2015). The mutations most efficient at enhancing transduction correlated to those that were most disruptive to VR1 intra-loop hydrogen bond networks. These observations led us to probe whether the targeted destabilization of VR1 in rAAV1 could induce preferential targeting of muscle tissue following intravenous administration, and whether this approach could be used to engineer additional rAAV serotypes towards producing a similar outcome. Our strategy was effective in enhancing the biodistributive properties of five of the nine serotypes studied. In rAAV1 and rAAV6 capsids, a robust gain of function in transducing cardiac and/or skeletal muscle tissues was observed, while in rAAV7, rAAV8, and rAAV9 capsids, native transduction levels were maintained in muscle tissue while liver transduction efficiency was dramatically decreased. Significant deleterious effects following VR1 mutation were noted in the remaining serotypes, including the inability to produce intact virions in rAAV4 and rAAV5 and severe transduction deficiencies in rAAV2 and rAAV3b. Thus, our method provides functional insights into capsid topology that can either be systematically incorporated or avoided when designing novel vectors.

Intra-protein hydrogen bond networks regulate functionality and structural dynamics in virtually every class of proteins, including numerous viral species (for example, see Worth et al., *BMC Evol. Biol.* 10:161 (2010)). However, barring the acquisition of empirical structural data, only correlative evidence currently supports that hydrogen bond destabilization is the driving force behind the improved phenotypes of the VR1 mutant capsids created in this study. Nonetheless, the evidence does provide reasonable support of the hypothesis. First, the strategy worked as intended in the majority of serotypes tested. Second, rAAV6 residues S262 and T265 form a hydrogen bond pair that works together to stabilize the rest of VR1 (FIG. 11F), and the individual deletion of either of these residues resulted in equivalent biodistributive phenotypes (FIG. 16C). Third, VR1 stability appears to depend on two different sets of hydrogen bond partners in rAAV9 (FIG. 11H), and the desired muscle-tropic biodistribution phenotype could only be obtained following mutation of both of them (FIG. 14G); individual mutations of either residue were ineffective (FIG. 17D). Finally, in rAAV8 only a single hydrogen bond exists in VR1: that of the position T265 amino acid side chain hydrogen bonding to itself (FIG. 11G). While the deletion of T265 resulted in substantial detargeting of the liver (FIG. 14E), the removal of the neighboring S266 did not (FIG. 24). Coupled with the destructive effects that VR1 destabilization has on rAAV2, rAAV3b, rAAV4 and rAAV5, the evidence suggests that a precisely defined structure for this capsid loop is highly influential to the productive advancement of rAAV through its life-cycle.

While disruptions to VR1 structure clearly result in vectors with enhanced systemic properties, further details behind the mechanism governing these novel phenotypes remain elusive. Individual hydrogen bond pairs have been found to control capsid stability and infectious efficiency in diverse viral species (Tipper et al., *J. Virol.* 88(18):10289 (2014); Tso et al., *J. Mol. Biol.* 426(10):2112 (2014); Rue et al., *J. Virol.* 77(14):8009 (2003); Speir et al., *J. Virol.* 80(7):3582 (2006)) and have additionally been hypothesized to modulate rAAV assembly (Grieger et al., *J. Virol.* 80(11): 5199 (2006)). However, an established heat dissociation protocol designed to measure rAAV capsid stability (Horowitz et al, *J. Virol.* 87(6):2994 (2013)) revealed no differences between wild-type and VR1 mutant capsids. Furthermore, a simple increase in capsid dissociability seems unlikely to result in broad changes to vector biodistribution. The VR1 loop of rAAV lies at an interface between monomeric subunits on the exposed capsid surface and can therefore potentially interact with additional proteins. Intra-capsid hydrogen bond networks are known to modulate capsid interactions with binding partners, such as during glycan catalysis by influenza neuraminidase (von Grafenstein et al., J. Biomol. Struct. Dyn. 33(1):104 (2015)), receptor engagement by human poly omavirus (Khan et al., J. Virol. 88(11): 6100 (2014)), and evasion of the anti-viral factor TRIM5α by HIV-2 (Miyamoto et al., PLoS One 6(7):e22779 (2011)). VR1 mutation may therefore alter capsid stability so as to prevent capsid interactions with a preferred cell surface receptor, enabling an alternate entryway into the nucleus. The consistent reduction in hepatic vector genome populations of mice administered VR1 deletion mutant capsids supports this notion, as does the finding that vector genomes delivered to cardiac cells by mutant capsids were far more efficiently expressed than those delivered by wild-type counterparts. Furthermore, this concept is not without precedent, as rAAV2 exhibits improved muscle targeting and decreased liver transduction when the capsid is mutated to eliminate heparin binding (Asokan et al., *Nat. Biotechnol.* 28(1):79 (2010); Kern et al., *J. Virol.* 77(20):11072 (2003)). rAAV9 also exhibits a liver-detargeted, systemically enhanced phenotype when mutated to reduce galactose binding (Shen et al., *J. Virol.* 86(19):10408 (2012)). It is notable that VR1 mutations have been shown to reduce the ability of rAAV2 and rAAV6 capsids to bind to heparin sulfate (Warischalk et al., *Mol. Ther.* 2015). Additionally, the N-terminal region of VR1 is positioned on the capsid in close enough proximity (<3 A) to the galactose-binding footprint of rAAV9 that direct interactions between the two regions are feasible (Bell et al., *J. Virol.* 86(13):7326 (2012)). Such observations bring up intriguing questions as to whether receptors identified for different rAAV serotypes in vitro are potential artifacts from passaging through cell culture, and whether rAAV could have a far greater in vivo transduction potential than previously believed if such artifacts are mutationally ablated.

From a structural perspective, the observation that VR1 deletion mutations render rAAV4 and rAAV5 incapable of producing intact virions is straightforward. In both of these serotypes, VR1 forms a relatively short loop that is primarily hydrogen bonded to underlying B-sheets. Therefore, disrupting the stability of this region of the capsid could conceivably result in gross structural changes that prevent capsid monomers from interacting with each other. Understanding why VR1 deletion mutations render rAAV2 and rAAV3b as transduction deficient is less clear. Despite being unable to transduce mouse tissues, rAAV2/S264del and rAAV3b/S262del are able to transduce cells in culture. Therefore, any deficiencies in the transduction of mouse tissues stems from some facet of the in vivo environment. Future experiments aim to dissect these observations further. The failure to improve rAAV2 through VR1 amino acid deletions was not without merit, however, as it led to the serendipitous discovery that insertions of aspartic acid into VR1 produce the opposite phenotype of deletion mutations: robust enhancement of hepatic transduction following systemic administration of vector. The mechanistic details governing the behavior of VR1 insertion mutants are currently unknown. Aspartic acid is a known phosphomimetic and could therefore potentially redirect capsid trafficking within the cell. Indeed, serine and threonine phosphorylation has been suggested to tag rAAV capsids for proteasomal degradation (Gabriel et al., *Hum. Gene Ther. Meth.* 24(2):80 (2013)). However, open source phosphorylation-site prediction software (NetPhos2.0) does not indicate VR1 (either modified or unmodified) as a site of phosphorylation, and data from cell culture experiments utilizing proteasome inhibitor do not support that the phenotype of 265D mutant capsids is a result of reduced proteasomal clearance. Another possibility is that aspartic acid insertion into VR1 produces the opposite effect of amino acid deletion: stabilizing the structure of VR1 as opposed to destroying it. Aspartic acid residues are well known for their stabilizing effect on protein structure through participation in intra-protein interactions such as carbonyl stacking (Deane et al., *Protein Eng.* 12(12): 1025 (1999)), salt bridges (Speare et al., *J. Biol. Chem.* 278(14):12522 (2003)), and hydrogen bond networks (Worth et al., *BMC Evol. Biol.* 10:161 (2010)). If this were true, it is conceivable that while VR1 deletion mutations destabilize this region of the capsid so as to prevent interaction with a given receptor, aspartic acid insertions into VR1 instead enhance both capsid structural stability and resultant protein:protein interactions. The majority of 265D mutant capsids increased vector genome populations in both the liver and the GC, suggesting that the 265D mutation enhances cell entry. However, while this appears advantageous in the case of hepatic transduction, transduction efficiency in GC was not enhanced in the context of the 265D mutation, suggesting that post attachment processing of the capsid is also being affected by the mutation.

In summary, our studies otter new structural insights into the influence of the VR1 region of the rAAV capsid on transduction efficiency and tissue targeting in vivo. These insights allowed the development of two conserved rational engineering strategies that improve tissue targeting following systemic administration of vector. At first glance, the VR1 deletion mutant capsid collection appears to be the more clinically relevant, as six novel vectors were developed that can perform at or above the level of rAAV9 at targeting the heart. While this is indeed a valuable advancement in rAAV vectorology, the 265D mutant capsid collection should not be overlooked in terms of clinical value. Though rAAV8 is consistently considered the best hepatic transducer in mouse models (Davidoff et al., *Mol. Ther.* 11(6):875 (2005)), and though the 265D capsid collection could not outperform rAAV8 in our study, it is also notable that rAAV8 may not be the most ideal vector for translational human gene therapy applications. Indeed, both rAAV2 and a variant of rAAV3b have been found to infect human hepatocytes with higher efficiency than rAAV8 (Lisowski et al., *Nature,* 506(7488):382 (2014)). Thus, both of our VR1 mutant capsid collections have the capacity to expand the reagent pool available for either muscle- or liver-oriented gene therapy applications. It is our hope that this expansion enables better personalization of gene therapy moving forward, perhaps allowing a patient's preexisting neutralizing antibody profile (Louis et al., *Hum. Gene Ther. Meth.* 24 (2):59 (2013)) to aid in choosing the best-suited serotype for their individual needs and enhancing the ability to readminister vector if necessary.

The foregoing is illustrative of the present invention, and is not to be construed as limiting thereof. The invention is defined by the following claims, with equivalents of the claims to be included therein.

That which is claimed is:

1. A recombinant adeno-associated virus (rAAV) capsid protein of serotype AAV3b, comprising an insertion of D directly after amino acid 264 of VP1 protein and a substitution of A for R at position 594 (VP1 numbering system), wherein an AAV vector comprising the capsid protein displays enhanced hepatic transduction from intravenous administration relative to an AAV vector comprising an unmodified version of the rAAV capsid protein.

2. A rAAV capsid protein of serotype AAV6, comprising an amino acid substitution of T265D and K531E (VP1 numbering system), wherein an AAV vector comprising the capsid protein displays enhanced hepatic transduction from intravenous administration relative to an AAV vector comprising an unmodified version of the rAAV capsid protein.

3. A polynucleotide encoding the rAAV capsid protein of claim 1 or claim 2.

4. An adeno-associated virus (AAV) capsid comprising the rAAV capsid protein of claim 1 or claim 2.

5. An adeno-associated virus (AAV) vector comprising:
   (a) the AAV capsid of claim 4; and
   (b) a nucleic acid comprising a recombinant viral template, wherein the nucleic acid is encapsidated by the AAV capsid.

6. The AAV vector of claim 5 present within a pharmaceutical composition.

7. A method of delivering a nucleic acid to a cell, the method comprising contacting the cell with the AAV vector of claim 5 under conditions sufficient for the nucleic acid to enter the cell.

8. The method of claim 7, wherein the cell is a liver cell.

9. The method of claim 7, wherein the cell is in a subject and the method comprises administering to the subject the AAV vector to thereby contact the cell.

10. A method of producing a rAAV particle, comprising providing to a cell permissive for AAV replication:
   (a) a rAAV template comprising (i) a heterologous nucleic acid, and (ii) at least one inverted terminal repeat; and
   (b) a polynucleotide comprising replication protein coding sequence(s) and sequence(s) encoding the rAAV capsid protein of claim 1;

under conditions sufficient for the replication and packaging of the rAAV template;

whereby rAAV particles are produced in the cell.

\* \* \* \* \*

UNITED STATES PATENT AND TRADEMARK OFFICE
CERTIFICATE OF CORRECTION

Page 1 of 4

PATENT NO. : 12,319,715 B2
APPLICATION NO. : 17/407716
DATED : June 3, 2025
INVENTOR(S) : Samulski et al.

It is certified that error appears in the above-identified patent and that said Letters Patent is hereby corrected as shown below:

In the Specification

Column 20, Lines 18-41, Table 4: Please delete Table 4 and replace with the following:

| Parvovirus | VR1 Amino Acid Residues |
|---|---|
| AAV1 | $_{261}$SSASTGASNDNHY$_{273}$ (SEQ ID NO:1) |
| rAAV2 | $_{261}$SSQSGAS$_{267}$ (SEQ ID NO:2) |
| rAAV3b | $_{261}$SSQSGASNDNHY$_{272}$ (SEQ ID NO:3) |
| rAAV4 | $_{256}$ESLQSNTY$_{263}$ (SEQ ID NO:4) |
| rAAV5 | $_{252}$SGSVDGS$_{258}$ (SEQ ID NO:5) |
| rAAV6 | $_{261}$SSASTGASNDNHY$_{273}$ (SEQ ID NO:6) |
| rAAV8 | $_{263}$NGTSGGAT$_{270}$ (SEQ ID NO:7) |
| rAAV9 | $_{261}$SNSTSGGSS$_{269}$ (SEQ ID NO:8) |

Signed and Sealed this
Thirtieth Day of September, 2025

John A. Squires
*Director of the United States Patent and Trademark Office*

CERTIFICATE OF CORRECTION (continued)
U.S. Pat. No. 12,319,715 B2

Column 38, Line 38: Please correct "toot" to read --foot--

Column 45, Line 16: Please correct "(SEQ H) NO:26)" to read --(SEQ ID NO:26)--

Column 46, Line 20: Please correct "1e11" to read --1e10--

Column 47, Line 37: Please correct "(F1291)" to read --(F129L)--

Column 53, Line 16 – Column 54, Line 25, Table 9: Please delete Table 9 and replace with the following:

| Construct | Primer Sequence (5' -> 3') |
|---|---|
| pXR1/T265del* | ctc cag tgc ttc agg ggc cag caa cg (SEQ ID NO:27) |
| pXR1/T265D* | gca atc tcc agt gct tca gac ggg gcc agc aac g (SEQ ID NO:13) |
| pXR1/Y445F* | cat cga cca gta cct gta ttt cct gaa cag aac tca (SEQ ID NO:28) |
| pXR2/Q263del | caa aca aat ttc cag ctc agg agc ctc g (SEQ ID NO:29) |
| pXR2/S264del | caa att tcc agc caa gga gcc tcg aac g (SEQ ID NO:3026) |
| pXR3b/Q263del | caa gca aat ctc cag ctc agg agc ttc (SEQ ID NO:31) |
| pXR3b/266D | ctc cag cca atc aga cgg agc ttc aaa cg (SEQ ID NO:32) |
| pXR3b/R594A | cag ctc cca cga ctg caa ctg tca atg atc (SEQ ID NO:33) |
| pXR4/N261del | gag cct gca gtc cac cta caa cgg (SEQ ID NO:34) |
| pXR5/258del | ccg tcg acg gaa acg cca acg cc (SEQ ID NO:35) |
| pXR6/S262del | gca aat ctc cgc ttc aac ggg gg (SEQ ID NO:36) |
| pXR7/T265del | caa atc tcc agt gaa gca ggt agt acc (SEQ ID NO:37) |
| pXR8/T265del | ctc caa cgg gtc ggg agg agc (SEQ ID NO:38) |
| pXR8/T265D | caa atc tcc aac ggg gac tcg gga gga gcc acc (SEQ ID NO:39) |
| pXR8/S266del | tct cca acg gga cag gag gag cca cc (SEQ ID NO:40) |
| pXR9/S263del | caa gca aat ctc cag cac atc tgg agg (SEQ ID NO:41) |
| pXR9/S265del | ctc caa cag cac agg agg atc ttc aaa tg (SEQ ID NO:42) |
| pXR9/T265D | caa gca aat ctc caa cag cga ctc tgg agg atc ttc aaa tg (SEQ ID NO:43) |
| pXR9/S263A_S266del | gca aat ctc caa cgc cac agg agg atc ttc aaa tga c (SEQ ID NO:44) |

Column 56, Lines 15-45, Table 10: Please delete Table 10 and replace with the following:

| Serotype | Variable Region 1 | Mutations |
|---|---|---|
| rAAV1 | $_{261}$SSASTGASNDNHY$_{273}$ (SEQ ID NO:1) | T265del+++ |
| rAAV2 | $_{261}$SSQSGAS$_{267}$ (SEQ ID NO:2) | Q263del+, S264del+ |
| rAAV3b | $_{261}$SSQSGASNDNHY$_{272}$ (SEQ ID NO:3) | Q263del++ |
| rAAV4 | $_{256}$ESLQSNTY$_{263}$ (SEQ ID NO:4) | N261del+ |
| rAAV5 | $_{252}$SGSVDGS$_{258}$ (SEQ ID NO:5) | S258del++ |
| rAAV6 | $_{261}$SSASTGASNDNHY$_{273}$ (SEQ ID NO:6) | S262del++, T265del+ |
| rAAV7 | n/a | *T265del* |
| rAAV8 | $_{263}$NGTSGGAT$_{270}$ (SEQ ID NO:7) | T265del+ |
| rAAV9 | $_{261}$SNSTSGGSS$_{269}$ (SEQ ID NO:8) | S263del++, S265del+, S263del_S265del+++ |

Column 58, Line 12: Please correct "(FIG. 174-17C)" to read --(FIG. 17A-17C)--

Column 59, Line 56 – Column 60, Line 25, Table 11: Please delete Table 11 and replace with the following:

| Serotype | Variable Region 1 | Mutations |
|---|---|---|
| rAAV1 | $_{261}$SSAS*DGASNDNHY$_{273}$ (SEQ ID NO:1) | T265D |
| rAAV2 | $_{261}$SSQS*DGAS$_{267}$ (SEQ ID NO:2) | 265D |
| rAAV3b | $_{261}$SSQS*DGASNDNHY$_{272}$ (SEQ ID NO:3) | 266D |
| rAAV6 | $_{261}$SSAS*DGASNDNHY$_{273}$ (SEQ ID NO:6) | T265D |

| rAAV8 | $_{263}$NGDSGGAT$_{270}$ (SEQ ID NO:7) * | T265D |
|---|---|---|
| rAAV9 | $_{261}$SNSDSGGSS$_{269}$ (SEQ ID NO:8) * | S265D |

Column 60, Line 51: Please correct "(SEQ H) NO:47)" to read --(SEQ ID NO:47)--